(12) United States Patent
Rudolph et al.

(10) Patent No.: US 7,517,878 B2
(45) Date of Patent: Apr. 14, 2009

(54) HETEROARYLAMINOPYRAZOLE DERIVATIVES USEFUL FOR THE TREATMENT OF DIABETES

(75) Inventors: Joachim Rudolph, Guilford, CT (US);
Philip Wickens, Wallingford, CT (US);
Chih-Yuan Chuang, San Mateo, CA (US); Libing Chen, Milford, CT (US);
Steven Magnuson, Wallingford, CT (US); Alan Olague, Shelton, CT (US);
Ning Qi, Hamden, CT (US)

(73) Assignee: Bayer Pharamceuticals Corporation, West Haven, CT (US)

( * ) Notice: Subject to any disclaimer, the term of this patent is extended or adjusted under 35 U.S.C. 154(b) by 458 days.

(21) Appl. No.: 11/064,700

(22) Filed: Feb. 24, 2005

(65) Prior Publication Data

US 2005/0192294 A1 Sep. 1, 2005

Related U.S. Application Data

(60) Provisional application No. 60/572,906, filed on May 20, 2004, provisional application No. 60/548,331, filed on Feb. 27, 2004.

(51) Int. Cl.
*C07D 403/12* (2006.01)
*A61K 31/4155* (2006.01)

(52) U.S. Cl. .................. 514/235.5; 514/341; 546/275.4; 544/124

(58) Field of Classification Search ................. 544/124; 546/275.4; 514/235.5, 341
See application file for complete search history.

(56) References Cited

OTHER PUBLICATIONS

Crenshaw et al., Interferon inducing activities of derivatives of 1,3-dimethyl-4-(3-dimethylaminopropylamino)-1H-pyrazolo[3,4-b]quinoline and related compounds, Journal of Medicinal Chemistry, 19(2): 262-275, 1976.*

* cited by examiner

*Primary Examiner*—Deepak Rao
(74) *Attorney, Agent, or Firm*—Edwards Angell Palmer & Dodge LLP; Barry Kramer; Ralph A. Loren

(57) ABSTRACT

The present invention relates to heteroarylaminopyrazole compounds, pharmaceutical compositions, and methods for treating diabetes and related disorders.

9 Claims, No Drawings

HETEROARYLAMINOPYRAZOLE DERIVATIVES USEFUL FOR THE TREATMENT OF DIABETES

This application claims benefit of U.S. Provisional Application Ser. No. 60/548,331; filed on Feb. 27, 2004, and U.S. Provisional Application Ser. No. 60/572,906; filed May 20, 2004, the contents of which are incorporated herein by reference in their entirety.

FIELD OF THE INVENTION

The present invention relates to heteroarylaminopyrazole compounds, pharmaceutical compositions, and methods for treating diabetes and related disorders.

BACKGROUND OF THE INVENTION

Diabetes is characterized by impaired glucose metabolism manifesting itself among other things by an elevated blood glucose level in the diabetic patient. Underlying defects lead to a classification of diabetes into two major groups. Type 1 diabetes, or insulin dependent diabetes mellitus (IDDM), arises when patients lack insulin-producing beta-cells in their pancreatic glands. Type 2 diabetes, or non-insulin dependent diabetes mellitus (NIDDM), occurs in patients with impaired beta-cell function and alterations in insulin action.

The current treatment for type 1 diabetic patients is injection of insulin, while the majority of type 2 diabetic patients are treated with agents that stimulate beta-cell function or with agents that enhance the tissue sensitivity of the patients towards insulin. The drugs presently used to treat type 2 diabetes include alpha-glucosidase inhibitors, insulin sensitizers, insulin secretagogues, and metformin.

Over time, almost one-half of type 2 diabetic subjects lose their response to these agents. Insulin treatment is instituted after diet, exercise, and oral medications have failed to adequately control blood glucose. The drawbacks of insulin treatment are the need for drug injection, the potential for hypoglycemia, and weight gain.

Because of the problems with current treatments, new therapies to treat type 2 diabetes are needed. In particular, new treatments to retain normal (glucose-dependent) insulin secretion are needed. Such new drugs should have the following characteristics: dependency on glucose for promoting insulin secretion (i.e., compounds that stimulate insulin secretion only in the presence of elevated blood glucose); low primary and secondary failure rates; and preservation of islet cell function.

INS-1 cells are a model for islet beta-cell insulin secretion. When maintained in the presence of beta-mercaptoethanol, these cells retain many of the characteristics of islet beta-cells in situ. The cells secrete insulin in response to physiologically relevant glucose concentrations with an $EC_{50}$ of 6 mM glucose (Hohmeier, et al., Diabetes 49:424, 2002). These cells also secrete insulin in response to multiple known secretagogues, including agents that elevate intracellular cyclic AMP, nutrients other than glucose, and potassium chloride. This characteristic of INS-1 cells further demonstrates that the cells retain many of the signaling pathways that are involved in the insulin secretory response, and as such are suitable for identifying compounds that affect these pathways. INS-1 cells are therefore useful tools for identifying compounds that stimulate insulin secretion in the presence of glucose, and such compounds are useful in the treatment of diabetes and related disorders.

DESCRIPTION OF THE INVENTION

The invention provides heteroarylaminopyrazole derivatives of Formula (I)

(I)

wherein is a substituted heterocyclic aromatic ring radical selected from

R is H, or $(C_1-C_6)$alkyl;

$R^1$ is H,
  $(C_1-C_6)$alkyl optionally substituted with phenyl, said phenyl being optionally substituted with halo, or [tri$(C_1-C_4)$alkyl]silyl,
  $(C_3-C_6)$alkenyl,
  $(C_3-C_6)$alkynyl,
  $(C_3-C_6)$cycloalkyl optionally substituted with up to two substituents selected from the group consisting of $(C_1-C_3)$alkyl, $CF_3$, and halo,
  $(C_1-C_3)$haloalkyl, or
  phenyl optionally substituted with up to two substituents selected from the group consisting of halo, $(C_1-C_6)$alkyl, $(C_1-C_6)$alkoxy, $(C_1-C_6)$alkylthio, $(C_1-C_3)$haloalkyl, $(C_1-C_3)$haloalkoxy, and cyano;

$R^2$ is H,
  halo,
  $(C_1-C_6)$alkyl, pyridyl optionally substituted with up to two substituents selected from the group consisting of $(C_1-C_6)$alkoxy, $(C_1-C_6)$alkylthio, halo, and $(C_1-C_6)$alkyl, phenyl optionally substituted with up to two substituents selected from the group consisting of $(C_1-C_6)$alkyl, $(C_1-C_6)$alkoxy, $(C_1-C_6)$alkylthio, cyano and halo, pyrimidyl, thienyl optionally substituted with up to two substituents selected from the group consisting of $(C_1-C_6)$alkyl, $(C_1-C_6)$alkoxy, $(C_1-C_6)$alkylthio, cyano and halo, benzothienyl, optionally substituted with up to two substituents selected from the group consisting of $(C_1-C_6)$alkyl, $(C_1-C_6)$alkoxy, $(C_1-C_6)$alkylthio, cyano and halo, or furyl optionally substituted with up to two substituents selected from the group consisting of $(C_1-C_6)$alkyl, $(C_1-C_6)$alkoxy, $(C_1-C_6)$alkylthio, cyano and halo;

$R^3$ is $(C_1-C_6)$alkyl,
$(C_3-C_6)$cycloalkyl,
$(C_2-C_3)$haloalkyl or
phenyl optionally substituted with up to four substituents selected from the group consisting of
   $(C_1-C_6)$alkyl optionally substituted with one $(C_1-C_4)$alkoxy,
   halo,
   $(C_1-C_3)$haloalkyl,
   $(C_1-C_6)$alkoxy,
   $(C_1-C_3)$haloalkoxy,
   $(C_1-C_6)$alkylthio, and
   cyano;

$R^4$ is $(C_1-C_6)$alkyl optionally substituted with one $(C_1-C_4)$alkoxy,
$(C_1-C_6)$alkoxy,
$(C_1-C_6)$alkylthio,
$(C_1-C_3)$haloalkyl,
$(C_1-C_3)$haloalkoxy, or
halo;

n=0, 1, 2, or 3;

X is $CO_2R^7$, $CONR^5R^6$, or $SO_2NH_2$;

$R^5$ is H, $(C_1-C_6)$alkyl, phenyl optionally substituted with halo or benzyl optionally substituted on the phenyl ring with halo;

$R^6$ is H or $(C_1-C_6)$alkyl;

or $R^5$ and $R^6$, taken together with N atom to which they are attached, may form a piperidine, morpholine, thiomorpholine, or piperazine ring said piperazine optionally substituted on N with $(C_1-C_3)$alkyl;

$R^7$ is H,
$(C_1-C_6)$alkyl,
benzyl optionally substituted on the aryl ring with up to two substituents selected from the group consisting of
   halo,
   $(C_1-C_6)$alkyl,
   $(C_1-C_3)$alkoxy,
   $(C_1-C_3)$haloalkyl,
   $(C_1-C_3)$haloalkoxy, and
   $(C_1-C_6)$alkylthio;
phenyl optionally substituted with up to two substituents selected from the group consisting of
   $(C_1-C_6)$alkyl,
   halo,
   $(C_1-C_6)$alkoxy,
   $(C_1-C_3)$haloalkyl,
   $(C_1-C_3)$haloalkoxy, and
   $(C_1-C_6)$alkylthio;

and pharmaceutically acceptable salts thereof;

provided that the compound of Formula (I) is not

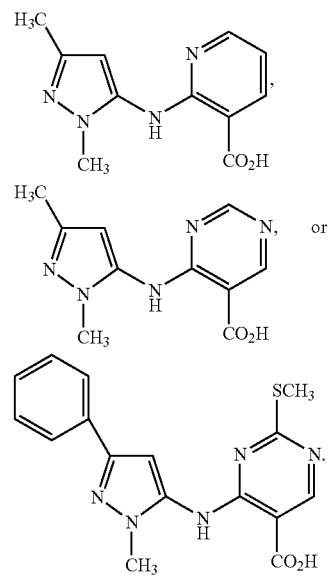

The terms identified above have the following meaning throughout:

The term "halo" means F, Br, Cl, and I.

The terms "$(C_1-C_3)$alkyl" and "$(C_1-C_6)$alkyl" mean a linear or branched saturated hydrocarbon radical having from about 1 to about 3 C atoms or about 1 to about 6 C atoms, respectively. Such groups include, but are not limited to, methyl, ethyl, n-propyl, isopropyl, butyl, isobutyl, tert-butyl, pentyl, hexyl, and the like.

The term "$(C_3-C_6)$alkenyl" means a linear or branched unsaturated hydrocarbon radical containing a double bond and from about 3 to about 6 carbon atoms. The double bond may be between any two available carbon atoms in the chain. Such groups include, but are not limited to, allyl, isopropenyl, 2-butenyl, 2-ethyl-2-butenyl, 1-hexenyl, and the like.

The term "$(C_3-C_6)$alkynyl" means a linear or branched unsaturated hydrocarbon radical containing a triple bond and from about 3 to about 6 carbon atoms. The triple bond may be between any two available carbon atoms in the chain. Such groups include, but are not limited to, propargyl, 2-butynyl, 1-methyl-2-butynyl, 3-hexynyl, and the like.

The term "$(C_3-C_6)$cycloalkyl" includes, for example, cyclopropyl, cyclobutyl, cyclopentyl, cyclohexyl, and the like.

The terms "$(C_1-C_4)$alkoxy" and "$(C_1-C_6)$alkoxy" mean a linear or branched saturated hydrocarbon radical having from about 1 to about 4 C atoms and from 1 to about 6 C atoms, respectively, said radical being attached to an O atom. The O atom is the atom through which the alkoxy substituent is attached to the rest of the molecule. Such groups include, but are not limited to, methoxy, ethoxy, n-propoxy, isopropoxy, n-butoxy, tert-butoxy, pentyloxy, hexyloxy, and the like.

The term "$(C_1-C_3)$haloalkoxy" means a $(C_1-C_3)$alkoxy group substituted on C with a halogen atom. Such groups include, but are not limited to, trifluoromethoxy, difluoromethoxy, 2,2-difluoroethoxy, 2,2,2-trifluoroethoxy, 2-chloroethoxy, 3-chloropropoxy, 1-fluoro-2,2,-dichloroethoxy, and the like.

The terms "$(C_1-C_3)$haloalkyl" and "$(C_2-C_3)$haloalkyl" mean a $(C_1-C_3)$alkyl group and a $(C_2-C_3)$alkyl group, respectively, substituted on C with a halogen atom. Such groups include, but are not limited to, trifluoromethyl, difluoroethyl, 1-fluoro-2,2-dichloroethyl, 3-chloropropyl, 4-bromohexyl, and the like.

The term "[tri$(C_1-C_4)$alkylsilyl]" means a Si radical bearing three $(C_1-C_4)$alkyl substituents, each substituent being independently selected. The Si atom is the atom through which the radical is attached to the rest of the molecule. Such groups include, but are not limited to, trimethylsilyl, tert-butyl-dimethylsilyl, and the like.

The term "$(C_1-C_6)$alkylthio" means a linear or branched saturated hydrocarbon radical having from about 1 to about 6 C atoms, said radical being attached to an S atom. The S atom is the atom through which the alkylthio substituent is attached to the rest of the molecule. Such groups include, but are not limited to, methylthio, ethylthio, n-propylthio, isopropylthio, and the like.

The term "optionally substituted" means that the moiety so modified may have from none to up to at least the highest number of substituents indicated. Each substituent may replace any H atom on the moiety so modified as of as the replacement is chemically possible and chemically stable. When there are two or more substituents on any moiety, each substituent is chosen independently from any other substituent and can, accordingly, be the same or different.

In Formula (I), the attachment point of the heterocyclic ring radicals

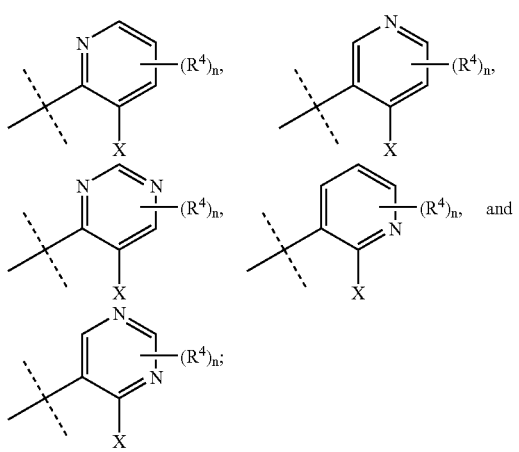

is the bond marked with a dashed line (- - -). The X group on each radical is fixed at the position ortho to the attachment point of the radical. The optional $R^4$ groups (up to n) on the radical may be located at any available C atom.

Alternative Forms Of Novel Compounds

Also included in the compounds of the present invention are (a) the stereoisomers thereof, (b) the pharmaceutically-acceptable salts thereof, (c) the tautomers thereof, (d) the protected acids and the conjugate acids thereof, and (e) the prodrugs thereof.

The stereoisomers of these compounds may include, but are not limited to, enantiomers, diastereomers, racemic mixtures, and combinations thereof. Such stereoisomers may be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the inhibitors described above.

Pharmaceutically-acceptable salts of the compounds of the present invention include salts commonly used to form alkali metal salts or form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, heterocyclic, carboxylic, and sulfonic classes of organic acids. Examples of organic and sulfonic classes of organic acids includes, but are not limited to, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicylic, galactaric, and galacturonic acid, and combinations thereof.

Tautomers of the compounds of the invention are encompassed by the present invention. Thus, for example, a carbonyl includes its hydroxy tautomer.

The protected acids include, but are not limited to, esters, hydroxyamino derivatives, amides and sulfonamides.

The present invention includes the prodrugs and salts of the prodrugs. Formation of prodrugs is well known in the art in order to enhance the properties of the parent compound; such properties include solubility, absorption, biostability, and release time (see, e.g., "*Pharmaceutical Dosage Form and Drug Delivery Systems*" (Sixth Edition), edited by Ansel et al., publ. by Williams & Wilkins, pgs. 27-29, (1995), which is hereby incorporated by reference). Commonly used prodrugs are designed to take advantage of the major drug biotransformation reactions, and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation, and acetylation (see, e.g., *Goodman and Gilman's The Pharmacological Basis of Therapeutics* (Ninth Edition), editor Molinoff et al., publ. by McGraw-Hill, pages 11-13, (1996), which is hereby incorporated by reference).

A comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87, inside cover. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87.

General Preparative Methods

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention. Unless otherwise specified in the reaction schemes the meanings of $R^1$-$R^7$, X, and

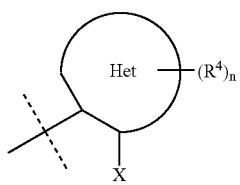

are the same as defined above.

Reaction Scheme A illustrates general methods for the preparation of compounds of Formula (Ia) [(I) where R═H]. An aminopyrazole of Formula (III) is coupled with a 2-chloro-, 2-bromo-, 2-iodo-, or 2-trifluoromethylsulfonato-heteroaryl carboxylic acid, carboxylic ester, or carboxamide of Formula (IV), using Ullmann-type conditions (e.g., copper (II) acetate in DMF, heated in a sealed tube for 16 h). Alternatively, coupling of Formula (III) to a 2-chloro, 2-bromo, 2-iodo, or 2-trifluoromethylsulfonato-heteroaryl carboxylic ester, carboxamide or sulfonamide of Formula (IV) may also be conducted using Buchwald-type conditions (e.g., cesium carbonate, BINAP and a palladium catalyst such as $Pd_2(dba)_3$ or $Pd(OAc)_2$, in anhydrous toluene, heated to 110° C. for 16 h under argon).

Reaction Scheme A

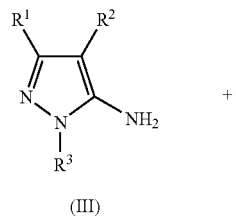

+

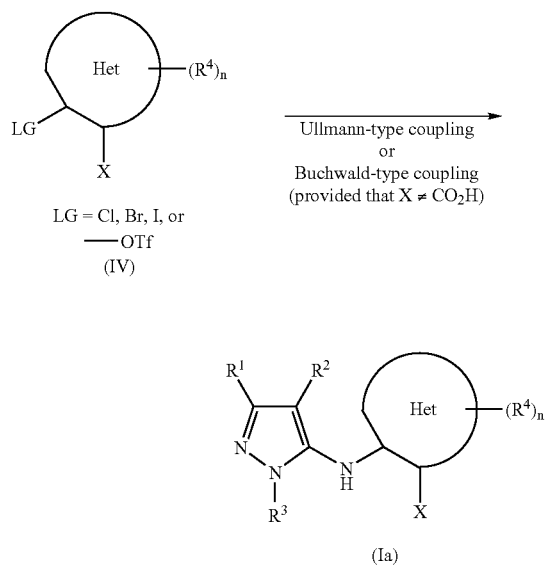

Reaction Scheme B illustrates the preparation of compounds of Formula (Id) [Formula (I) where X is COOH], and, and Formula (Ie) [Formula (I) where X is $CONR^5R^6$]. The ester compound of Formula (Ib), [Formula (I) where X is $CO_2R^7$), prepared as in Reaction Scheme A, is hydrolyzed to the acid compound of Formula (Id), usually in mild aqueous base. Formula (Id) can then be converted to amides of Formula (Ie) by reaction with an amine $R^5R^6NH$, optionally in the presence of a mixture of coupling agents such as HOBT, EDCI, and triethylamine. Alternatively, a nitrile compound of Formula (Ic) [Formula (I) where X is CN] may be directly hydrolyzed in aqueous base to provide the primary amide compound of Formula (If) [Formula (I) where X is $CONR^5R^6$ and $R^5$ and $R^6$ are H].

Reaction Scheme B

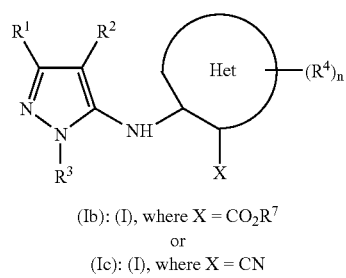

hydrolysis when X = CN

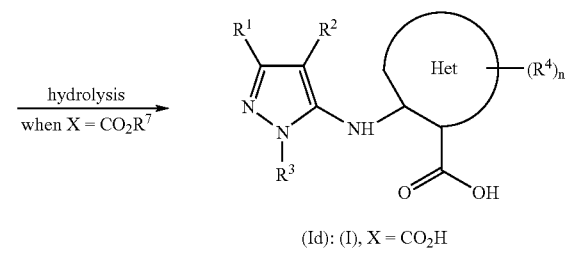

$R^5R^6NH$

-continued

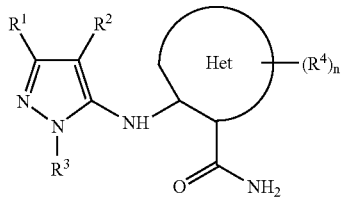

(If): (I), X = CONR⁵R⁶, and R⁵R⁶ = H

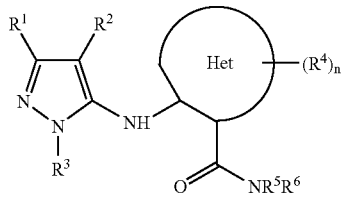

(Ie): (I), X = CONR⁵R⁶

Reaction Scheme C illustrates the general method for preparation of Formula (I) compounds where $R^2$ is iodo, chloro or fluoro. The compound of Formula (Ig) [Formula (I) where $R^2$ is H] can be iodinated or chlorinated with a reagent such as N-iodosuccinimide (NIS) or N-chlorosuccinimide (NCS) to produce the compound of Formula (Ih) [Formula (I) where $R^2$ is I or Cl]. Similarly, treatment of the Formula (Ig) compound with a fluorinating agent such as Selectfluor® provides compounds of Formula (Ii) [Formula (I) where $R^2$ is F].

Reaction Scheme C

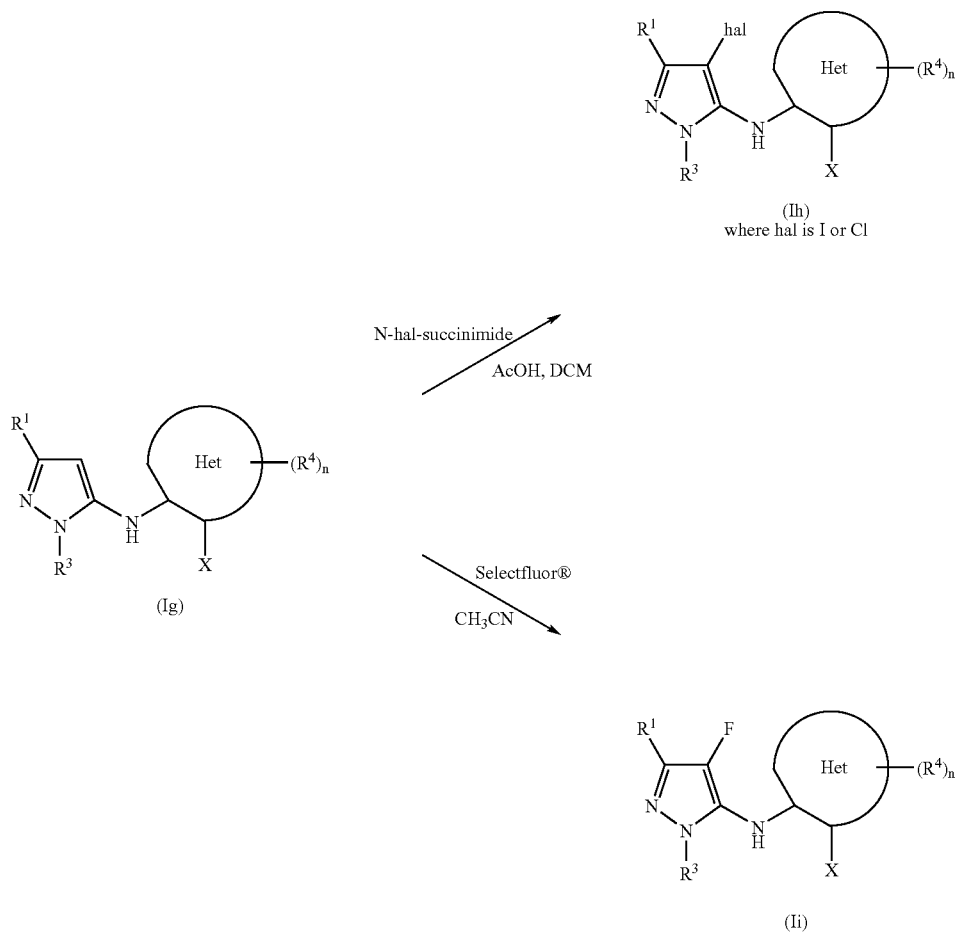

Reaction Scheme D outlines the general method for preparation of Formula (I) compounds in which X=SO$_2$NH$_2$. The N,N-dibenzylsulfonamide compound of Formula (Ij) is prepared by using the Buchwald-type coupling reaction as described in Reaction Scheme A and can be de-benzylated with sulfuric acid to give the compound of Formula (Ik).

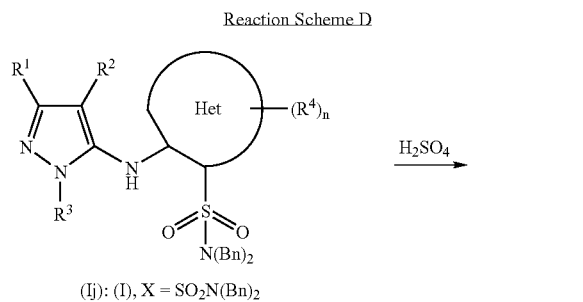

The compounds of Formula (Im) where R is (C$_1$-C$_6$)alkyl are prepared by N-alkylation of the corresponding Formula (Ia) compounds where R is H, using standard conditions such as those shown in Reaction Scheme E. Such conditions include an alkylating agent such as iodomethane, and a base such as sodium hydride, and the reaction is carried out in inert solvent such as DMF. In the case where X is a carboxylic ester, standard hydrolysis (i.e., NaOH, H$_2$O) is carried out to give the compounds of Formula (I) where R is alkyl and X is CO$_2$H.

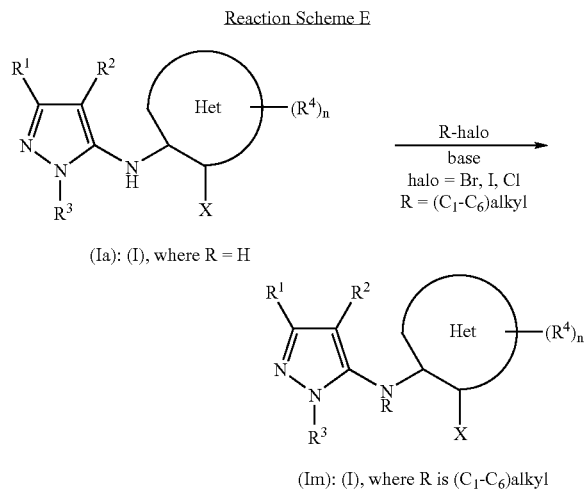

Synthesis of Intermediates

Intermediates are either commercially available, or are prepared by standard methods known in the art and/or by analogy to one of the procedures shown below.

5-Aminopyrazoles

5-Aminopyrazole starting materials of Formula (III) are either commercially available or can be prepared as shown in Reaction Schemes F, G, or H.

In Reaction Scheme F, condensation of an optionally substituted acetonitrile with an appropriately substituted ester (VI), and base, gives the cyanoketone (VII). Esters of Formula (VI) where R$^1$ is an optionally substituted phenyl, can be prepared, if necessary, from the corresponding bromo compound of Formula R$^1$—Br, for example, by reaction with BuLi and CO$_2$ to form an acid of Formula R$^1$—COOH, which can be esterified to (VI). The compound of formula (VII) is then allowed to react with a substituted hydrazine of Formula (II) or a substituted hydrazone of Formula (V) to give the desired aminopyrazole (III). If the cyanoketone (VII) is commercially available, the first step is omitted.

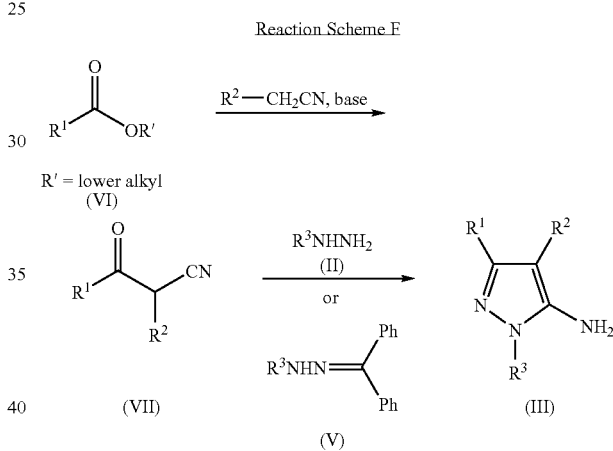

In Reaction Scheme G, a nitrile of Formula (VIII) is allowed to react with acetonitrile to form the enaminonitrile (IX), then allowed to react with the hydrazine (II) or hydrazone (V) to form (IIIa) [(III) where R$^2$=H].

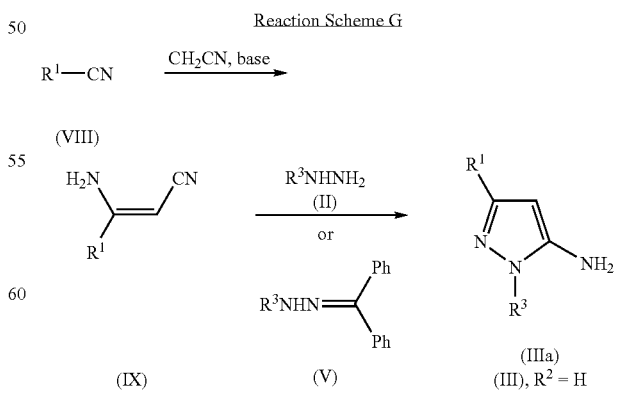

Reaction Scheme H illustrates how the aminopyrazole of Formula (IIIa) may be converted to other aminopyrazoles of Formula (III) by bromination and Suzuki coupling reaction to introduce an $R^2$ group other than H.

Reaction Scheme H

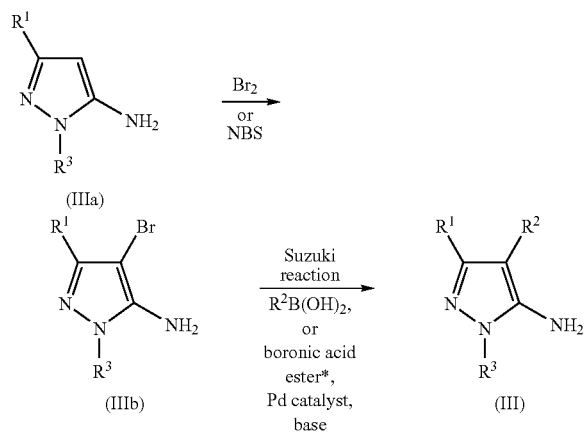

(IIIa)

(IIIb)

(III)

*Suitable boronic acid esters include
$R^2B(OR')_2$ where R' is a lower alkyl group, or two R' groups may form a ring such as

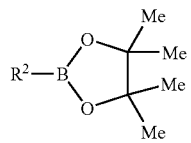

and trimeric boronic acid esters such as

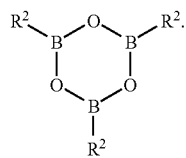

Examples of preparations of aminopyrazoles are shown in the descriptions of Intermediates B-I, below.

Hydrazines and Hydrazones

Hydrazine and hydrazone starting materials of Formula (II) and Formula (V), respectively, are either commercially available or, in the case of phenyl hydrazines ($R^3$=optionally substituted phenyl), can be prepared as shown in Reaction Scheme I, in which a substituted aniline is converted into a diazonium salt intermediate which is subsequently reduced using tin(II)chloride as the reductant.

Reaction Scheme I

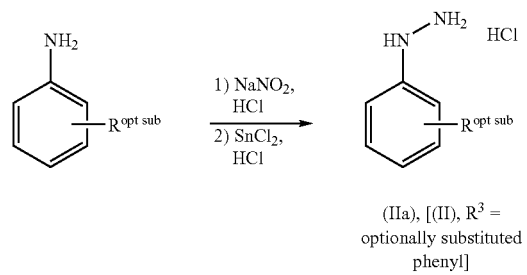

(IIa), [(II), $R^3$ = optionally substituted phenyl]

$R^{opt\ sub}$ = an optional substituent

N-phenylhydrazones can be prepared as shown in Reaction Scheme J, from a phenyl halide or phenyl trifluoromethanesulfonate and a hydrazone, such as benzophenone hydrazone, in the presence of a Pd catalyst and a base.

Reaction Scheme J

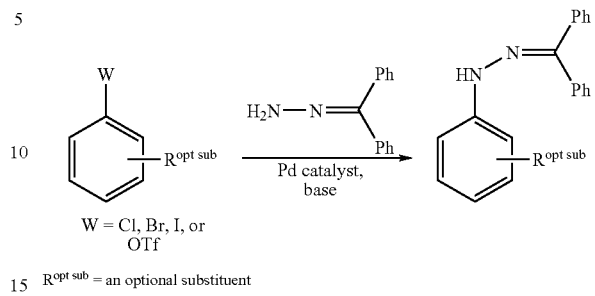

W = Cl, Br, I, or OTf $R^{opt\ sub}$ = an optional substituent

An example of a preparation of an arylhydrazine is shown in the description of Intermediate A, below. Preparative examples of arylhydrazones are shown in the descriptions of Intermediate B, step 1, and Intermediate C, step 2.

Halopyridine and Halopyrimidine Carboxylic Acid and Sulfonamide Derivatives

The halopyridine- and halopyrimidine carboxylic acid derivatives used in the coupling reactions with 5-aminopyrazoles were either commercially available or prepared by straightforward means well known in the art. Other substituents on the pyridine or pyrimidine can be introduced by standard means, such as that shown in Reaction Scheme K for the preparation of methyl 3-chloro-6-methoxypyridine-2-carboxylate.

Reaction Scheme K

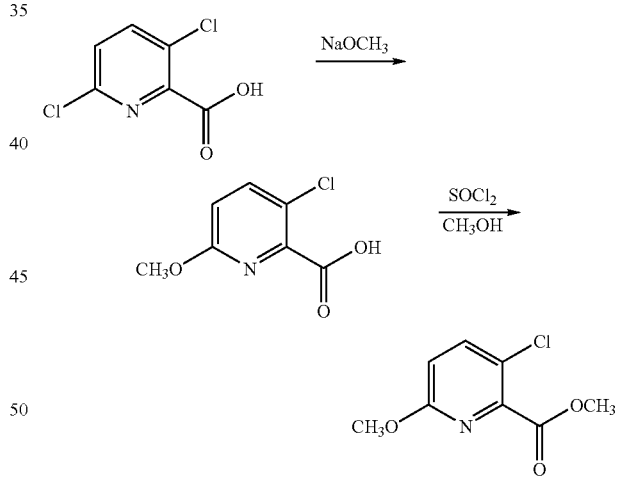

An example of one such preparation is shown in the description of Intermediate J below.

The synthesis of a 2-halopyridine sulfonamide intermediate is illustrated in Reaction Scheme L. The 2-chloro-3-aminopyridine is converted to the 2-chloropyridinesulfonyl chloride by reaction with sodium nitrite/acid and sulfuryl chloride. This compound is then allowed to react with dibenzylamine to provide the desired 2-chloropyridine 3-sulfonamide intermediate. This compound may then be carried on to a final product using the methods described in Reaction Schemes A and D.

Reaction Scheme L

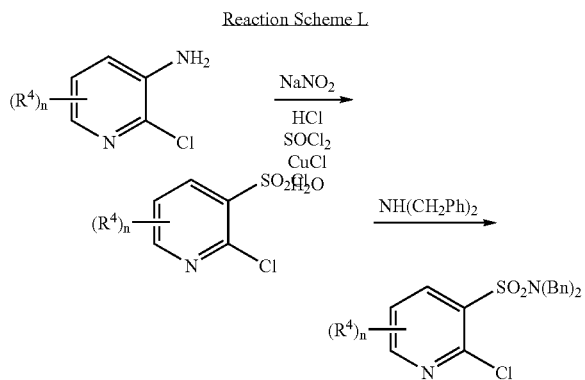

Specific Examples of the Invention

The following specific examples are presented to illustrate the invention described herein, but should not be construed as limiting the scope of the invention in any way.

Abbreviations and Acronyms

When the following abbreviations are used throughout the disclosure, they have the following meaning:
abs absolute
Ac acetyl
AcOH acetic acid
amu atomic mass unit
aq aqueous
BINAP 2,2'-Bis(diphenylphosphino)-1,1'-binaphthyl
Bn benzyl
Boc t-butoxycarbonyl
BTMAICl$_2$ benzyltrimethylammonium dichloriodate
Bu butyl
CDCl$_3$ deuterochloroform
CDI carbonyl diimidazole
Celite® brand of diatomaceous earth filtering agent, registered trademark of Celite Corporation
CI-MS chemical ionization mass spectroscopy
conc concentrated
d doublet
DCM dichloromethane
dd doublet of doublet
ddd doublet of doublet of doublet
DMAP 4-(N,N-dimethyl)amino pyridine
DMF N,N-dimethyl formamide
DMSO dimethylsulfoxide
DMSO-d$_6$ dimethylsulfoxide-d$_6$
DOWEX® 66 Dowex hydroxide, weakly basic anion, macroporous, 25-50 mesh
dppf 1,1'-bis(diphenylphosphino)ferrocene
EDCI 1-(3-dimethylaminopropyl)-3-ethylcarbodiimide hydrochloride
EI electron impact ionization
EI-MS electron impact-mass spectrometry
equiv equivalent
ES-MS electrospray mass spectrometry
Et ethyl
Et$_2$O diethyl ether
Et$_3$N triethylamine
EtOAc ethyl acetate
EtOH ethanol
g gram
GC-MS gas chromatography-mass spectrometry
h hour(s)
Hex hexanes
$^1$H NMR proton nuclear magnetic resonance
HOAT 1-hydroxy-7-aza-benzotriazole
HOBT 1-hydroxybenzotriazole
HPLC high-performance liquid chromatography
HPLC ES-MS high-performance liquid chromatography-electrospray mass spectroscopy
KOtBu potassium tert-butoxide
L liter
LC-MS liquid chromatography/mass spectroscopy
LDA lithium diisopropylamide
m multiplet
M molar
mL milliliter
m/z mass over charge
Me methyl
MeCN acetonitrile
MeOH methanol
mg milligram
MHz megahertz
min minute(s)
mmol millimole
mol mole
mp melting point
MS mass spectrometry
N normal
NaOAc sodium acetate
NBS N-bromosuccinimide
NCS N-chlorosuccinimide
NIS N-iodosuccinimide
NMM 4-methylmorpholine
NMR nuclear magnetic resonance
Pd$_2$(dba)$_3$ tris(dibenzylideneacetone)dipalladium(0)
Pd(OAc)$_2$ palladium acetate
Pd(PPh$_3$)$_4$ tetrakis(triphenylphosphine)palladium(0)
Pd/C palladium on carbon
Pd(dppf)Cl$_2$ [1,1'-bis(diphenylphosphino)ferrocene]dichloropalladium(II)
Ph phenyl
ppm parts per million
Pr propyl
psi pounds per square inch
PTSA p-toluenesulfonic acid
q quartet
qt quintet
R$_f$ TLC retention factor
rt room temperature
RT retention time (HPLC)
s singlet
TBAF tetrabutylammonium fluoride
TBDMS tert-butyldimethylsilyl
TBDMSCI tert-butyldimethylsilyl chloride
TBS tert-butyldimethylsilyl
TFA trifluoroacetic acid
THF tetrahydrofuran
TLC thin layer chromatography
TMS tetramethylsilane
V/V volume per unit volume
vol volume
w/w weight per unit weight General Experimental Methods Air and moisture sensitive liquids and solutions were transferred via syringe or cannula, and introduced into reaction vessels through rubber septa. Commercial grade reagents and solvents were used without further purification. The term "concentration under reduced pressure" refers to use of a Buchi rotary evaporator at approximately 15 mm of Hg. All temperatures are reported uncorrected in degrees Celsius (° C.). Thin layer chromatography (TLC) was performed on EM Science pre-coated glass-backed silica gel 60 A F-254 250 μm plates. Column chromatography (flash chromatography) was performed on a Biotage system using 32-63 micron, 60 A, silica gel pre-packed cartridges. Purification using preparative reversed-phase HPLC chromatography were accomplished using a Gilson 215 system, typically using a YMC Pro-C18 AS-342 (150×20 mm I.D.) column. Typically, the mobile phase used was a mixture of $H_2O$ (A) and MeCN (B). The water could be mixed or not with 0.1% TFA. A typical gradient was:

| Time [min] | A: % | B: % | Flow [mL/min] |
|---|---|---|---|
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

Electron impact mass spectra (EI-MS) were obtained with a Hewlett Packard 5989A mass spectrometer equipped with a Hewlett Packard 5890 Gas Chromatograph with a J & W DB-5 column (0.25 μM coating; 30 m×0.25 mm). The ion source was maintained at 250° C., and spectra were scanned from 50-800 amu at 2 sec per scan.

High pressure liquid chromatography-electrospray mass spectra (LC-MS) were obtained using either a:

(A) Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% to 95% B over 3.5 minutes at a flow rate of 1.0 mL/min was used with an initial hold of 0.5 minutes and a final hold at 95% B of 0.5 minutes. Total run time was 6.5 minutes.

or (B) Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-800 amu over 1.5 seconds. ELSD (Evaporative Light Scattering Detector) data was also acquired as an analog channel. The eluents were A: 2% acetonitrile in water with 0.02% TFA, and B: 2% water in acetonitrile with 0.018% TFA. Gradient elution from 10% to 90% B over 3.5 minutes at a flow rate of 1.5 mL/min was used with an initial hold of 0.5 minutes and a final hold at 90% B of 0.5 minutes. Total run time was 4.8 minutes. An extra switching valve was used for column switching and regeneration.

Routine one-dimensional NMR spectroscopy was performed on 300/400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$ and 7.26 ppm for $CDCl_3$ for $^1H$ spectra, and 39.5 ppm for DMSO-$d_6$, 1.3 ppm for $CD_3CN$, 49.0 ppm for $CD_3OD$, 53.8 ppm for $CD_2Cl_2$ and 77.0 ppm for $CDCl_3$ for $^{13}C$ spectra.

Synthesis of Intermediates

Hydrazines

Intermediate A

Preparation of (2,6-dimethylphenyl)hydrazine hydrochloride

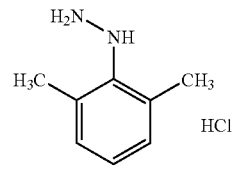

To a cold (0° C.) solution of 2,6-dimethylaniline (5.0 g, 41.3 mmol) in 50% aqueous HCl (45 mL), was added slowly under stirring a cold (0° C.) solution of $NaNO_2$ (2.85 g, 41.3 mmol) in water (22.5 mL). The temperature was closely monitored during the addition and was not allowed to exceed 5° C. Upon completion of the addition, the bright orange solution containing the diazonium salt intermediate was stirred at the same temperature for 20 min. A mixture of $SnCl_2$ (11.0 g, 57.8 mmol) in conc HCl (30 mL) was added to the reaction mixture at 0° C. over a period of ~5 min. The reaction mixture was then warmed to rt and stirred for 6 h. The precipitate was collected by filtration and washed with a small volume of cold water. Drying in vacuo afforded the title compound as a white amorphous solid (7.00 g, 98%). The product was used in the next step without further purification. ES-MS m/z 137.0 (MH$^+$); HPLC RT (min) 1.09.

5-Aminopyrazoles

Intermediate B

Preparation of 3-tert-butyl-1-(2-methoxy-5-methylphenyl)-1H-pyrazol-5-amine

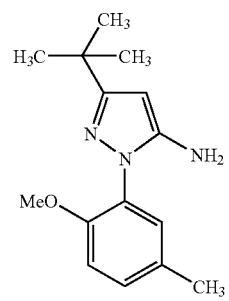

Step 1: Preparation of diphenylmethanone (2-methoxy-5-methylphenyl)hydrazone

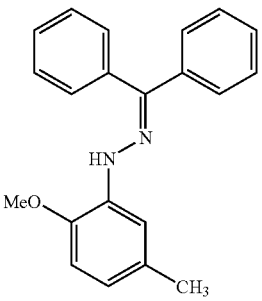

To a stirred, degassed suspension of 3-iodo-4-methoxytoluene (19.84 g, 80 mmol, 1 equiv), benzophenone hydrazone (17.99 g, 88 mmol, 1.1 equiv), Xantphos (93 mg, 0.16 mmol, 0.2 mol %), and Pd(OAc)$_2$ (36 mg, 0.16 mmol, 0.2 mol %) in anhydrous toluene (96 mL) was added NaOtBu (11.09 g, 112 mmol, 1.4 equiv) in one portion at rt. The mixture was heated to 85° C. and stirred for 12 h. The reaction mixture was cooled, diluted with 200 mL EtOAc and 100 mL water, then the layers separated. The insoluble Pd residues were separated as the aqueous layer was removed. The organic phase was washed 2×100 mL water, then brine, and dried over Na$_2$SO$_4$. The solution was concentrated under reduced pressure, giving an orange-yellow solid. The solid was triturated in 50 mL MeOH, collected via filtration, and washed with 50 mL MeOH. Drying under suction gave the title compound as a yellow solid (24.16 g, 95% yield). $^1$H NMR (400 MHz, DMSO-d$_6$) δ 2.25 (s, 3H), 3.56 (s, 3H), 6.53 (dd, 1H), 6.72 (d, 1H), 7.30 (m, 6H), 7.46 (d, 2H), 7.56 (m, 1H), 7.62 (m, 2H), 7.79 (s, 1H). ES-MS m/z 317.1 (MH$^+$); HPLC RT (min) 4.26.

Step 2: Preparation of 3-tert-butyl-1-(2-methoxy-5-methylphenyl)-1H-pyrazol-5-amine

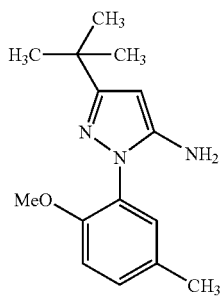

A suspension of the product in step 1 (20.0 g; 63.2 mmol; 1 equiv), 4,4-dimethyl-3-oxopentanenitrile (23.75 g; 189.6 mmol; 3 eq), and p-toluenesulfonic acid monohydrate (18.03 g; 94.8 mmol; 1.5 equiv) in abs. EtOH (400 mL) was heated to reflux and stirred for 12 h. The reaction color became yellow brown, then green. RP-HPLC showed 50-60% completion. The reaction was cooled to rt, then 100 mL of 1 N HCl was added. The reaction was heated back to reflux and stirred for 12 h. RP-HPLC after this indicated completion of the reaction. The mixture was cooled and EtOH evaporated under reduced pressure. The residue was diluted with 300 mL EtOAc and 100 mL of 1 N HCl and the layers separated. The aqueous was extracted with EtOAc (4×75 mL). The combined organic and aqueous layers were analyzed via RP-HPLC; the organic was found to contain substantial amounts of product, PTSA and impurities, while the aqueous contained only desired product and some PTSA. Thus, the combined EtOAc was extracted with 2N HCl (4×50 mL). These combined acidic layers and the EtOAc layer were analyzed again; there was no product left in the organic layer, and significant product in the acidic layer. All combined acidic layers were washed once more with 100 mL Et$_2$O, then basified to pH 8 by addition of solid NaHCO$_3$. This gave a pink solid, which was collected by filtration and washed with 2×50 mL water. The solid was triturated in 300 mL Et$_2$O, collected via filtration and washed with 100 mL Et$_2$O. Vacuum drying gave the title compound as an off-white solid (13.3 g, 81% yield). $^1$H NMR (400 MHz, DMSO-d$_6$) δ 1.18 (s, 9H), 2.25 (s, 3H), 3.74 (s, 3H), 4.69 (s, 2H), 5.25 (s, 1H), 7.01 (m, 2H), 7.13 (dd, 1H). ES-MS m/z 260.2 (MH$^+$); HPLC RT (min) 1.47.

Intermediate C

Preparation of 3-tert-butyl-1-(2-methoxy-6-methylphenyl)-1H-pyrazol-5-amine

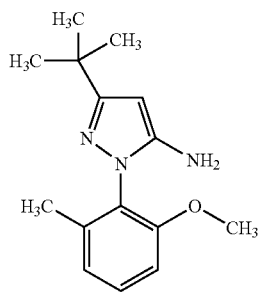

Step 1: Preparation of 2-methoxy-6-methylphenyl trifluoromethanesulfonate

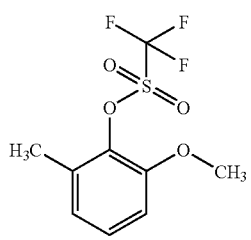

To a mixture of 2-hydroxy-3-methoxytoluene (17.0 g, 0.123 mol) and triethylamine (19.72 mL, 0.141 mol) in dichloromethane (425 mL) was slowly added trifluoromethanesulfonic anhydride (45.13 g, 0.160 mol) under cooling at 0-5° C. The mixture was then warmed to rt and stirred for 2 h. TLC (Eluent—5% EtOAc/Hexanes) indicated the disappearance of the starting material. The reaction mixture was concentrated to dryness under vacuum. Purification by silica gel chromatography using a gradient of hexanes—10% EtOAc/hexanes as eluent gave 34.37 g (99.4%) of 2-methoxy-6-methylphenyl trifluoromethanesulfonate as a clear oil.

$^1$H NMR (400 MHz, CD$_2$Cl$_2$) δ 7.25 (t, 1H), 6.90 (t, 2H), 3.90 (s, 3H), 2.37 (s, 3H); GC MS m/z 270 (M$^+$); RT (min) 8.70.

Step 2: Preparation of diphenylmethanone (2-methoxy-6-methylphenyl)hydrazone

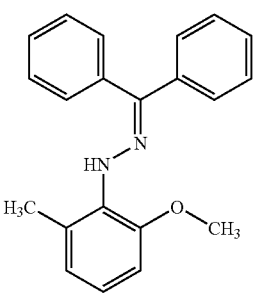

A mixture of 2-methoxy-6-methylphenyl trifluoromethanesulfonate (3.0 g, 0.011 mol), benzophenone hydrazone (2.38 g, 0.012 mol), BINAP (0.691 g, 0.001 mol), and cesium carbonate (5.06 g, 0.016 mol) in toluene (50 mL) was degassed with nitrogen. Palladium (II) acetate (0.075 g, 0.33 mol) was added, and the mixture was heated to 100° C. for 16 h. Reaction completion was judged by TLC (Eluent—5% EtOAc/Hexanes). The mixture was cooled to rt, concentrated under vacuum, and purified by silica gel chromatography using a gradient of hexanes—10% EtOAc/hexanes to afford 3.40 g (97%) of diphenylmethanone (2-methoxy-6-methylphenyl)hydrazone. $^1$H NMR (400 MHz, CD$_2$Cl$_2$) δ 7.65 (m, 2H), 7.55 (m, 3H), 7.40 (m, 2H), 7.30 (m, 3H), 6.85 (m, 2H), 6.68 (m, 1H), 3.70 (s, 3H), 2.67 (s, 3H); ES-MS m/z 317.1 (MH$^+$); HPLC RT (min) 4.23.

Step 3: Preparation of 3-tert-butyl-1-(2-methoxy-6-methylphenyl)-1H-pyrazol-5-amine

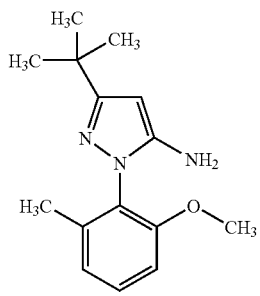

A suspension of the diphenylmethanone (2-methoxy-6-methylphenyl)hydrazone (12.1 g, 0.038 mol), 4,4-dimethyl-3-oxopentanenitrile (8.62 g, 0.069 mol), and p-toluenesulfonic acid monohydrate (43.65 g, 0.229 mol) in EtOH (217 mL) was heated to reflux for 16 h. The reaction was judged complete by TLC (Eluent—5% EtOAc/Hexanes). The reaction mixture was cooled to rt and then concentrated under vacuum. The residue was suspended in water (150 mL) and extracted with diethyl ether (6×100 mL). The extraction of excess 4,4-dimethyl-3-oxopentanenitrile was monitored by TLC (Eluent—15% EtOAc/Hexanes). The aqueous layer was basified slowly with solid NaHCO$_3$ to pH ~9.0. The aqueous layer was extracted with dichloromethane (2×200, 1×150 mL). The organic layer washed with water (150 mL), brine (100 mL), dried over sodium sulfate, filtered, and concentrated to dryness under vacuum. The product was purified by silica gel chromatography using a gradient of 10-45% EtOAc/Hexanes as eluent, to give 3.28 g (33%) of 3-tert-butyl-1-(2-methoxy-6-methylphenyl)-1H-pyrazol-5-amine.

$^1$H NMR (400 MHz, CD$_2$Cl$_2$) δ 7.32 (t, 1H), 6.92 (t, 2H), 5.50 (s, 1H), 3.82 (s, 3H), 2.02 (s, 3H), 1.29 (s, 9H); ES-MS m/z 260 (MH$^+$); HPLC RT (min) 1.46.

Intermediate D

Preparation of 3-(2,2-dimethylpropyl)-1-(2-methylphenyl)-1 pyrazol-5-yl]amine

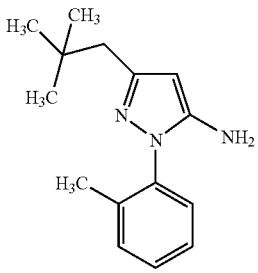

Step 1: Preparation of 5,5-dimethyl-3-oxohexanenitrile

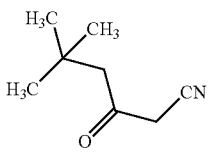

In a 500 mL dried round-bottom flask, acetonitrile (6.31, 153.6 mmol) dissolved in THF (50 mL) was treated with LiHMDS (156.3 mL, 1.0 M solution in THF) at −78° C. To this solution was added methyl 3,3-dimethylbutanoate in THF (50 mL) at −78° C. The solution was warmed to rt, and NaHCO$_3$ (100 mL, saturated solution) was added. The layers were separated and the aqueous layer was extracted with ether (3×100 mL). The combined organic layers were washed with brine, dried over Na$_2$SO$_4$, filtered, and concentrated under reduced pressure to give the desired product, which was used in the next step without purification. $^1$H NMR (300 MHz, CD$_2$Cl$_2$) δ 3.47 (s, 2H), 2.44 (s, 2H), 1.03 (s, 9H).

Step 2: Preparation of 3-(2,2-dimethylpropyl)-1-(2-methylphenyl)-1H-pyrazol-5-yl]amine

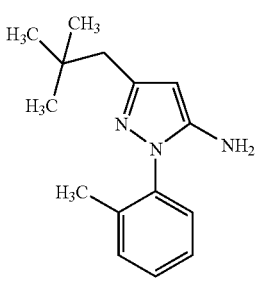

In a mixture of 5,5-dimethyl-3-oxohexanenitrile (1.5 g, 10.77 mmol) (step 1) and (2-methylphenyl)hydrazine hydrochloride (1.62, 10.24 mmol) was added aq HCl (1 N, 150 mL), and the reaction mixture was refluxed for 16 h. The resulting solution was cooled to rt, basified to pH 8 with aqueous NaOH (1 N). The precipitate was collected, and the solid was dried in a vacuum oven at 60° C. to give 1.6 g (61%) of the desired product. $^1$H NMR (300 MHz, CD$_2$Cl$_2$) δ 7.27-7.38 (m, 4H), 5.42 (s, 1H), 3.54 (br, s, 2H), 2.40 (s, 2H), 2.12 (s, 3H), 0.96 (s, 9H); ES-MS m/z 244.2 (MH$^+$); HPLC RT (min) 1.01.

Intermediate E

Preparation of 3-cyclopentyl-1-(2-methylphenyl)-1H-pyrazol-5-amine

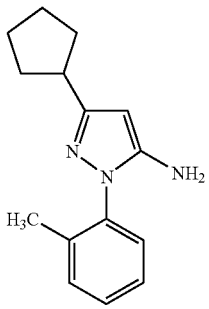

Step 1: Preparation of 3-cyclopentyl-3-oxopropanenitrile

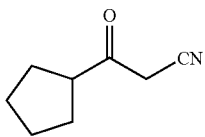

To a suspension of NaH (2.75 g, 68.7 mmol) in THF (15 mL) at 70° C. was added dropwise a solution of methyl cyclopentanecarboxylate (8.00 g, 62.4 mmol) and anhydrous acetonitrile (3.91 mL, 74.9 mmol) in THF (5 mL). The mixture was stirred for 16 h at 70-72° C., cooled to rt, and diluted with ethyl acetate and aqueous HCl. The organic layer was washed with water and brine and dried (MgSO$_4$). Removal of the solvent provided 3-cyclopentyl-3-oxopropanenitrile, which was used without further purification.

Step 2: Preparation of 3-cyclopentyl-1-(2-methylphenyl)-1H-pyrazol-5-amine

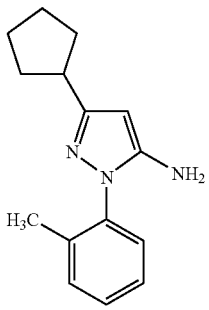

A solution of (2-methylphenyl)hydrazine hydrochloride (2.00 g, 14.6 mmol) and crude 3-cyclopentyl-3-oxopropanenitrile from the previous step (2.32 g, ~14.6 mmol) in toluene (6 mL) was heated to reflux for 16 h. Removal of the solvent under reduced pressure provided a residue which was purified by silica gel chromatography using hexane/EtOAc (3:1, v/v) as the eluent. Concentration under reduced pressure provided 3-cyclopentyl-1-(2-methylphenyl)-1H-pyrazol-5-amine as a light orange solid (2.19 g, 62%). $^1$H NMR (400 MHz, CDCl$_3$) δ 1.58-1.82 (m, 6H), 2.00-2.16 (m, 2H), 2.17-2.21 (s, 3H), 2.93-3.11 (m, 1H), 3.42-3.58 (s, 2H), 5.41-5.46 (s, 1H), 7.20-7.28 (m, 2H) 7.29-7.37 (m, 2H); ES-MS m/z 241.9 (MH$^+$); HPLC RT (min) 1.69.

Intermediate F

Preparation of 3-tert-butyl-1-(2-methylphenyl)-1H-pyrazol-5-amine

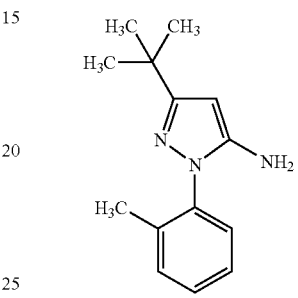

4,4-Dimethyl-3-oxopentanenitrile (36.7 g, 0.29 mol), (2-methylphenyl)hydrazine hydrochloride (47.7 g, 0.29 mol), and glacial acetic acid (7.03 g, 6.7 mL, 0.12 mol) were dissolved in abs ethanol (585 mL) and heated under reflux for 18 h. After removal of the solvent under reduced pressure, EtOAc and water (500 mL each) were added, then sodium bicarbonate (42 g, 0.50 mol) was carefully added. After addition of hexane (500 mL), the organic phase was separated, washed with brine (500 mL), and dried over Na$_2$SO$_4$. The mixture was then filtered through a pad of silica gel (500 g) on a sintered glass funnel. The pad was eluted with hexanes/EtOAc (1:1, v/v), and the filtrate was concentrated under reduced pressure. The resulting solid was triturated with hexanes/EtOAc (9:1, v/v), filtered, washed and dried in vacuo to afford the product as a colorless solid (61.5 g, 93%). $^1$H NMR (400 MHz, CD$_2$Cl$_2$) δ 1.29 (s, 9H), 2.12 (s, 3H), 3.56 (br, 2H), 5.48 (s, 1H), 7.28 (m, 2H), 7.31 (m, 2H).

Intermediate G

Preparation of 3-(4-fluorophenyl)-1-(2-methylphenyl)-1H-pyrazol-5-amine

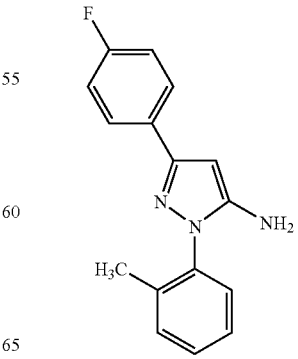

Step 1: Preparation of 3-amino-3-(4-fluorophenyl)acrylonitrile.

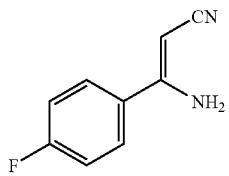

To a solution of 4-fluorobenzonitrile (5.00 g, 41.3 mmol) and acetonitrile (4.35 mL, 82.5 mmol) in toluene (100 mL) was added potassium tert-butoxide (13.9 g, 124 mmol). The mixture was stirred for 24 h, and then quenched by slow addition of aqueous sodium bicarbonate. The resulting suspension was extracted with dichloromethane (3×50 mL). The organic solution was washed with water, dried ($Na_2SO_4$), and concentrated under reduced pressure. The residue was triturated with $EtOH/Et_2O$ to afford 3-amino-3-(4-fluorophenyl)acrylonitrile (6.20 g, 93%) as a white solid. $^1$H NMR (300 MHz, acetone-$d_6$) δ 4.23 (s, 1H), 6.20 (s, 2H), 7.22 (ddd, 2H), 7.71 (m, 2H).

Step 2: Preparation of 3-(4-fluorophenyl)-1-(2-methylphenyl)-1H-pyrazol-5-amine

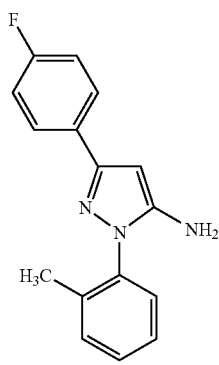

To a solution of 3-amino-3-(4-fluorophenyl)acrylonitrile (600 mg, 3.70 mmol) in 1 N HCl (6 mL) was added (2-methylphenyl)hydrazine hydrochloride (558 mg, 3.51 mmol). The reaction was allowed to reflux for 16 h, and then cooled to rt. The resulting mixture was basified to pH 12 by slow addition of 1 N aqueous sodium hydroxide. The precipitate was collected by filtration, and then recrystallized from $EtOH/Et_2O$ to afford the intermediate (800 mg, 81%) as a light orange solid. $^1$H NMR (400 MHz, $CD_2Cl_2$) δ 2.20 (s, 3H), 2.14 (br s, 2H), 5.91 (s, 1H), 7.06 (t, 2H), 7.36 (d, 4H), 7.75 (m, 2H). This material was used without further purification.

Intermediate H

Preparation of 3-tert-butyl-1-(2-methoxy-6-methylphenyl)-4-methyl-1H-pyrazol-5-amine

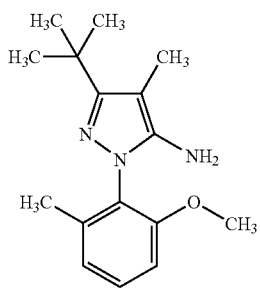

Step 1: Preparation of 4-bromo-3-tert-butyl-1-(2-methoxy-6-methylphenyl)-1H-Pyrazol-5-amine

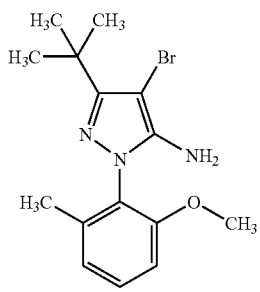

To a solution of 3-tert-butyl-1-(2-methoxy-6-methylphenyl)-1H-pyrazol-5-amine (2.00 g, 7.71 mmol) (Intermediate C) in acetic acid (15 mL) was added bromine (1170 mg, 0.38 mL, 7.33 mmol) dropwise. The reaction mixture was stirred for 5 min at rt, and then diluted with water (100 mL), causing a solid to precipitate. The solid was collected by filtration, then dissolved in EtOAc. The organic phase was then washed with saturated $NaHCO_3$ and brine, dried ($Na_2SO_4$), filtered, and concentrated under reduced pressure to afford product (2683 mg, 102%) containing minor impurities. ES-MS m/z 338.2 (MH$^+$); HPLC RT (min) 3.06.

Step 2: Preparation of 3-tert-butyl-1-(2-methoxy-6-methylphenyl)-4-methyl-1H-pyrazol-5-amine

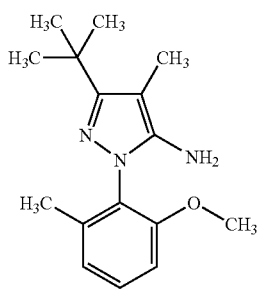

To a solution of 4-bromo-3-tert-butyl-1-(2-methoxy-6-methylphenyl)-1H-pyrazol-5-amine (2.6 g, 7.68 mmol) in DMF (15 mL) was added methylboroxine (6.66 mL, 46.08 mmol), [1,1'-bis(diphenylphosphino)-butane]palladium (II) dichloride (481.97 mg, 0.80 mmol), and potassium carbonate (3.3 g, 23.04 mmol). The reaction mixture was stirred for 18 h at 155° C. The reaction was diluted with water (100 mL) and extracted with EtOAc (3×25 mL). The combined organic extracts were washed with brine, dried (Na$_2$SO$_4$), and concentrated under reduced pressure. The residue was purified by silica gel chromatography using 90% hexane/EtOAc, to afford the product (1.7 g, 77%) as a pure white solid. $^1$H NMR (300 MHz, DMSO-d$_6$) δ 1.24 (s, 9H), 1.96 (s, 3H), 1.99 (s, 3H), 3.71 (s, 3H), 4.25 (s, 2H), 6.85 (d, 1H), 6.94 (d, 1H), 7.23-7.29 (m, 1H). ES-MS m/z 274.2 (MH$^+$); HPLC RT (min.) 1.78.

Intermediate I

Preparation of 4-(4-fluorophenyl)-3-methyl-1-(2-methylphenyl)-1 pyrazol-5-amine

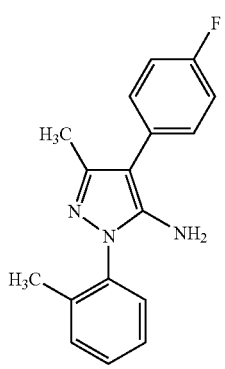

Step 1: Preparation of 4-bromo-3-methyl-1-(2-methylphenyl)-1H-Pyrazol-5-amine

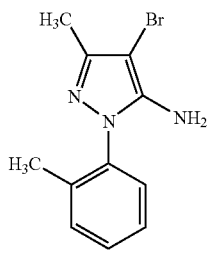

To a solution of 3-methyl-1-(2-methylphenyl)-1H-pyrazol-5-amine (7.78 g, 41.7 mmol) in acetic acid (90 mL) was added a solution of bromine (6.64 g, 41.6 mmol) in acetic acid (10 mL). The reaction mixture was stirred for 30 min. Water was added to the reaction mixture, and the mixture was basified using a cold KOH solution (1 N). The white solid, 4-bromo-3-methyl-1-(2-methylphenyl)-1H-pyrazol-5-amine, was collected and used in the next step without purification.

Step 2: Preparation of 4-(4-fluorophenyl)-3-methyl-1-(2-methylphenyl)-1H-pyrazol-5-amine

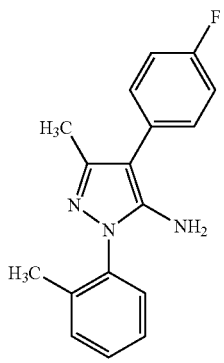

4-Bromo-3-methyl-1-(2-methylphenyl)-1H-pyrazol-5-amine (2 g, 7.52 mmol), 4-fluorophenylboronic acid (2.10 g, 11.3 mmol), and Pd(PPh$_3$)$_4$ (434 mg, 0.38 mmol) were dissolved in DMF (20 mL), and Na$_2$CO$_3$ (saturated aq solution, 18 mL) was added. The mixture was degassed for 10 min and then heated at 110° C. for 2 h. The reaction mixture was diluted, and the solid was filtered off. The solvent was concentrated under reduced pressure, and the residue purified by silica gel flash chromatography using 10 to 40% ethyl acetate in hexanes to give 1.2 g (90% pure, 51%) of the title compound. $^1$H NMR (300 MHz, CD$_2$Cl$_2$) δ 7.25-7.34 (m, 6H), 7.08 (t, 2H), 3.62 (s, 2H), 2.20 (s, 3H), 2.14 (s, 3H).

Intermediate J

Preparation of methyl 3-chloro-6-methoxypyridine-2-carboxylate

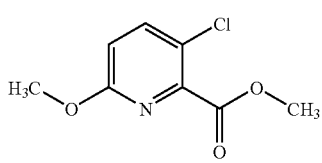

Step 1: Preparation of 3-chloro-6-methoxypyridine-2-carboxylic acid

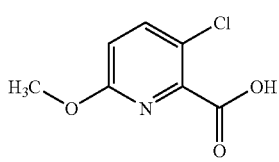

To a solution of 3,6-dichloropyridine-2-carboxylic acid (7.10 mmol 1.36 g) in dioxane (15 mL) was added sodium methoxide (21.31 mmol 1.15 g) in methanol dropwise. The mixture was stirred at 85° C. for 14 h, cooled to rt, and diluted with ethyl acetate and aqueous HCl. The organic layer was washed with water and brine, and dried (MgSO$_4$). Removal of the solvent provided 3-chloro-6-methoxypyridine-2-carboxylic acid which was used in the next step without further purification.

Step 2: Preparation of methyl 3-chloro-6-methoxypyridine-2-carboxylate

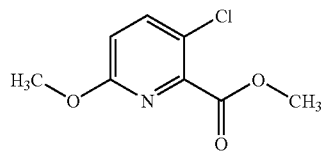

Thionyl chloride (5 mL) was added to 3-chloro-6-methoxypyridine-2-carboxylic acid (7.10 mmol, 1.30 g) under argon at rt, and the mixture was then heated to reflux for 2 h. After cooling to rt, the excess thionyl chloride was removed under reduced pressure to afford the acid chloride as a yellow oil. Anhydrous methanol was then slowly added with stirring at 0° C., and the reaction solution was warmed to rt and stirred for 4 h. The excess methanol was removed, and the residue was neutralized with saturated NaHCO$_3$ and extracted with EtOAc. The organic layer was dried over MgSO$_4$ and evaporated to afford the product as a white solid which was used without further purification. $^1$H NMR (400 MHz, DMSO-d$_6$) δ 3.84 (s, 3H), 3.86 (s, 3H), 7.05 (d, 1H), 7.92 (d, 1H).

EXAMPLES OF THE INVENTION

Example 1

Preparation of 2-{[3-tert-butyl-1-(2-methylphenyl)-1 pyrazol-5-yl]amino}-6-methylnicotinic acid

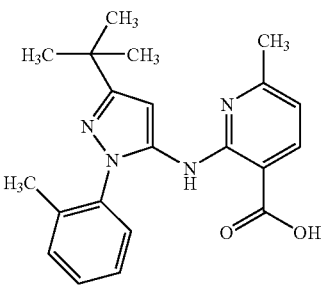

A mixture of 2-chloro-6-methylnicotinic acid (122 mg, 0.71 mmol), potassium carbonate (108 mg, 0.78 mmol), 3-tert-butyl-1-(2-methylphenyl)-1H-pyrazol-5-amine (Intermediate F, 163 mg, 0.71 mmol), and copper (II) acetate (2.6 mg, 0.014 mmol) in DMF (2 mL) was heated (150° C.) in a sealed tube for 16 h. The mixture was cooled to rt, filtered through a silica gel plug using ethyl acetate as eluent, concentrated to dryness, and subjected to HPLC purification using a gradient elution from 30% to 90% acetonitrile in water. This afforded 182.2 mg (70%) of the desired product. $^1$H NMR (300 MHz, CD$_3$OD) δ 8.14 (d, 1H), 7.14-7.51 (m, 4H), 7.01 (s, 1H), 6.80 (d, 1H), 2.53 (s, 3H), 2.10 (s, 3H), 1.40 (s, 9H); ES-MS m/z 365.3 (MH$^+$); HPLC RT (min) 3.23.

By using the conditions described for Example 1 above, and by substituting the appropriate starting materials, Examples 11-75 and 147-150 were similarly prepared and are described in Table 1 below.

Example 2

Preparation of 2-{[3-cyclopentyl-1-(2-methylphenyl)-1H-pyrazol-5-yl]amino}nicotinic acid

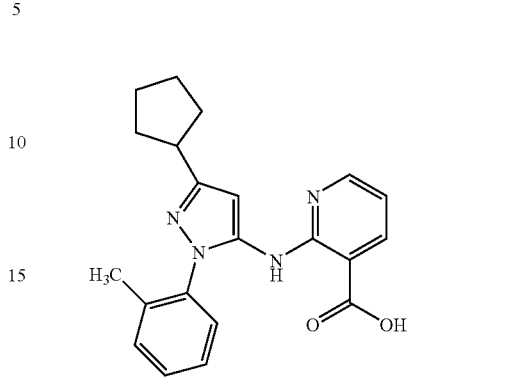

A mixture of 2-chloronicotinic acid (113 mg, 0.72 mmol), potassium carbonate (199 mg, 1.44 mmol), 3-cyclopentyl-1-(2-methylphenyl)-1H-pyrazol-5-amine (174 mg, 0.72 mmol) (Intermediate E), and copper (II) acetate (6.5 mg, 0.04 mmol) in DMF (3 mL) was heated (150° C.) in a sealed tube for 16 h. The mixture was cooled to rt, filtered through a silica gel plug using ethyl acetate as eluent, concentrated to dryness, and subjected to HPLC purification using a gradient elution from 30% to 90% acetonitrile in water to afford 59.7 mg (23%) of the desired product.

$^1$H NMR (300 MHz, CD$_2$Cl$_2$) δ 10.69 (s, 1H), 8.36 (dd, 1H), 8.16 (dd, 1H), 7.52 (d, 2H), 7.32-7.41 (m, 2H), 6.93 (dd, 1H), 6.82 (s, 1H), 3.11-3.22 (m, 1H), 2.19-2.21 (m, 2H), 1.94 (s, 3H), 1.65-1.89 (m, 6H); ES-MS m/z 363.2 (MH$^+$), HPLC RT (min) 3.57.

Example 3

Preparation of 3-{[1-(5-fluoro-2-methylphenyl)-3-methyl-4-phenyl-1H-pyrazol-5-yl]amino}isonicotinic acid

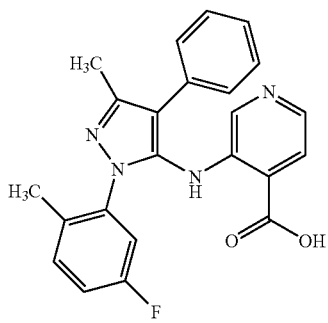

A mixture of 3-iodoisonicotinic acid (180 mg, 0.72 mmol), potassium carbonate (199 mg, 1.44 mmol), 1-(5-fluoro-2-methylphenyl)-3-methyl-4-phenyl-1H-pyrazol-5-amine (202 mg, 0.72 mmol, synthesized in the same manner as Intermediate F, using commercially available 2-phenylacetonitrile as the nitrile source), and copper (II) acetate (6.5 mg, 0.04 mmol) in DMF (1 mL) was heated (150° C.) in a sealed tube for 16 h. The mixture was cooled to rt, filtered through a silica gel plug using ethyl acetate as eluent, concentrated to dryness, and subjected to HPLC purification using a gradient elution from 30% to 90% acetonitrile in water to afford 29.1 mg (10%) of the desired product. $^1$H NMR (300 MHz, CD$_3$CN) δ 9.39 (br s, 1H), 7.93 (s, 1H), 7.86-7.90 (m, 2H), 7.05-7.45 (m, 8H), 2.38 (s, 3H), 2.15 (s, 3H); ES-MS m/z 403.1 (MH$^+$), HPLC RT (min) 2.40.

Example 4

Preparation of 3-{[3-tert-butyl-1-(2-methylphenyl)-1H-pyrazol-5-yl]amino}pyridine-2-carboxylic acid

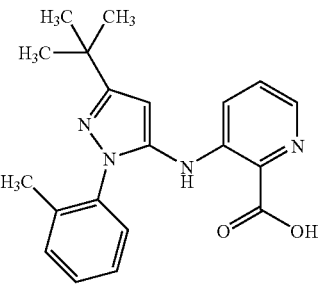

A mixture of 3-bromopyridine-2-carboxylic acid (71 mg, 0.35 mmol), potassium carbonate (53 mg, 0.39 mmol), 3-tert-butyl-1-(2-methylphenyl)-1H-pyrazol-5-amine (80 mg, 0.35 mmol) (Intermediate F), and copper (II) acetate (1.3 mg, 0.007 mmol) in DMF (1 mL) was heated (150° C.) in a sealed tube for 16 h. The mixture was cooled to rt, filtered through with a silica gel plug using ethyl acetate as eluent. The mixture was concentrated to dryness and subjected to HPLC purification using a gradient elution from 30% to 90% acetonitrile in water to afford 2.8 mg (2.3%) of the desired product. $^1$H NMR (300 MHz, CD$_3$OD) δ 8.11 (dd, 2H), 7.79 (dd, 1H), 7.32-7.45 (m, 4H), 6.45 (s, 1H), 2.11 (s, 3H), 1.40 (s, 9H); ES-MS m/z 351.0 (MH$^+$), HPLC RT (min) 2.46.

Example 5

Preparation of 5-{[1-(2,5-dimethylphenyl)-3-(4-fluorophenyl)-1H-pyrazol-5-yl]amino}-2-(methylthio)pyrimidine-4-carboxylic acid

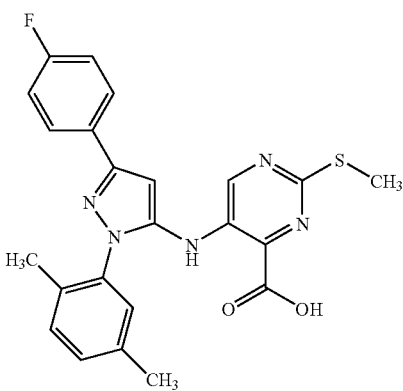

A mixture of 5-chloro-2-(methylthio)pyrimidine-4-carboxylic acid (89 mg, 0.44 mmol), potassium carbonate (66 mg, 0.48 mmol), 1-(2,5-dimethylphenyl)-3-(4-fluorophenyl)-1H-pyrazol-5-amine (123 mg, 0.44 mmol), synthesized in a similar manner as Intermediate G, and copper (II) acetate (1.6 mg, 0.009 mmol) in DMF (1 mL) was heated (150° C.) in a sealed tube for 16 h. The mixture was cooled to rt, filtered through a silica gel plug using ethyl acetate as eluent, concentrated to dryness, and subjected to HPLC purification using a gradient elution from 30% to 90% acetonitrile in water to afford 24.2 mg (12.3%) of the desired product. $^1$H NMR (300 MHz, CD$_2$Cl$_2$) δ 8.95 (s, 1H), 8.90 (s, 1H), 7.85 (dd, 2H), 7.10-7.28 (m, 5H), 7.62 (s, 1H), 2.58 (s, 3H), 2.38 (s, 3H), 2.14 (s, 3H); ES-MS m/z 406.3 (MH$^+$-CO$_2$), HPLC RT (min) 4.07.

Example 6

Preparation of 2-[(3-methyl-1-phenyl-1H-pyrazol-5-yl)amino]nicotinamide

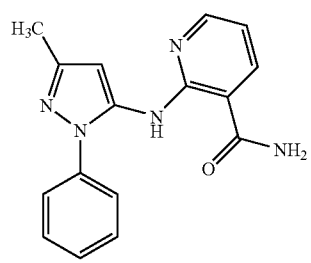

Step 1: Preparation of 2-[(3-methyl-1-phenyl-1H-pyrazol-5-yl)amino]nicotinic acid

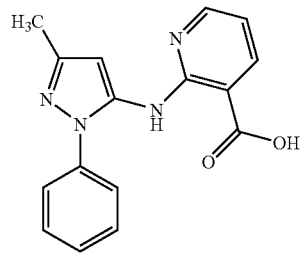

To a solution of 3-methyl-1-phenyl-1H-pyrazol-5-amine (600 mg, 3.46 mmol) and 2-chloronicotinic acid (546 mg, 3.46 mmol) in DMF (6 mL), was added potassium carbonate (543 mg, 3.93 mmol) and copper (II) acetate (18 mg). The mixture was stirred at 150° C. for 18 h, and then cooled to rt, and diluted with ethyl acetate (2×) and water. The solution was adjusted to pH 2-3 using 1 N aqueous HCl. The mixture was extracted with EtOAc (3×5 mL), and then the combined organic extracts were washed with brine, dried (MgSO$_4$), and concentrated under reduced pressure. The residue was purified by HPLC (20-90% acetonitrile in water) to afford the product (126 mg, 18%) as an off-white solid. $^1$H NMR (400 MHz, DMSO-d$_6$) δ 2.19 (s, 3H), 6.62 (s, 1H), 6.77 (m, 1H), 7.34 (m, 1H), 7.45 (m, 2H), 7.53 (m, 2H), 8.16 (d, 1H), 8.22 (d, 1H), 12.32 (s, 1H); ES-MS m/z 295.1 (MH$^+$); HPLC RT (min) 2.17.

Step 2: Preparation of 2-[(3-methyl-1-phenyl-1H-pyrazol-5-yl)amino]nicotinamide

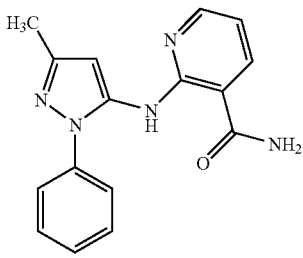

To a solution of 2-[(3-methyl-1-phenyl-1H-pyrazol-5-yl)amino]nicotinic acid (40 mg, 0.14 mmol), EDCI (52 mg, 0.27 mmol), HOAT (37 mg, 0.27 mmol), and triethylamine (0.06 mL, 0.41 mmol) in dichloromethane (4 mL) was added ammonia (7 N) in methanol (0.2 mL). The reaction mixture was stirred at rt for 16 h. The organic layer was washed with water, dried over $MgSO_4$, and subsequently concentrated under reduced pressure. The product was purified on a silica gel preparative plate (1000 microns) with EtOAc/hexane (2:1, v/v) to obtain the product as a white solid (22 mg, 55%). $^1$H NMR (400 MHz, DMSO-$d_6$) δ 2.2 (s, 3H), 6.63 (s, 1H), 6.89 (m, 1H), 7.38 (m, 1H), 7.50 (m, 4H), 7.71 (s, 1H), 8.15 (d, 1H), 8.24 (s, 1H), 8.33 (d, 1H), 11.56 (s, 1H); ES-MS m/z 294.1 (MH$^+$); HPLC RT (min) 2.02.

Example 7

Preparation of 2-{[3-(4-fluorophenyl)-1-(2-methylphenyl)-1H-pyrazol-5-yl]amino}nicotinamide

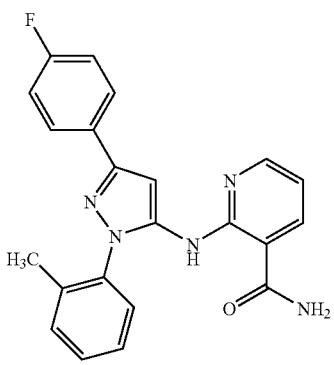

A mixture of 2-chloronicotinamide (59 mg, 0.37 mmol), potassium carbonate (57 mg, 0.41 mmol), 3-(4-fluorophenyl)-1-(2-methylphenyl)-1H-pyrazol-5-amine (100 mg, 0.37 mmol) (Intermediate G), and copper (II) acetate (1.4 mg, 0.007 mmol) in DMF (1 mL) was heated (150° C.) in a sealed tube for 16 h. The mixture was cooled to rt, filtered through a silica gel plug using ethyl acetate as eluent, concentrated to dryness, and subjected to HPLC purification using a gradient elution from 30% to 90% acetonitrile in water to afford 20 mg (14%) of the desired product.
$^1$H NMR (300 MHz, CD$_2$Cl$_2$) δ 10.88 (s, 1H), 8.48 (dd, 1H), 7.89 (dd, 2H), 7.74 (dd, 1H), 7.35-7.50 (m, 4H), 7.28 (s, 1H), 7.12 (t, 2H), 6.82 (dd, 1H), 5.85 (br, s, 2H), 2.16 (s, 3H); ES-MS m/z 388.2 (MH$^+$), HPLC RT (min) 3.61.

By using the conditions described for Example 7 above, and by substituting the appropriate starting materials, Examples 76-94 were similarly prepared and are described in Table 1 below.

Example 8

Preparation of 2-{[3-(2,2-dimethylpropyl)-1-(2-methylphenyl)-1 pyrazol-5-yl]amino}nicotinic acid

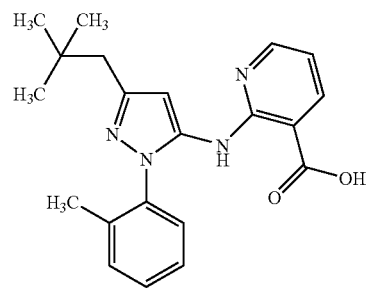

Step 1: Preparation of ethyl 2-{[3-(2,2-dimethylpropyl)-1-(2-methylphenyl)-1H-pyrazol-5-yl]amino}nicotinate

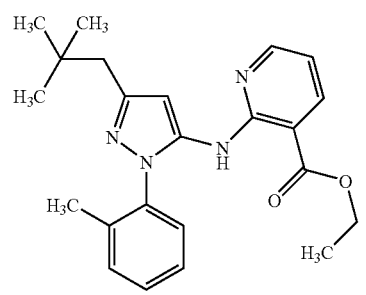

To a dried 15 mL tube was added 3-(2,2-dimethylpropyl)-1-(2-methylphenyl)-1H-pyrazol-5-yl]amine (200 mg, 0.82 mmol) (Intermediate D), ethyl 2-chloronicotinate (185 mg, 0.82 mmol), Pd$_2$(dba)$_3$ (37.6 mg, 0.041 mmol), BINAP (51.2 mg, 0.082 mmol), and Cs$_2$CO$_3$ (535.6 mg, 1.64 mmol). The flask was degassed followed by addition of toluene (2 mL), and the mixture was then heated to 110° C. for 20 h. The mixture was cooled to rt, filtered through a silica gel plug using ethyl acetate as eluent, concentrated to dryness, and subjected to HPLC purification using a gradient elution from 45% to 90% acetonitrile in water to afford 275 mg (85%) of the desired product. $^1$H NMR (300 MHz, CD$_2$Cl$_2$) δ 10.04 (s, 1H), 8.44 (dd, 1H), 8.21 (dd, 1H), 7.34-7.48 (m, 4H), 6.82 (dd, 1H), 6.75 (s, 1H), 4.19 (q, 2H), 2.57 (s, 2H), 2.12 (s, 3H), 1.28 (t, 3H), 1.02 (s, 9H); ES-MS m/z 393.3 (MH$^+$); HPLC RT (min) 4.33.

Step 2: Preparation of 2-{[3-(2,2-dimethylpropyl)-1-(2-methylphenyl)-1H-Pyrazol-5-yl]amino}nicotinic acid

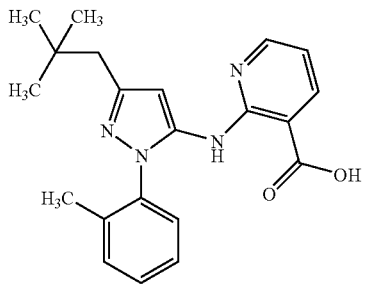

To a solution of ethyl 2-{[3-(2,2-dimethylpropyl)-1-(2-methylphenyl)-1H-pyrazol-5-yl]amino}nicotinate (266 mg, 0.68 mmol) (step 1) in a mixture of ethanol (1 mL) and THF (1 mL) was added lithium hydroxide monohydrate (284 mg, 6.8 mmol) in water (2 mL), and the mixture was then heated to 40° C. for 1 h. The reaction mixture was cooled to rt, the pH of the solution was adjusted to 5 by addition of 0.5 N hydrochloric acid solution, and was concentrated to dryness. The crude product was redissolved in methanol and subjected to HPLC purification using a gradient elution from 30% to 90% acetonitrile in water to afford 240 mg (97%) of the desired product. $^1$H NMR (300 MHz, CD$_2$Cl$_2$) δ 10.39 (s, 1H), 8.43 (dd, 1H), 8.14 (dd, 1H), 7.25-7.42 (m, 4H), 6.81-6.86 (m, 2H), 2.57 (s, 2H), 2.05 (s, 3H), 1.00 (s, 9H); ES-MS m/z 365.3 (MH$^+$); HPLC RT (min) 3.67.

By using the conditions described for Example 8 above, and by substituting the appropriate starting materials, Examples 85-116 and 129-146 were similarly prepared and are described in Table 1 below. Using either Pd$_2$(dba)$_3$ or Pd(OAc)$_2$ in step 1 for Example 116 gave similar yields.

Example 9

Preparation of 2-{[1-(2-chlorophenyl)-3-(4-fluorophenyl)-1 pyrazol-5-yl]amino}nicotinic acid

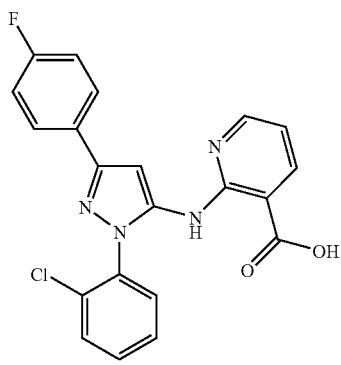

Step 1: Preparation of ethyl 2-{[1-(2-chlorophenyl)-3-(4-fluorophenyl)-1H-Pyrazol-5-yl]amino}nicotinate

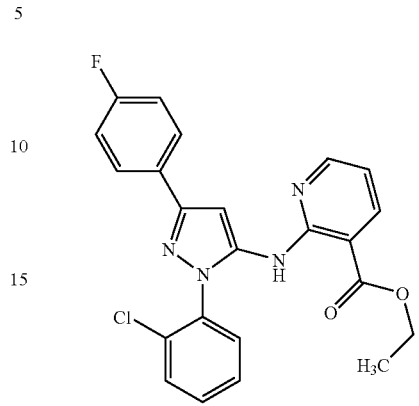

To a dried 15 mL tube was added 1-(2-chlorophenyl)-3-(4-fluorophenyl)-1H-pyrazol-5-amine (300 mg, 1.04 mmol), synthesized in the same manner as intermediate G, ethyl 2-chloronicotinate (194 mg, 1.04 mmol), Pd$_2$(dba)$_3$ (48 mg, 0.05 mmol), BINAP (65 mg, 0.10 mmol), and Cs$_2$CO$_3$ (679 mg, 2.09 mmol). The flask was degassed followed by addition of toluene (4 mL) and the mixture was then heated to 110° C. for 20 h. The mixture was cooled to rt, filtered through a silica gel plug using ethyl acetate as eluent, concentrated to dryness, and subjected to HPLC purification using a gradient elution from 45% to 90% acetonitrile in water to afford 410 mg (90%) of the desired product. $^1$H NMR (300 MHz, CD$_2$Cl$_2$) δ 10.17 (s, 1H), 8.46 (dd, 1H), 8.22 (dd, 1H), 7.89 (dd, 2H), 7.48-7.64 (m, 4H), 7.23 (s, 1H), 7.12 (t, 2H), 7.84 (dd, 1H), 4.24 (q, 2H), 1.32 (t, 3H); ES-MS m/z 437.2 (MH$^+$); HPLC RT (min) 4.38.

Step 2: Preparation of 2-{[1-(2-chlorophenyl)-3-(4-fluorophenyl)-1H-pyrazol-5-yl]amino}nicotinic acid

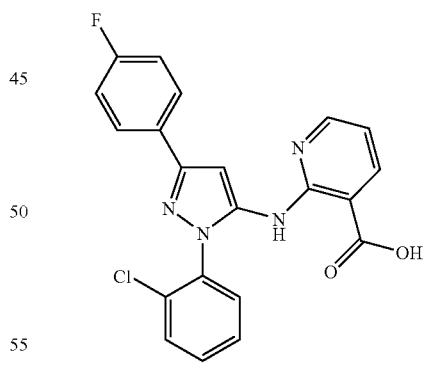

To a solution of ethyl 2-{[1-(2-chlorophenyl)-3-(4-fluorophenyl)-1H-pyrazol-5-yl]amino}nicotinate (410 mg, 0.94 mmol) in a mixture of ethanol (4 mL) and THF (4 mL) was added lithium hydroxide monohydrate (115 mg, 2.74 mmol) in water (8 mL), and the mixture was then heated to 40° C. for 1 h. The reaction mixture was cooled to rt, and the pH of the solution was adjusted to 5 by addition of 0.5 N hydrochloric acid solution (the mixture turned cloudy). The solid was filtered off and washed with more water. The solid was dried in a vacuum oven at 60° C. to give 380 mg of the desired product (99%). ¹H NMR (300 MHz, CD$_2$Cl$_2$) δ 10.18 (s, 1H), 8.45 (dd, 1H), 8.24 (dd, 1H), 7.87 (dd, 2H), 7.47-7.62 (m, 4H), 7.23 (s, 1H), 7.12 (t, 2H), 6.85 (dd, 1H); ES-MS m/z 351.2 (MH$^+$); HPLC RT (min) 2.58.

Example 10

Preparation of 3-{[3-tert-butyl-1-(2,6-dimethylphenyl)-1 pyrazol-5-yl]amino}Pyridine-2-carboxylic acid

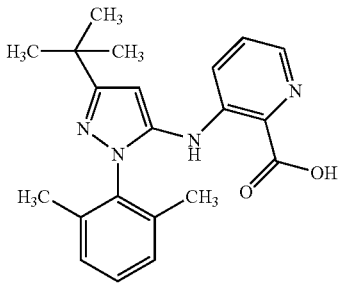

Step 1: Preparation of ethyl 3-{[(trifluoromethyl)sulfonyl]oxy}pyridine-2-carboxylate

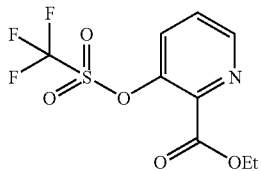

To 3-hydroxypyridine-2-carboxylic acid (25 g, 179.5 mmol) in a 1 L dried flask was added 400 mL ethanol and 100 mL toluene followed by the addition of 10 mL sulfuric acid. The mixture was heated at reflux (95° C.) for 3 days. After cooling to rt, the mixture was concentrated to ¼ of its volume, and diluted with 600 mL ethyl acetate and 200 mL water. The aqueous layer was extracted with 200 mL ethyl acetate, and the combined organic layers were washed with sat NaHCO$_3$ (3×200 mL), brine, and dried over Na$_2$SO$_4$. The solid was filtered off and the solvent was concentrated under reduced pressure to give 21.9 g of ethyl 3-hydroxypyridine-2-carboxylate (73%), which was used in the next step without purification. This ester (21.9 g, 131 mmol) was dissolved in pyridine and cooled to −40° C., followed by addition of trifluoromethanesulfonic anhydride (48 g, 170 mmol). The reaction mixture was then warmed to 0° C. for 30 min, and then warmed to rt for another 30 min. Water (100 mL) was added to quench the reaction. The mixture was extracted with ethyl acetate (3×200 mL), and the combined organic layers were washed with sat sodium bicarbonate (200 mL), water (200 mL), brine (200 mL), and dried over sodium sulfate. The solid was filtered off, and the solvent was removed under reduced pressure to give 39 g (99%) of desired product, which was used in the next step without further purification. ¹H NMR (300 MHz, CD$_2$Cl$_2$) δ 8.73 (dd, 1H), 7.72 (dd, 1H), 7.62 (dd, 1H), 4.46 (q, 2H), 1.42 (t, 3H).

Step 2: Preparation of ethyl 3-{[3-tert-butyl-1-(2,6-dimethylphenyl)-1H-pyrazol-5-yl]amino}pyridine-2-carboxylate

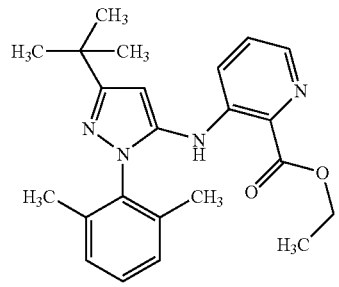

To a dried 100 mL flask was added 3-tert-butyl-1-(2,5-dimethylphenyl)-1H-pyrazol-5-amine (1.68 g, 6.9 mmol), synthesized in the same manner as Intermediate F using Intermediate A, ethyl 3-{[(trifluoromethyl)sulfonyl]oxy}pyridine-2-carboxylate (1.88 g, 6.28 mmol) (from step 1), Pd$_2$(dba)$_3$ (0.28 g, 0.31 mmol), BINAP (0.39 g, 0.63 mmol), and Cs$_2$CO$_3$ (4.1 g, 12.5 mmol). The flask was degassed followed by addition of toluene (10 mL) and the mixture was then heated to 110° C. for 4 h. The mixture was cooled to rt, filtered through a Celite® plug with ethyl acetate as eluent, concentrated to dryness, and purified by silica gel flash chromatography with 10 to 30% of ethyl acetate in hexanes to afford 1.4 g (57%) of the desired product. ¹H NMR (300 MHz, CD$_2$Cl$_2$) δ 9.29 (s, 1H), 8.19 (dd, 1H), 7.82 (dd, 1H), 7.41 (dd, 1H), 7.31 (dd, 1H), 7.19 (d, 2H), 6.18 (s, 1H), 4.28 (q, 2H), 2.01 (s, 6H), 1.39 (s, 9H), 1.32 (t, 3H); ES-MS m/z 393.2 (MH$^+$); HPLC RT (min) 3.57.

Similar yields for this step were obtained when Pd$_2$(dba)$_3$ was substituted by Pd(OAc)$_2$.

Step 3: Preparation of 3-{[3-tert-butyl-1-(2,6-dimethylphenyl)-1H-pyrazol-5-yl]amino}pyridine-2-carboxylic acid

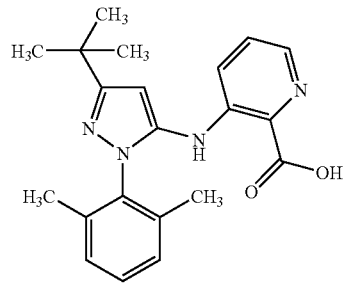

To a solution of ethyl 3-{[3-tert-butyl-1-(2,6-dimethylphenyl)-1H-pyrazol-5-yl]amino}pyridine-2-carboxylate (2.10 g, 5.35 mmol) in a mixture of ethanol (5 mL) and THF (5 mL) was added lithium hydroxide monohydrate (1.12 mg, 26.8 mmol) in water (10 mL), and the mixture was then heated to 40° C. for 1 h. The reaction mixture was cooled to rt, the pH of the solution was adjusted to 5 by addition of 0.5 N hydrochloric acid, and the mixture was concentrated to dryness. The crude mixture was redissolved in methanol and subjected to HPLC purification using a gradient elution from 30% to 90% acetonitrile in water to afford 1.65 g (85%) of the desired product. ¹H NMR (300 MHz, CD₂Cl₂) δ 10.22 (br, s, 1H), 9.52 (s, 1H), 8.03 (dd, 1H), 7.86 (dd, 1H), 7.50 (dd, 1H), 7.30 (dd, 1H), 7.18 (d, 2H), 2.02 (s, 6H), 1.37 (s, 9H); ES-MS m/z 321.3 (MH⁺); HPLC RT (min.) 2.56.

Example 11

Preparation of 4-{[3-tert-butyl-1-(2,5-dimethylphenyl)-1H-pyrazol-5-yl]amino}-2-(methylthio)pyrimidine-5-carboxylic acid

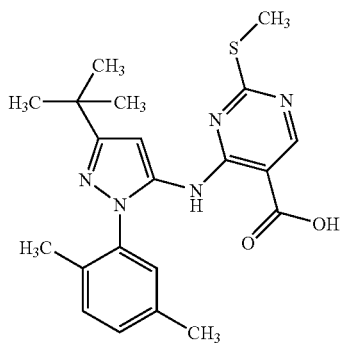

Step 1: Preparation of ethyl 4-{[3-tert-butyl-1-(2,5-dimethylphenyl)-1H-pyrazol-5-yl]amino}-2-(methylthio)pyrimidine-5-carboxylate

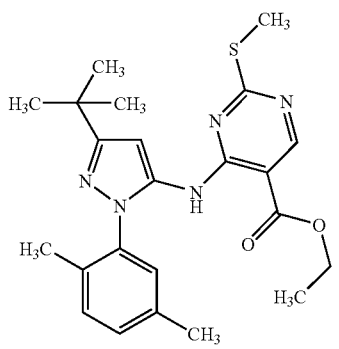

To a dried 15 mL tube was added 3-tert-butyl-1-(2,5-dimethylphenyl)-1H-pyrazol-5-amine (106 mg, 0.44 mmol), synthesized in the same manner as intermediate F, ethyl 4-chloro-2-(methylthio)pyrimidine-5-carboxylate (101 mg, 0.44 mmol), Pd₂(dba)₃ (20 mg, 0.022 mmol), BINAP (27 mg, 0.044 mmol), and Cs₂CO₃ (199 mg, 0.61 mmol). The flask was degassed followed by addition of toluene (2 mL), and the mixture was then heated to 110° C. for 20 h. The mixture was cooled to rt, filtered through a silica gel plug using ethyl acetate as eluent, concentrated to dryness, and subjected to HPLC purification using a gradient elution from 45% to 90% acetonitrile in water to afford 81 mg (42%) of the desired product. ¹H NMR (300 MHz, CD₂Cl₂) δ 10.23 (s, 1H), 8.72 (s, 1H), 7.24 (dd, 2H), 7.16 (s, 1H), 6.78 (s, 1H), 4.20 (q, 2H), 2.64 (s, 3H), 2.38 (s, 3H), 2.04 (s, 3H), 1.34 (s, 9H), 1.28 (t, 3H);. ES-MS m/z 440.2 (MH⁺); HPLC RT (min) 4.66.

Step 2: Preparation of 4-{[3-tert-butyl-1-(2,5-dimethylphenyl)-1H-Pyrazol-5-yl]amino}-2-(methylthio)pyrimidine-5-carboxylic acid

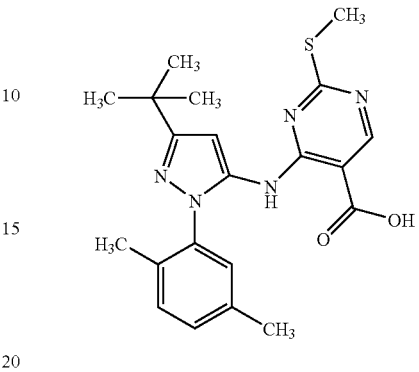

To a solution of ethyl 4-{[3-tert-butyl-1-(2,5-dimethylphenyl)-1H-pyrazol-5-yl]amino}-2-(methylthio)pyrimidine-5-carboxylate (71 mg, 0.16 mmol) in a mixture of ethanol (0.5 mL) and THF (0.5 mL) was added lithium hydroxide monohydrate (68 mg, 1.6 mmol) in water (1 mL), and the mixture was then heated to 40° C. for 1 h. The reaction mixture was cooled to rt, the pH of the solution was adjusted to 5 by addition of 0.5 N hydrochloric acid, and the mixture was concentrated to dryness. The crude mixture was redissolved in methanol and subjected to HPLC purification using a gradient elution from 30% to 90% acetonitrile in water to afford 66 mg (99%) of the desired product. ¹H NMR (300 MHz, CD₂Cl₂) δ 10.50 (s, 1H), 8.65 (s, 1H), 7.17 (dd, 2H), 7.12 (s, 1H), 6.83 (s, 1H), 2.68 (s, 3H), 2.27 (s, 3H), 1.97 (s, 3H), 1.35 (s, 9H); ES-MS m/z 412.2 (MH⁺); HPLC RT (min) 3.94.

Example 12

Preparation of 3-{[3-tert-butyl-1-(2,6-dimethylphenyl)-4-fluoro-1H-pyrazol-5-yl]amino}pyridine-2-carboxylic acid

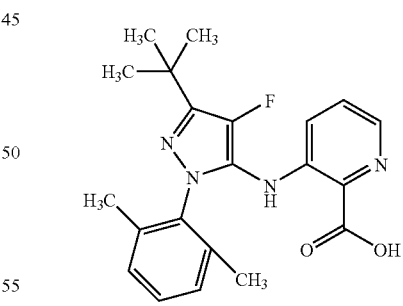

To a solution of 3-{[3-tert-butyl-1-(2,6-dimethylphenyl)-1H-pyrazol-5-yl]amino}pyridine-2-carboxylic acid (Example 10, 50 mg, 0.14 mmol) in CH₃CN (1 mL) was added [(1-(chloromethyl)-4-fluoro-1,4-diazoniabicyclo[2.2.2]octane bis(tetrafluoroborate)] (SELECTFLUOR™) (48 mg, 0.14 mmol), and the mixture was stirred at rt for 16 h. The mixture was concentrated, and the residue was subjected to HPLC purification with a gradient elution from 10% to 90% acetonitrile in water to afford 22 mg (42%) of the title compound. ¹H NMR (300 MHz, CD₂Cl₂) δ 9.18 (s, 1H), 8.04 (d, 1H), 7.50 (dd, 1H), 7.42 (m, 1H), 7.28 (m, 1H), 7.13 (m, 2H), 2.12 (s, 6H), 1.40 (s, 9H). ES-MS m/z 383.1 (MH+); HPLC RT (min) 3.21.

Example 13

Preparation of 3-{[3-tert-butyl-1-(2,6-dimethylphenyl)-4-iodo-1H-pyrazol-5-yl]amino}pyridine-2-carboxylic acid

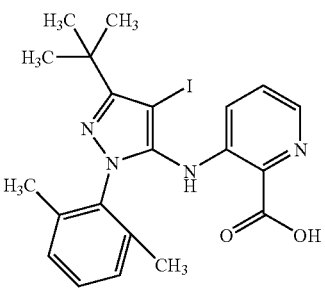

To a solution of 3-{[3-tert-butyl-1-(2,6-dimethylphenyl)-1H-pyrazol-5-yl]amino}pyridine-2-carboxylic acid (Example 10, 50 mg, 0.14 mmol) in an acetic acid/dichloromethane mixture (1 mL of each) was added N-iodosuccinimide (31 mg, 0.14 mmol). The solution was stirred at rt for 12 h, and then water (10 mL) was added. The reaction mixture was basified to pH 9 using KOH (1.0 M ice cold solution). The water layer was extracted with dichloromethane (50 mL), and the organic phase was subsequently washed with saturated sodium sulfite, brine, and concentrated to dryness. The crude material was subjected to HPLC purification to give the desired product (51 mg, 75%). $^1$H NMR (300 MHz, CD$_2$Cl$_2$) δ 9.70 (s, 1H), 9.20 (s, 1H), 8.04 (m, 1H), 7.45 (m, 1H), 7.20 (m, 2H), 7.10 (m, 2H), 2.12 (s, 6H), 1.50 (s, 9H). ES-MS m/z 490.9 (MH+); HPLC RT (min) 3.40.

Example 14

Preparation of 3-{[3-tert-butyl-4-chloro-1-(2,6-dimethylphenyl)-1H-pyrazol-5-yl]amino}pyridine-2-carboxylic acid

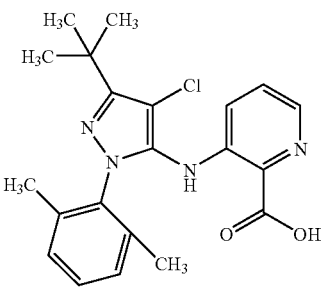

To a solution of 3-{[3-tert-butyl-1-(2,6-dimethylphenyl)-1H-pyrazol-5-yl]amino}pyridine-2-carboxylic acid (Example 10, 50 mg, 0.14 mmol) in an acetic acid/dichloromethane mixture (1 mL of each) was added N-chlorosuccinimide (18 mg, 0.14 mmol). The solution was stirred at rt for 12 h, and then water (10 mL) was added. The reaction mixture was basified to pH 9 using KOH (1.0 M ice cold solution). The water layer was extracted with dichloromethane (50 mL), and the organic phase was subsequently washed with saturated sodium sulfite, brine, and concentrated to dryness. The crude material was subjected to HPLC purification to give the desired product (42 mg, 76%). $^1$H NMR (300 MHz, CD$_2$Cl$_2$) δ 10.45 (s, 1H), 9.30 (s, 1H), 8.04 (d, 1H), 7.50 (m, 1H), 7.25 (m, 2H), 7.15 (m, 2H), 2.02 (s, 6H), 1.43 (s, 9H). ES-MS m/z 399.0 (MH+); HPLC RT (min) 3.33.

Example 15

Preparation of 2-{[3-(1,1-dimethylpropyl)-1-(3-fluoro-2-methoxyphenyl)-1H-Pyrazol-5-yl]amino}-N,N-dimethylnicotinamide

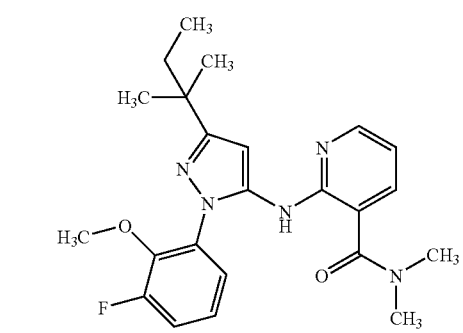

To a solution 2-{[3-(1,1-dimethylpropyl)-1-(3-fluoro-2-methoxyphenyl)-1H-pyrazol-5-yl]amino}nicotinic acid, (Example 140, synthesized in a manner similar to that of Example 8, 50 mg, 0.13 mmol) in CH$_3$CN (1 mL) was added 1 drop of dimethyl formamide followed by oxalyl chloride (9 μL, 0.13 mmol). The mixture was stirred at rt for 1 h, followed by addition of methyl amine (16 μL of a 40% solution in water, 0.25 mmol). The mixture was again stirred at rt for 1 h and concentrated to dryness. The residue was dissolved in methanol (1 mL), filtered through an octyl solid phase extraction tube and subjected to HPLC purification with a gradient elution from 10% to 90% acetonitrile in water to afford 33 mg (70%) of the desired product. $^1$H NMR (300 MHz, CD$_2$Cl$_2$) δ 8.30 (d, 1H), 8.23 (s, 1H), 7.50 (d, 1H), 7.15-7.30 (m, 3H), 6.80 (t, 1H), 6.60 (s, 1H), 3.77 (s, 3H), 2.95 (br s, 6H), 1.70 (q, 2H), 1.32 (s, 6H), 0.85 (t, 3H). ES-MS m/z 426.2 (MH+); HPLC RT (min) 3.57.

By using the conditions described for Example 15 above, and by substituting the appropriate starting materials, Examples 151-156 were similarly prepared and are described in Table 1 below.

Example 16

Preparation of 3-[(3-tert-butyl-1-methyl-1H-pyrazol-5-yl)amino]pyridine-2-carboxamide

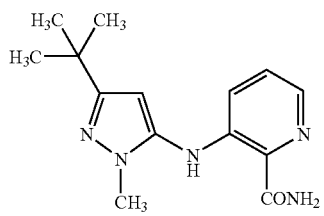

Step 1: Preparation of 3-[(3-tert-butyl-1-methyl-1H-pyrazol-5-yl)amino]pyridine-2-carbonitrile

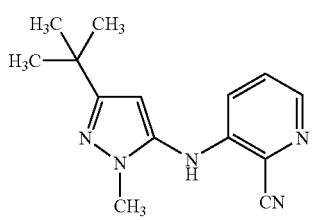

A mixture of 3-bromopyridine-2-carbonitrile (150 mg, 0.98 mmol), 3-tert-butyl-1-methyl-1H-pyrazol-5-amine (179 mg, 0.98 mmol), cesium carbonate (638 mg, 1.96 mmol), BINAP (98 mg, 0.16 mmol) and Pd$_2$(dba)$_3$ (90 mg, 0.10 mmol) was taken in anhydrous toluene (2 mL) and heated to 80° C. for 24 h under nitrogen atmosphere. The reaction mixture was cooled to rt, diluted with ethyl acetate, filtered and concentrated under reduced pressure. The residue was purified by silica gel chromatography using EtOAc/Hex (1:9 to 1:4, v/v) as the eluent. The product was obtained as a yellow oil (145 mg, 58%). ES-MS m/z 256.1 (MH$^+$); HPLC RT (min) 2.37.

Step 2: Preparation of 3-[(3-tert-butyl-1-methyl-1H-pyrazol-5-yl)amino]pyridine-2-carboxamide

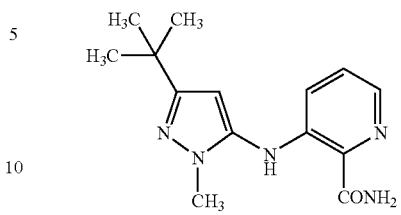

To a solution of 3-[(3-tert-butyl-1-methyl-1H-pyrazol-5-yl)amino]pyridine-2-carbonitrile (100 mg, 0.39 mmol) in MeOH (1 mL) was added an aqueous solution of KOH (3 M, 1 mL), and the mixture was stirred at 40° C. for 48 h. The organic solvent was removed under reduced pressure, and the aqueous layer was acidified to pH 1 to 2 with 1 N aqueous HCl. The mixture was extracted with ethyl acetate (3×). After removal of the solvent under reduced pressure, the crude residue was subjected to preparative HPLC purification with a gradient elution from 20% to 90% acetonitrile in water to give the above product as an oil (6.2 mg, 6%). $^1$H NMR (400 MHz, CD$_3$OD) δ 1.35 (s, 9H), 3.72 (s, 3H), 6.80 (s, 1H), 7.39-7.42 (m, 2H), 8.08-8.11 (m, 1H). ES-MS m/z 274.1 (MH$^+$), HPLC RT (min) 1.47.

Using the methods described above for preparative Examples 1-16, and the appropriate intermediates as starting materials, additional compounds of the invention were similarly prepared. These are listed in Table 1 below.

TABLE 1

| Example No | Structure | IUPAC name | LC-MS RT [min] | [M + H]$^+$ |
|---|---|---|---|---|
| 1 | 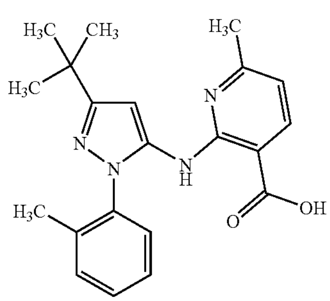 | 2-{[3-tert-butyl-1-(2-methylphenyl)-1H-pyrazol-5-yl]amino}-6-methylnicotinic acid | 3.23 | 365.3 |
| 2 | 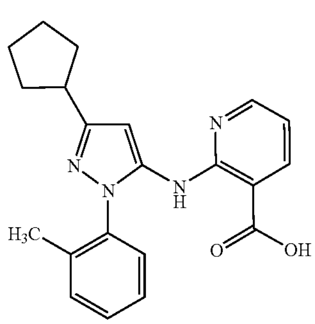 | 2-{[3-cyclopentyl-1-(2-methylphenyl)-1H-pyrazol-5-yl]amino}nicotinic acid | 3.57 | 363.2 |

TABLE 1-continued

| Example No | Structure | IUPAC name | LC-MS RT [min] | [M + H]+ |
|---|---|---|---|---|
| 3 | 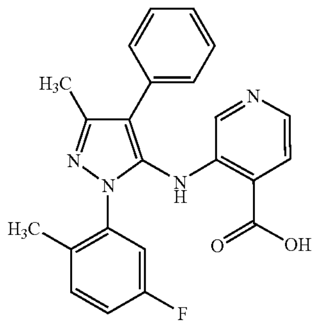 | 3-{[1-(5-fluoro-2-methylphenyl)-3-methyl-4-phenyl-1H-pyrazol-5-yl]amino}isonicotinic acid | 2.40 | 403.1 |
| 4 | 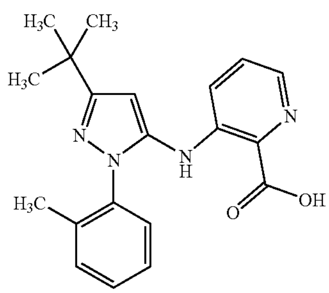 | 3-{[3-tert-butyl-1-(2-methylphenyl)-1H-pyrazol-5-yl]amino}pyridine-2-carboxylic acid | 2.46 | 351 |
| 5 | 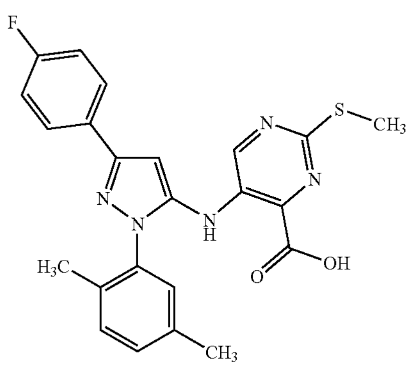 | 5-{[1-(2,5-dimethylphenyl)-3-(4-fluorophenyl)-1H-pyrazol-5-yl]amino}-2-(methylthio)pyrimidine-4-carboxylic acid | 4.07 | 450.1 [M + H]+ (—CO$_2$) = 406.3 |
| 6 | 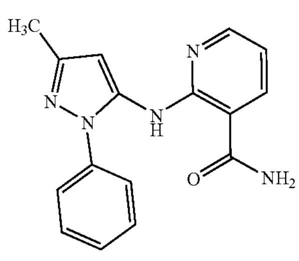 | 2-[(3-methyl-1-phenyl-1H-pyrazol-5-yl)amino]nicotinamide | 2.02 | 294.1 |

TABLE 1-continued

| Example No | Structure | IUPAC name | LC-MS RT [min] | [M + H]+ |
|---|---|---|---|---|
| 7 | 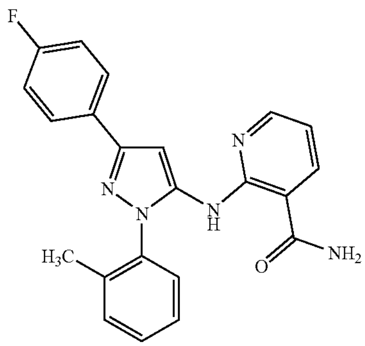 | 2-{[3-(4-fluorophenyl)-1-(2-methylphenyl)-1H-pyrazol-5-yl]amino}nicotinamide | 3.61 | 388.2 |
| 8 | 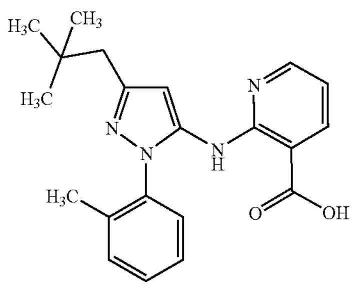 | 2-{[3-(2,2-dimethylpropyl)-1-(2-methylphenyl)-1H-pyrazol-5-yl]amino}nicotinic acid | 3.67 | 365.3 |
| 9 | 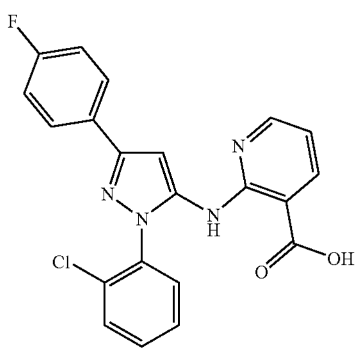 | 2-{[1-(2-chlorophenyl)-3-(4-fluorophenyl)-1H-pyrazol-5-yl]amino}nicotinic acid | 3.77 | 409.1 |
| 10 | 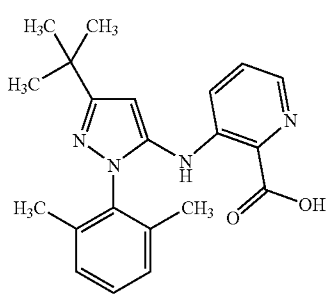 | 3-{[3-tert-butyl-1-(2,6-dimethylphenyl)-1H-pyrazol-5-yl]amino}pyridine-2-carboxylic acid | 2.56 | 365 |

TABLE 1-continued

| Example No | Structure | IUPAC name | LC-MS RT [min] | [M + H]+ |
|---|---|---|---|---|
| 11 | 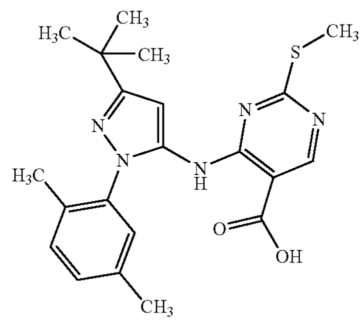 | 4-{[3-tert-butyl-1-(2,5-dimethylphenyl)-1H-pyrazol-5-yl]amino}-2-(methylthio)pyrimidine-5-carboxylic acid | 3.94 | 412.2 |
| 12 | 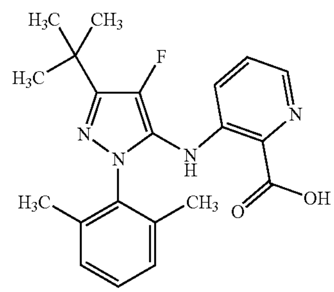 | 3-{[3-tert-butyl-1-(2,6-dimethylphenyl)-4-fluoro-1H-pyrazol-5-yl]amino}pyridine-2-carboxylic acid; | 3.21 | 383.1 |
| 13 | 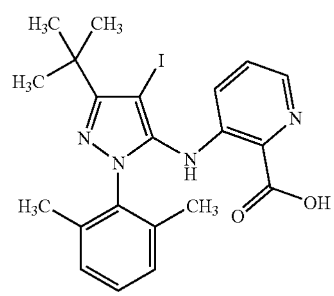 | 3-{[3-tert-butyl-1-(2,6-dimethylphenyl)-4-iodo-1H-pyrazol-5-yl]amino}pyridine-2-carboxylic acid; | 3.4 | 490.9 |
| 14 | 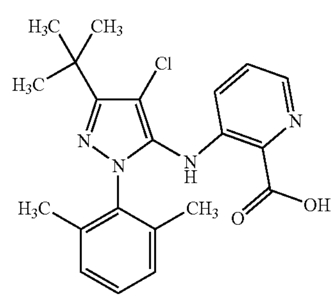 | 3-{[3-tert-butyl-4-chloro-1-(2,6-dimethylphenyl)-1H-pyrazol-5-yl]amino}pyridine-2-carboxylic acid; | 3.33 | 399 |
| 15 | 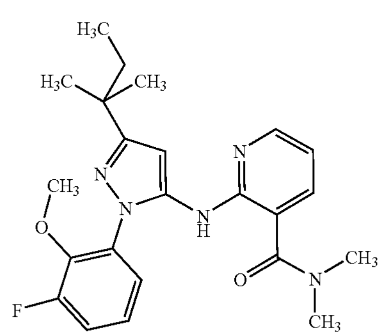 | 2-{[3-(1,1-dimethylpropyl)-1-(3-fluoro-2-methoxyphenyl)-1H-pyrazol-5-yl]amino}-N,N-dimethylnicotinamide; | 3.57 | 426.2 |

TABLE 1-continued

| Example No | Structure | IUPAC name | LC-MS RT [min] | [M + H]+ |
|---|---|---|---|---|
| 16 | 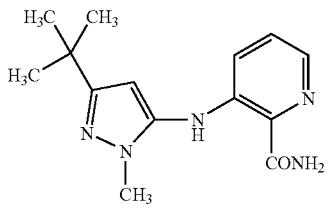 | 3-[(3-tert-butyl-1-methyl-1H-pyrazol-5-yl)amino]pyridine-2-carboxamide; | 1.47 | 274.1 |
| 17 | 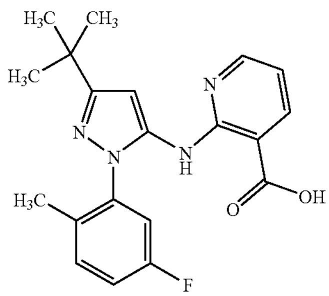 | 2-{[3-tert-butyl-1-(5-fluoro-2-methylphenyl)-1H-pyrazol-5-yl]amino}nicotinic acid | 3.36 | 369.2 |
| 18 | 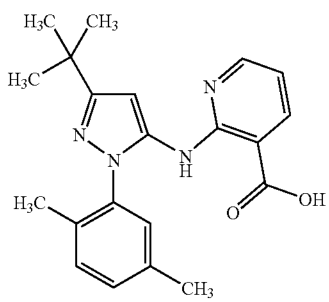 | 2-{[3-tert-butyl-1-(2,5-dimethylphenyl)-1H-pyrazol-5-yl]amino}nicotinic acid | 3.30 | 365.2 |
| 19 | 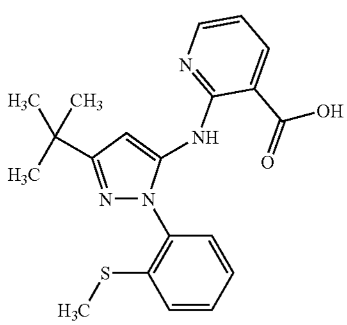 | 2-({3-tert-butyl-1-[2-(methylthio)phenyl]-1H-pyrazol-5-yl}amino)nicotinic acid | 3.06 | 383.2 |
| 20 | 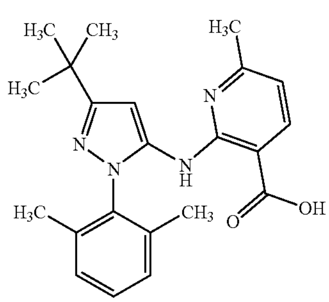 | 2-{[3-tert-butyl-1-(2,6-dimethylphenyl)-1H-pyrazol-5-yl]amino}-6-methylnicotinic acid | 3.78 | 379.2 |

TABLE 1-continued

| Example No | Structure | IUPAC name | LC-MS RT [min] | [M + H]+ |
|---|---|---|---|---|
| 21 | 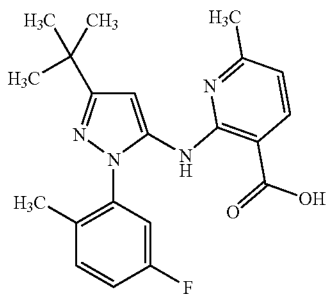 | 2-{[3-tert-butyl-1-(5-fluoro-2-methylphenyl)-1H-pyrazol-5-yl]amino}-6-methylnicotinic acid | 3.58 | 383.2 |
| 22 | 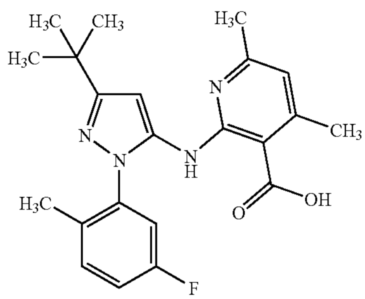 | 2-{[3-tert-butyl-1-(2-chlorophenyl)-1H-pyrazol-5-yl]amino}-o-methylnicotinic acid | 3.78 | 385.2 |
| 23 | 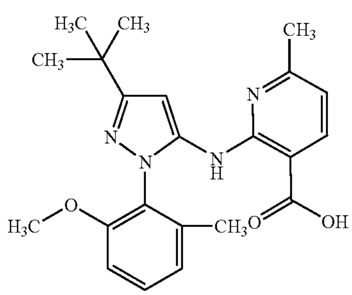 | 2-{[3-tert-butyl-1-(2-methoxy-6-methylphenyl)-1H-pyrazol-5-yl]amino}-6-methylnicotinic acid | 3.57 | 395.2 |
| 24 | 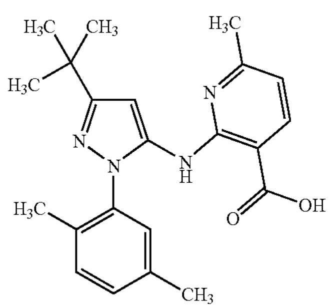 | 2-{[3-tert-butyl-1-(2,5-dimethylphenyl)-1H-pyrazol-5-yl]amino}-6-methylnicotinic acid | 3.50 | 379.2 |
| 25 | 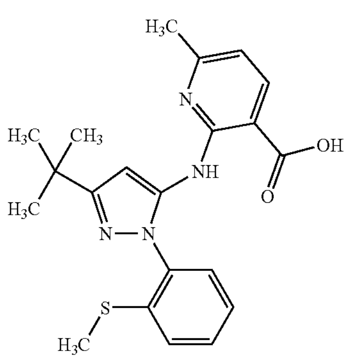 | 2-({3-tert-butyl-1-[2-(methylthio)phenyl]-1H-pyrazol-5-yl}amino)-6-methylnicotinic acid | 3.35 | 397.2 |

TABLE 1-continued

| Example No | Structure | IUPAC name | LC-MS RT [min] | [M + H]+ |
|---|---|---|---|---|
| 26 | 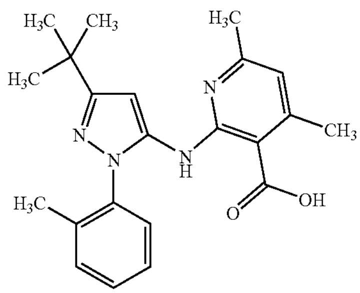 | 2-{[3-tert-butyl-1-(2-methylphenyl)-1H-pyrazol-5-yl]amino}-4,6-dimethylnicotinic acid | 3.30 | 379.2 |
| 27 | 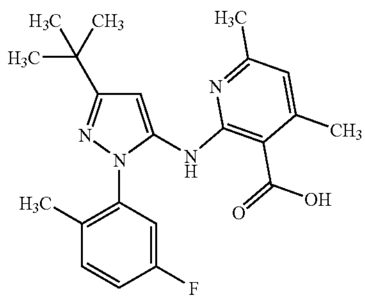 | 2-{[3-tert-butyl-1-(5-fluoro-2-methylphenyl)-1H-pyrazol-5-yl]amino}-4,6-dimethylnicotinic acid | 3.92 | 397.2 |
| 28 | 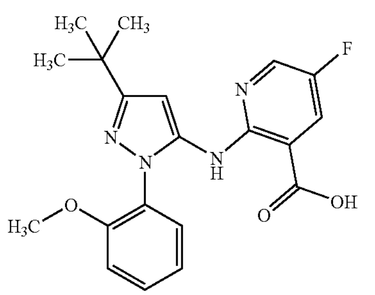 | 2-{[3-tert-butyl-1-(2-methoxyphenyl)-1H-pyrazol-5-yl]amino}-5-fluoronicotinic acid | 3.57 | 385.2 |
| 29 | 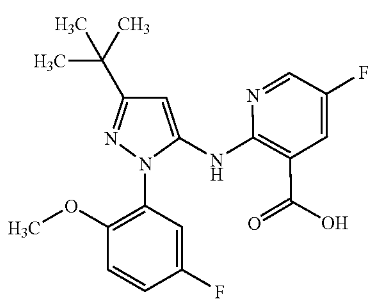 | 2-{[3-tert-butyl-1-(5-fluoro-2-methoxyphenyl)-1H-pyrazol-5-yl]amino}-5-fluoronicotinic acid | 3.77 | 403.2 |
| 30 | 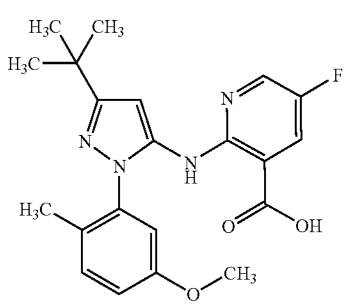 | 2-{[3-tert-butyl-1-(5-methoxy-2-methylphenyl)-1H-pyrazol-5-yl]amino}-5-fluoronicotinic acid | 3.76 | 399.2 |

TABLE 1-continued

| Example No | Structure | IUPAC name | LC-MS RT [min] | [M + H]+ |
|---|---|---|---|---|
| 31 | 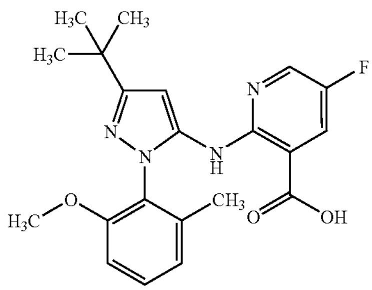 | 2-{[3-tert-butyl-1-(2-methoxy-6-methylphenyl)-1H-pyrazol-5-yl]amino}-5-fluoronicotinic acid | 2.38 | 399.2 |
| 32 | 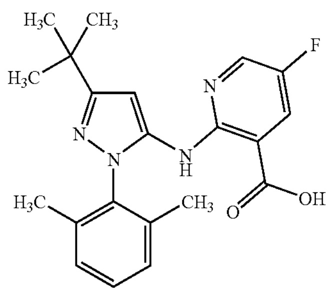 | 2-{[3-tert-butyl-1-(2,6-dimethylphenyl)-1H-pyrazol-5-yl]amino}-5-fluoronicotinic acid | 3.36 | 383.2 |
| 33 | 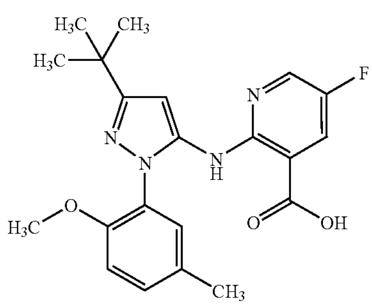 | 2-{[3-tert-butyl-1-(2-methoxy-5-methylphenyl)-1H-pyrazol-5-yl]amino}-5-fluoronicotinic acid | 3.70 | 399.2 |
| 34 | 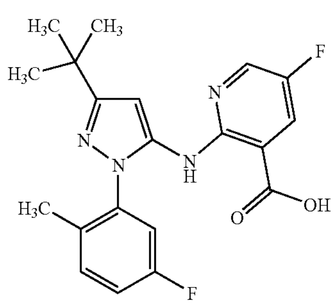 | 2-{[3-tert-butyl-1-(5-fluoro-2-methylphenyl)-1H-pyrazol-5-yl]amino}-5-fluoronicotinic acid | 3.89 | 387.2 |
| 35 | 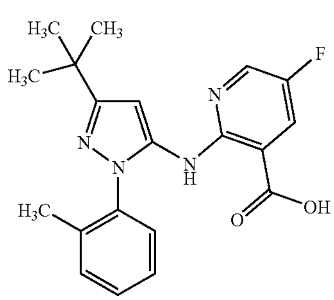 | 2-{[3-tert-butyl-1-(2-methylphenyl)-1H-pyrazol-5-yl]amino}-5-fluoronicotinic acid | 3.69 | 369.2 |

TABLE 1-continued

| Example No | Structure | IUPAC name | LC-MS RT [min] | [M + H]+ |
|---|---|---|---|---|
| 36 | 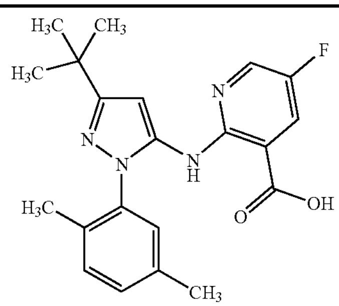 | 2-{[3-tert-butyl-1-(2,5-dimethylphenyl)-1H-pyrazol-5-yl]amino}-5-fluoronicotinic acid | 3.82 | 383.3 |
| 37 | 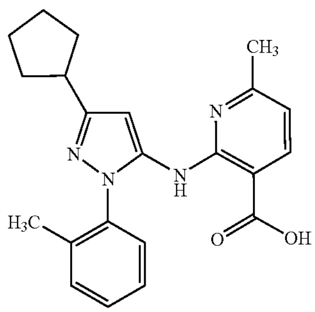 | 2-{[3-cyclopentyl-1-(2-methylphenyl)-1H-pyrazol-5-yl]amino}-6-methylnicotinic acid | 3.76 | 377.2 |
| 38 | 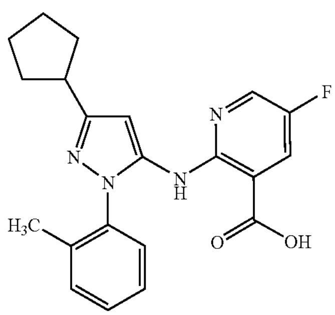 | 2-{[3-cyclopentyl-1-(2-methylphenyl)-1H-pyrazol-5-yl]amino}-5-fluoronicotinic acid | 3.74 | 381.2 |
| 39 | 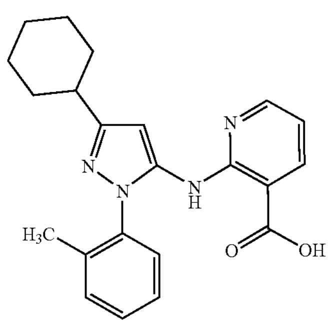 | 2-{[3-cyclohexyl-1-(2-methylphenyl)-1H-pyrazol-5-yl]amino}nicotinic acid | 3.75 | 377.3 |
| 40 | 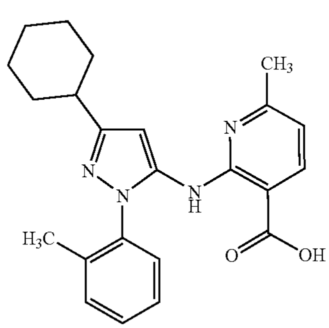 | 2-{[3-cyclohexyl-1-(2-methylphenyl)-1H-pyrazol-5-yl]amino}-6-methylnicotinic acid | 3.93 | 391.3 |

TABLE 1-continued

| Example No | Structure | IUPAC name | LC-MS RT [min] | [M + H]+ |
|---|---|---|---|---|
| 41 | 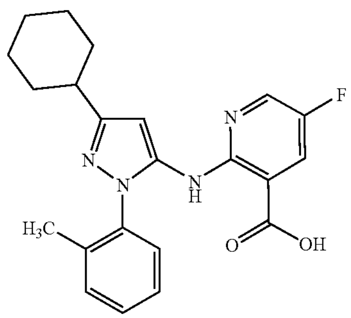 | 2-{[3-cyclohexyl-1-(2-methylphenyl)-1H-pyrazol-5-yl]amino}-5-fluoronicotinic acid | 3.94 | 395.2 |
| 42 | 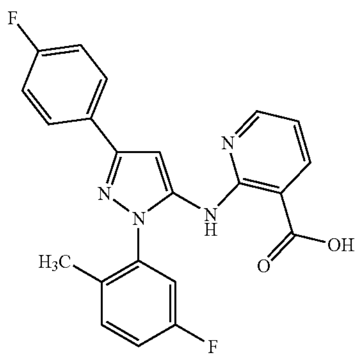 | 2-{[1-(5-fluoro-2-methylphenyl)-3-(4-fluorophenyl)-1H-pyrazol-5-yl]amino}nicotinic acid | 3.58 | 407.1 |
| 43 | 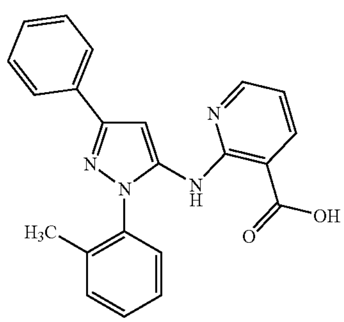 | 2-{[1-(2-methylphenyl)-3-phenyl-1H-pyrazol-5-yl]amino}nicotinic acid | 3.39 | 371.2 |
| 44 | 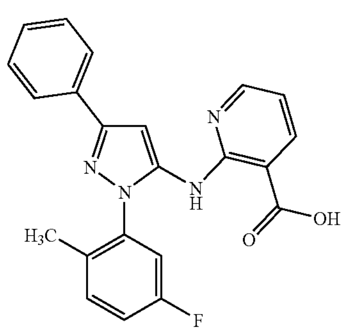 | 2-{[1-(5-fluoro-2-methylphenyl)-3-phenyl-1H-pyrazol-5-yl]amino}nicotinic acid | 3.49 | 389.2 |

TABLE 1-continued

| Example No | Structure | IUPAC name | LC-MS RT [min] | [M + H]+ |
|---|---|---|---|---|
| 45 | 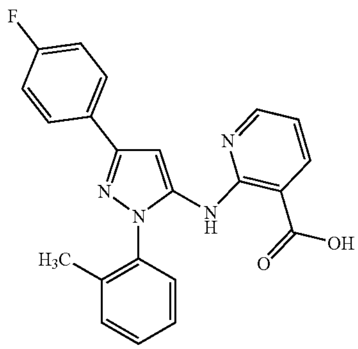 | 2-{[3-(4-fluorophenyl)-1-(2-methylphenyl)-1H-pyrazol-5-yl]amino}nicotinic acid | 3.47 | 389.2 |
| 46 | 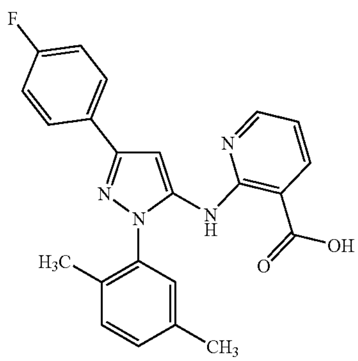 | 2-{[1-(2,5-dimethylphenyl)-3-(4-fluorophenyl)-1H-pyrazol-5-yl]amino}nicotinic acid | 3.63 | 403.1 |
| 47 | 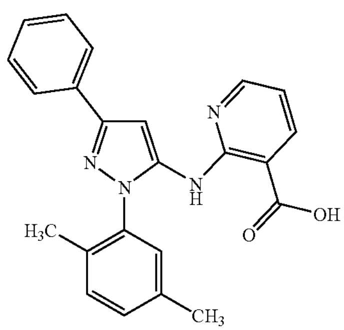 | 2-{[1-(2,5-dimethylphenyl)-3-phenyl-1H-pyrazol-5-yl]amino}nicotinic acid | 3.54 | 385.2 |
| 48 | 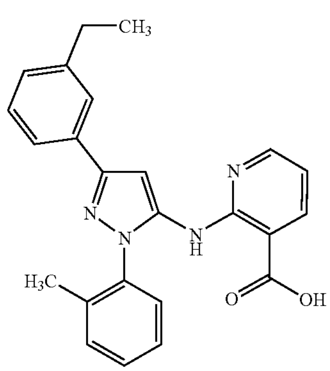 | 2-{[3-(3-ethylphenyl)-1-(2-methylphenyl)-1H-pyrazol-5-yl]amino}nicotinic acid | 3.59 | 399.2 |

TABLE 1-continued

| Example No | Structure | IUPAC name | LC-MS RT [min] | [M + H]+ |
|---|---|---|---|---|
| 49 | 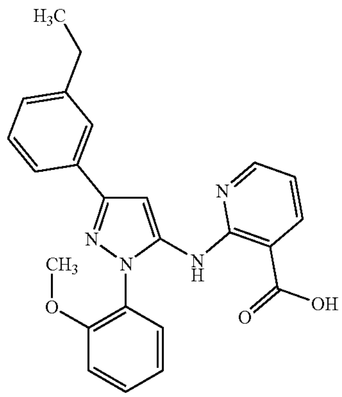 | 2-{[3-(3-ethylphenyl)-1-(2-methoxyphenyl)-1H-pyrazol-5-yl]amino}nicotinic acid | 3.40 | 415.2 |
| 50 | 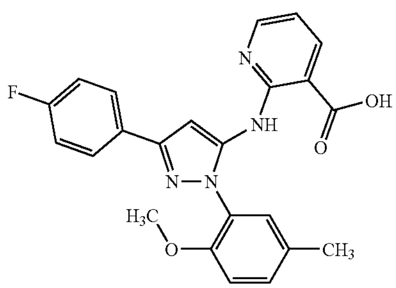 | 2-{[3-(4-fluorophenyl)-1-(2-methoxy-5-methylphenyl)-1H-pyrazol-5-yl]amino}nicotinic acid | 3.03 | 419.1 |
| 51 | 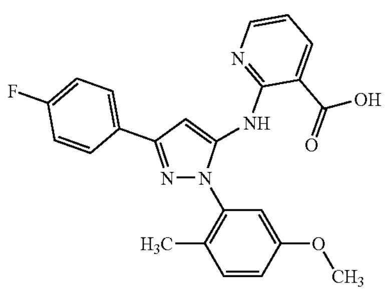 | 2-{[3-(4-fluorophenyl)-1-(5-methoxy-2-methylphenyl)-1H-pyrazol-5-yl]amino}nicotinic acid | 3.33 | 419.2 |
| 52 | 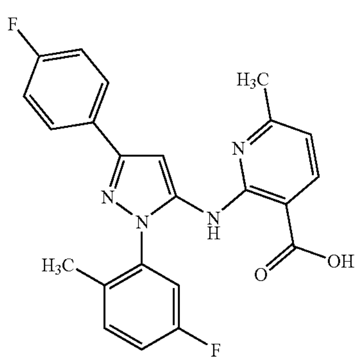 | 2-{[1-(5-fluoro-2-methylphenyl)-3-(4-fluorophenyl)-1H-pyrazol-5-yl]amino}-6-methylnicotinic acid | 3.61 | 421.1 |

TABLE 1-continued

| Example No | Structure | IUPAC name | LC-MS RT [min] | [M + H]+ |
|---|---|---|---|---|
| 53 | 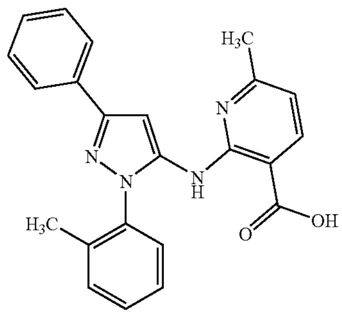 | 6-methyl-2-{[1-(2-methylphenyl)-3-phenyl-1H-pyrazol-5-yl]amino}nicotinic acid | 3.45 | 385.1 |
| 54 | 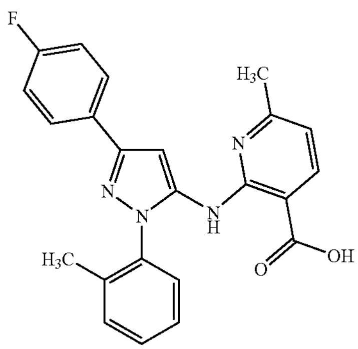 | 2-{[3-(4-fluorophenyl)-1-(2-methylphenyl)-1H-pyrazol-5-yl]amino}-6-methylnicotinic acid | 3.53 | 403.2 |
| 55 | 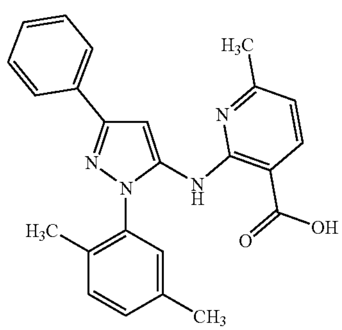 | 2-{[1-(2,5-dimethylphenyl)-3-phenyl-1H-pyrazol-5-yl]amino}-6-methylnicotinic acid | 3.60 | 399.3 |
| 56 | 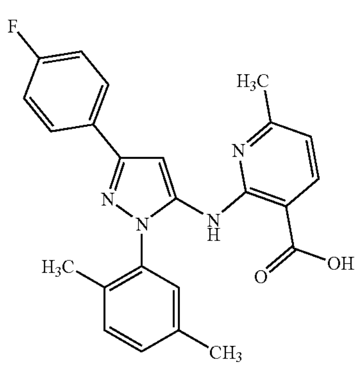 | 2-{[1-(2,5-dimethylphenyl)-3-(4-fluorophenyl)-1H-pyrazol-5-yl]amino}-6-methylnicotinic acid | 3.81 | 417.1 |

TABLE 1-continued

| Example No | Structure | IUPAC name | LC-MS RT [min] | [M + H]⁺ |
|---|---|---|---|---|
| 57 | 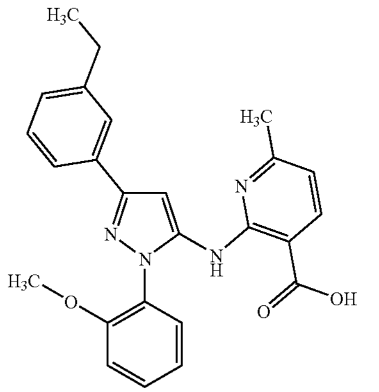 | 2-{[3-(3-ethylphenyl)-1-(2-methoxyphenyl)-1H-pyrazol-5-yl]amino}-6-methylnicotinic acid | 3.54 | 429.2 |
| 58 | 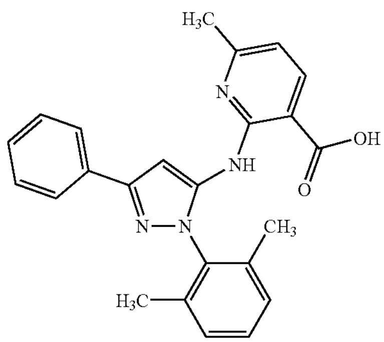 | 2-{[1-(2,6-dimethylphenyl)-3-phenyl-1H-pyrazol-5-yl]amino}-6-methylnicotinic acid | 3.64 | 399.2 |
| 59 | 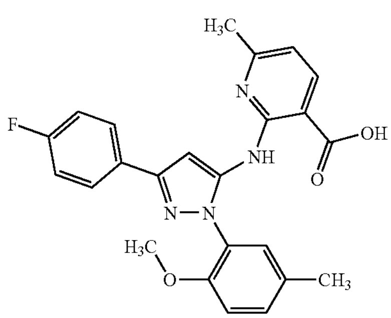 | 2-{[3-(4-fluorophenyl)-1-(2-methoxy-5-methylphenyl)-1H-pyrazol-5-yl]amino}-6-methylnicotinic acid | 3.55 | 433.1 |
| 60 | 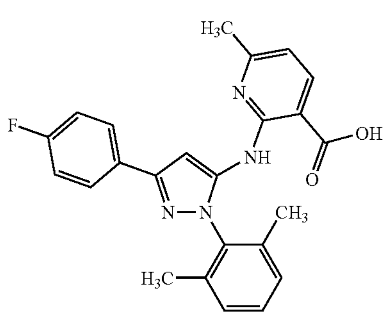 | 2-{[1-(2,6-dimethylphenyl)-3-(4-fluorophenyl)-1H-pyrazol-5-yl]amino}-6-methylnicotinic acid | 3.62 | 417.1 |

TABLE 1-continued

| Example No | Structure | IUPAC name | LC-MS RT [min] | [M + H]+ |
|---|---|---|---|---|
| 61 | 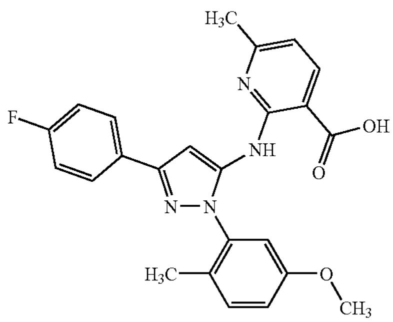 | 2-{[3-(4-fluorophenyl)-1-(5-methoxy-2-methylphenyl)-1H-pyrazol-5-yl]amino}-6-methylnicotinic acid | 3.52 | 433.2 |
| 62 | 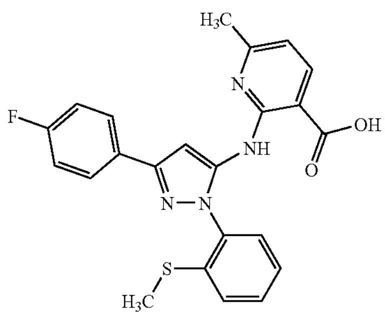 | 2-({3-(4-fluorophenyl)-1-[2-(methylthio)phenyl]-1H-pyrazol-5-yl}amino)-6-methylnicotinic acid | 3.49 | 435.1 |
| 63 | 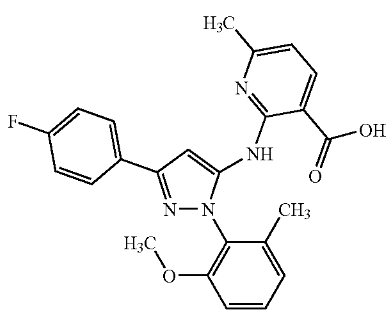 | 2-{[3-(4-fluorophenyl)-1-(2-methoxy-6-methylphenyl)-1H-pyrazol-5-yl]amino}-6-methylnicotinic acid | 3.49 | 433.1 |
| 64 | 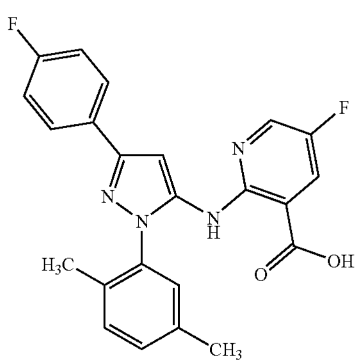 | 2-{[1-(2,5-dimethylphenyl)-3-(4-fluorophenyl)-1H-pyrazol-5-yl]amino}-5-fluoronicotinic acid | 4.10 | 421.2 |

TABLE 1-continued

| Example No | Structure | IUPAC name | LC-MS RT [min] | [M + H]+ |
|---|---|---|---|---|
| 65 | 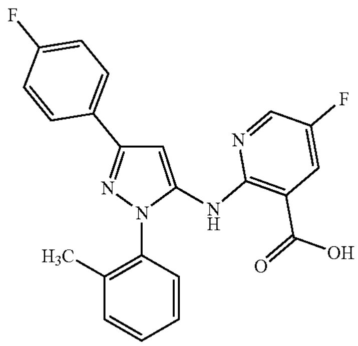 | 5-fluoro-2-{[3-(4-fluorophenyl)-1-(2-methylphenyl)-1H-pyrazol-5-yl]amino}nicotinic acid | 3.96 | 407.2 |
| 66 | 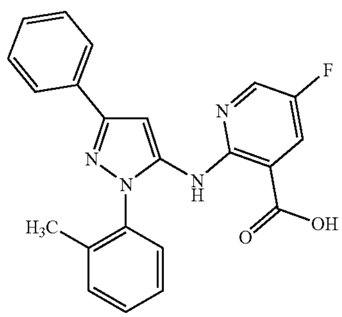 | 5-fluoro-2-{[1-(2-methylphenyl)-3-phenyl-1H-pyrazol-5-yl]amino}nicotinic acid | 3.88 | 389.2 |
| 67 | 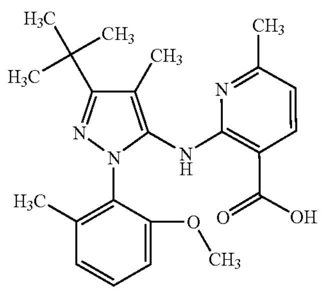 | 2-{[3-tert-butyl-1-(2-methoxy-6-methylphenyl)-4-methyl-1H-pyrazol-5-yl]amino}-6-methylnicotinic acid | 2.79 | 409.2 |
| 68 | 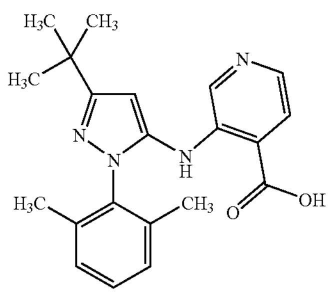 | 3-{[3-tert-butyl-1-(2,6-dimethylphenyl)-1H-pyrazol-5-yl]amino}isonicotinic acid | 2.43 | 365.2 |
| 69 | 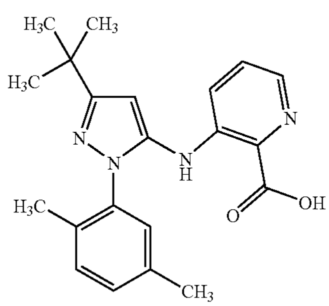 | 3-{[3-tert-butyl-1-(2,5-dimethylphenyl)-1H-pyrazol-5-yl]amino}pyridine-2-carboxylic acid | 3.04 | 321.3 |

TABLE 1-continued

| Example No | Structure | IUPAC name | LC-MS RT [min] | [M + H]+ |
|---|---|---|---|---|
| 70 | 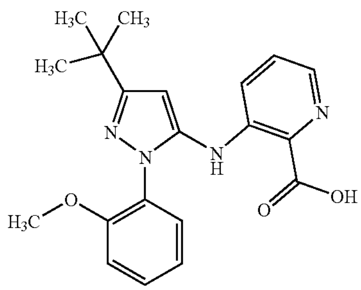 | 3-{[3-tert-butyl-1-(2-methoxyphenyl)-1H-pyrazol-5-yl]amino}pyridine-2-carboxylic acid | 2.46 | 367 |
| 71 | 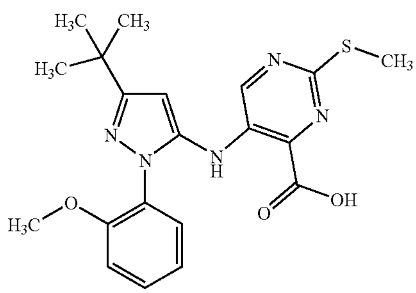 | 5-{[3-tert-butyl-1-(2-methoxyphenyl)-1H-pyrazol-5-yl]amino}-2-(methylthio)pyrimidine-4-carboxylic acid | 3.42 | 413.9 |
| 72 | 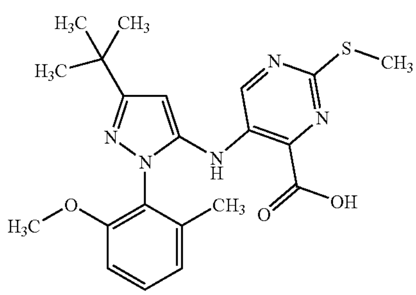 | 5-{[3-tert-butyl-1-(2-methoxy-6-methylphenyl)-1H-pyrazol-5-yl]amino}-2-(methylthio)pyrimidine-4-carboxylic acid | 2.56 | 384.2 |
| 73 | 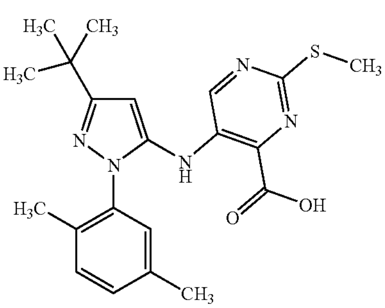 | 5-{[3-tert-butyl-1-(2,5-dimethylphenyl)-1H-pyrazol-5-yl]aminol-2-(methylthio)pyrimidine-4-carboxylic acid | 3.99 | 412 |
| 74 | 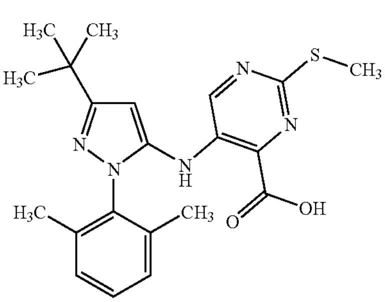 | 5-{[3-tert-butyl-1-(2,6-dimethylphenyl)-1H-pyrazol-5-yl]amino}-2-(methyltio)pyrimidine-4-carboxylic acid | 3.55 | 411.9 |

TABLE 1-continued

| Example No | Structure | IUPAC name | LC-MS RT [min] | [M + H]+ |
|---|---|---|---|---|
| 75 | 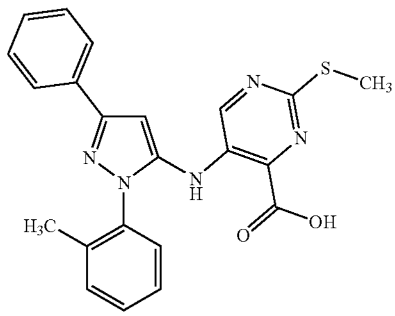 | 5-{[1-(2-methylphenyl)-3-phenyl-1H-pyrazol-5-yl]amino}-2-(methylthio)pyrimidine-4-carboxylic acid | 3.84 | 418 |
| 76 | 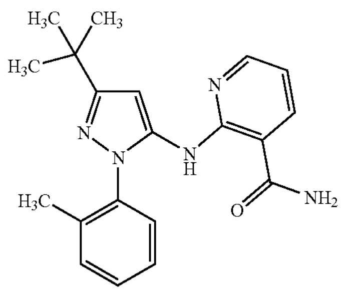 | 2-{[3-tert-butyl-1-(2-methylphenyl)-1H-pyrazol-5-yl]amino}nicotinamide | 2.81 | 350.2 |
| 77 | 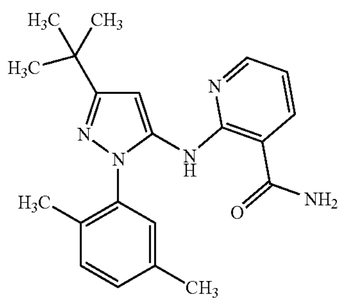 | 2-{[3-tert-butyl-1-(2,5-dimethylphenyl)-1H-pyrazol-5-yl]amino}nicotinamide | 3.36 | 364.2 |
| 78 | 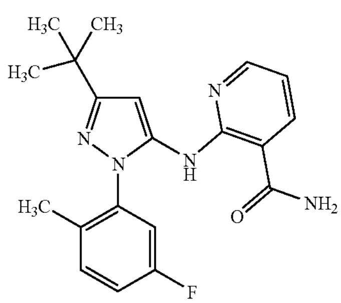 | 2-{[3-tert-butyl-1-(5-fluoro-2-methylphenyl)-1H-pyrazol-5-yl]amino}nicotinamide | 3.48 | 368.2 |
| 79 | 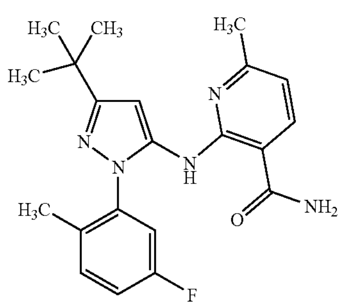 | 2-{[3-tert-butyl-1-(5-fluoro-2-methylphenyl)-1H-pyrazol-5-yl]amino}-6-methylnicotinamide | 3.64 | 382.2 |

TABLE 1-continued

| Example No | Structure | IUPAC name | LC-MS RT [min] | [M + H]+ |
|---|---|---|---|---|
| 80 | 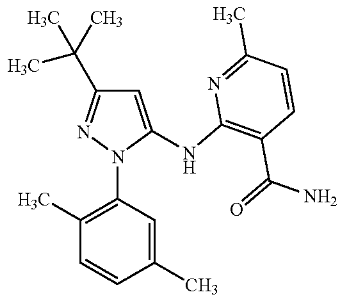 | 2-{[3-tert-butyl-1-(2,5-dimethylphenyl)-1H-pyrazol-5-yl]amino}-6-methylnicotinamide | 3.50 | 378.2 |
| 81 | 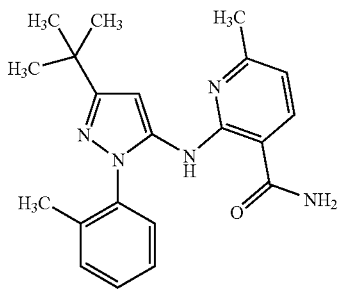 | 2-{(3-tert-butyl-1-(2-methylphenyl)-1H-pyrazol-5-yl]amino}-6-methylnicotinamide | 3.39 | 364.2 |
| 82 | 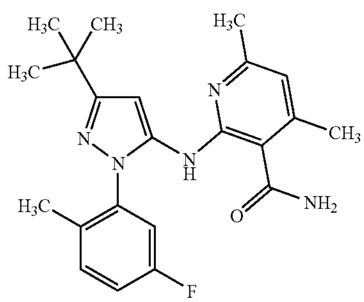 | 2-{[3-tert-butyl-1-(5-fluoro-2-methylphenyl)-1H-pyrazol-5-yl]amino}-4,6-dimethylnicotinamide | 3.38 | 396.2 |
| 83 | 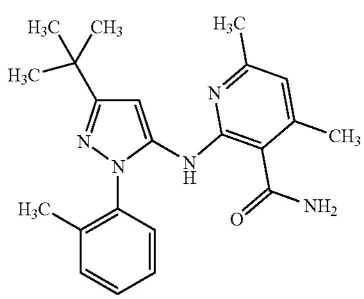 | 2-{[3-tert-butyl-1-(2-methylphenyl)-1H-pyrazol-5-yl]amino}-4,6-dimethylnicotinamide | 3.17 | 378.2 |
| 84 | 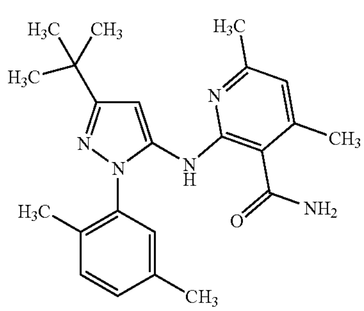 | 2-{[3-tert-butyl-1-(2,5-dimethylphenyl)-1H-pyrazol-5-yl]amino}-4,6-dimethylnicotinamide | 3.31 | 392.2 |

TABLE 1-continued
| Example No | Structure | IUPAC name | LC-MS RT [min] | [M + H]+ |
|---|---|---|---|---|
| 85 | 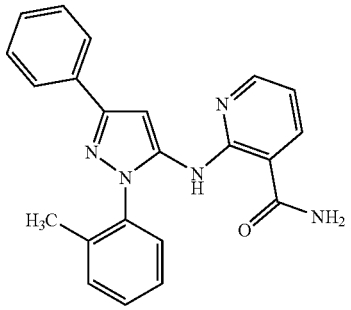 | 2-{[1-(2-methylphenyl)-3-phenyl-1H-pyrazol-5-yl]amino}nicotinamide | 3.52 | 370.2 |
| 86 | 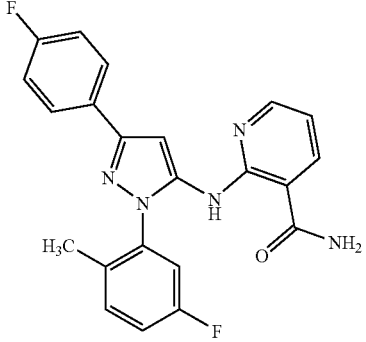 | 2-{[1-(5-fluoro-2-methylphenyl)-3-(4-fluorophenyl)-1H-pyrazol-5-yl]amino}nicotinamide | 3.73 | 406.2 |
| 87 | 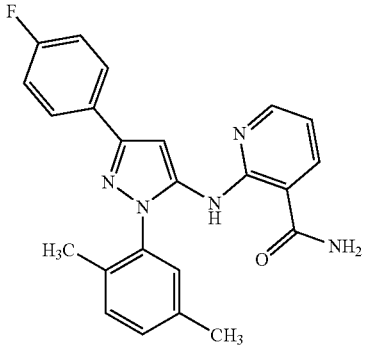 | 2-{[1-(2,5-dimethylphenyl)-3-(4-fluorophenyl)-1H-pyrazol-5-yl]amino}nicotinamide | 3.77 | 402.2 |
| 88 | 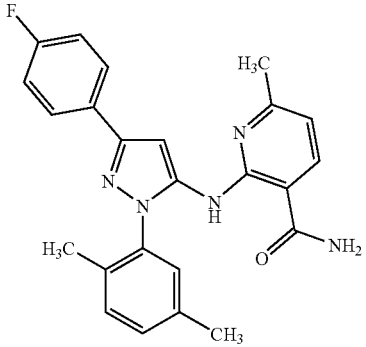 | 2-{[1-(2,5-dimethylphenyl)-3-(4-fluorophenyl)-1H-pyrazol-5-yl]amino}-6-methylnicotinamide | 3.92 | 416.2 |

TABLE 1-continued

| Example No | Structure | IUPAC name | LC-MS RT [min] | [M + H]+ |
|---|---|---|---|---|
| 89 | 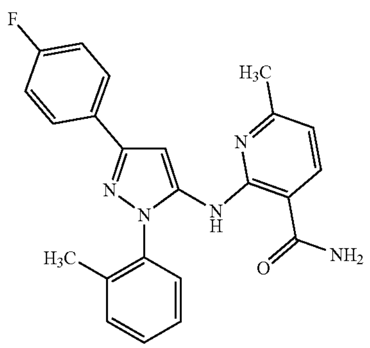 | 2-{[3-(4-fluorophenyl)-1-(2-methylphenyl)-1H-pyrazol-5-yl]amino}-6-methylnicotinamide | 3.77 | 402.2 |
| 90 | 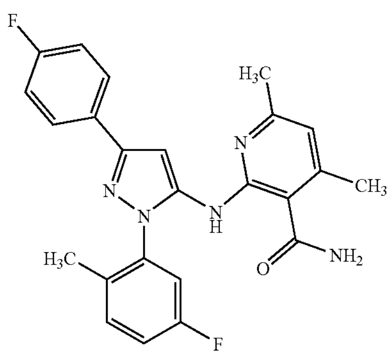 | 2-{[1-(5-fluoro-2-methylphenyl)-3-(4-fluorophenyl)-1H-pyrazol-5-yl]amino}-4,6-dimethylnicotinamide | 3.22 | 434.2 |
| 91 | 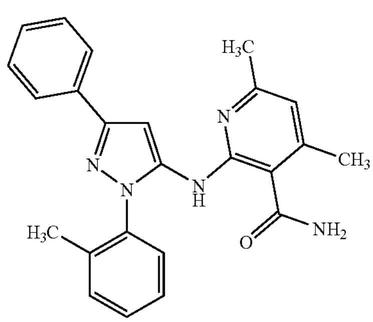 | 4,6-dimethyl-2-{[1-(2-methylphenyl)-3-phenyl-1H-pyrazol-5-yl]amino}nicotinamide | 2.96 | 398.2 |
| 92 | 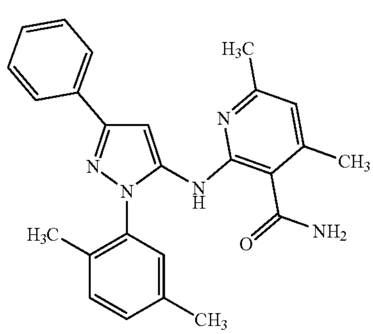 | 2-{[1-(2,5-dimethylphenyl)-3-phenyl-1H-pyrazol-5-yl]amino}-4,6-dimethylnicotinamide | 3.13 | 412.2 |

TABLE 1-continued

| Example No | Structure | IUPAC name | LC-MS RT [min] | [M + H]+ |
|---|---|---|---|---|
| 93 | 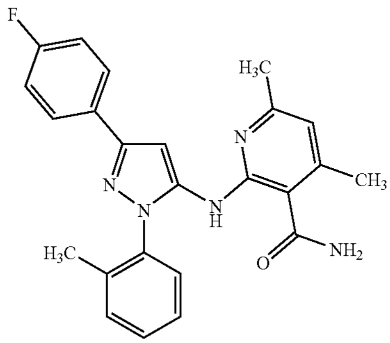 | 2-{[3-(4-fluorophenyl)-1-(2-methylphenyl)-1H-pyrazol-5-yl]amino}-4,6-dimethylnicotinamide | 3.14 | 416.1 |
| 94 | 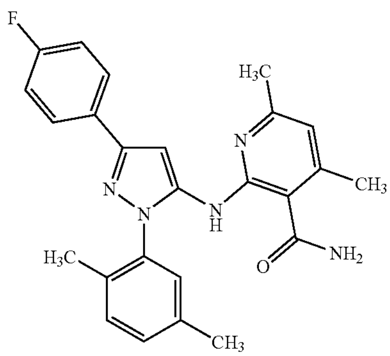 | 2-{[1-(2,5-dimethylphenyl)-3-(4-fluorophenyl)-1H-pyrazol-5-yl]amino}-4,6-dimethylnicotinamide | 3.71 | 430.2 |
| 95 | 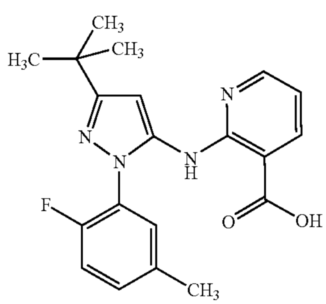 | 2-{[3-tert-butyl-1-(2-fluoro-5-methylphenyl)-1H-pyrazol-5-yl]amino}nicotinic acid | 3.08 | 369.2 |
| 96 | 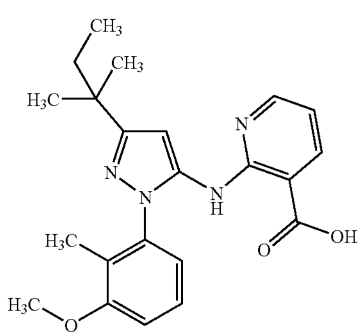 | 2-{[3-(1,1-dimethylpropyl)-1-(3-methoxy-2-methylphenyl)-1H-pyrazol-5-yl]amino}nicotinic acid | 3.75 | 395.3 |

TABLE 1-continued

| Example No | Structure | IUPAC name | LC-MS RT [min] | [M + H]+ |
|---|---|---|---|---|
| 97 | 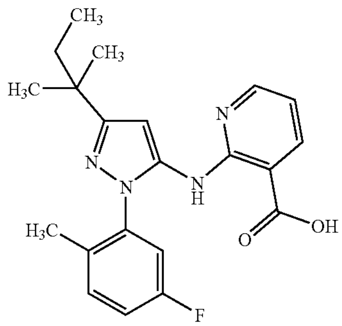 | 2-{[3-(1,1-dimethylpropyl)-1-(5-fluoro-2-methylphenyl)-1H-pyrazol-5-yl]amino}nicotinic acid | 3.87 | 383.2 |
| 98 | 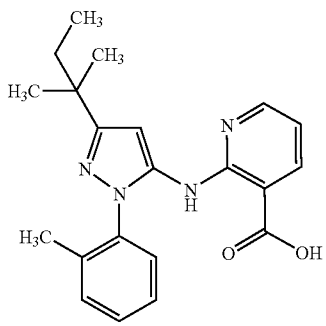 | 2-{[3-(1,1-dimethylpropyl)-1-(2-methylphenyl)-1H-pyrazol-5-yl]amino}nicotinic acid | 3.70 | 365.2 |
| 99 | 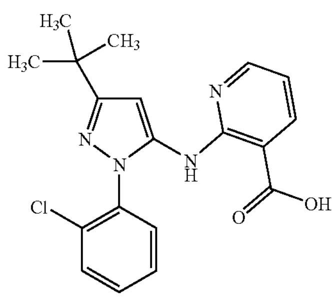 | 2-{[3-tert-butyl-1-(2-chlorophenyl)-1H-pyrazol-5-yl]amino}nicotinic acid | 3.58 | 371.2 |
| 100 | 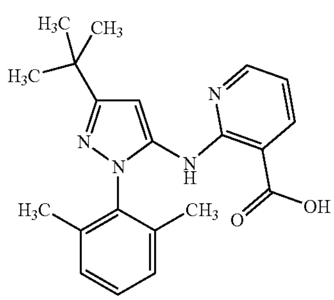 | 2-{[3-tert-butyl-1-(2,6-dimethylphenyl)-1H-pyrazol-5-yl]amino}nicotinic acid | 3.64 | 365.2 |
| 101 | 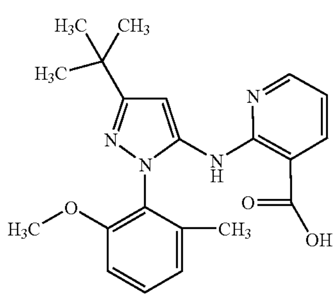 | 2-{[3-tert-butyl-1-(2-methoxy-6-methylphenyl)-1H-pyrazol-5-yl]amino}nicotinic acid | 3.39 | 381.3 |

TABLE 1-continued

| Example No | Structure | IUPAC name | LC-MS RT [min] | [M + H]+ |
|---|---|---|---|---|
| 102 | 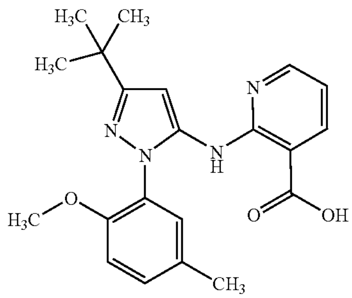 | 2-{[3-tert-butyl-1-(2-methoxy-5-methylphenyl)-1H-pyrazol-5-yl]amino}nicotinic acid | 3.49 | 381.2 |
| 103 | 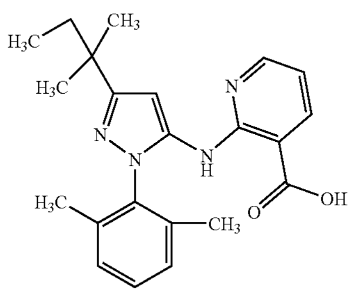 | 2-{[1-(2,6-dimethylphenyl)-3-(1,1-dimethylpropyl)-1H-pyrazol-5-yl]amino}nicotinic acid | 3.42 | 379.2 |
| 104 | 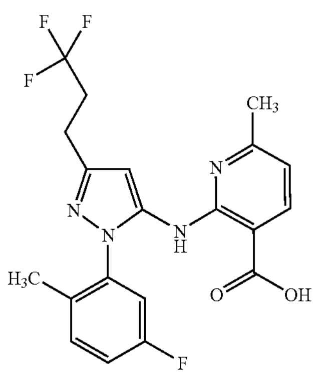 | 2-{[1-(5-fluoro-2-methylphenyl)-3-(3,3,3-trifluoropropyl)-1H-pyrazol-5-yl]amino}-6-methylnicotinic acid | 3.34 | 423.2 |
| 105 | 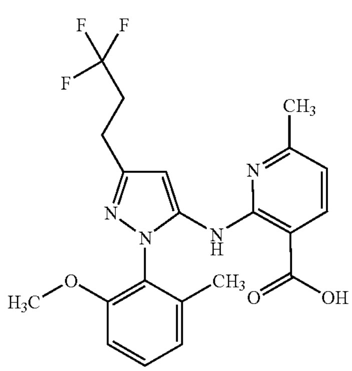 | 2-{[1-(2-methoxy-6-methylphenyl)-3-(3,3,3-trifluoropropyl)-1H-pyrazol-5-yl]amino}-6-methylnicotinic acid | 3.17 | 435.1 |

TABLE 1-continued

| Example No | Structure | IUPAC name | LC-MS RT [min] | [M + H]+ |
|---|---|---|---|---|
| 106 | 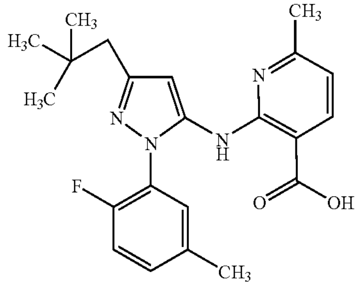 | 2-{[3-(2,2-dimethylpropyl)-1-(2-fluoro-5-methylphenyl)-1H-pyrazol-5-yl]aminol-6-methylnicotinic acid | 3.32 | 397.1 |
| 107 | 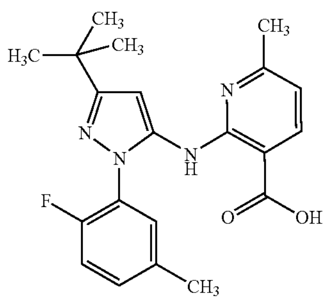 | 2-{[3-tert-butyl-1-(2-fluoro-5-methylphenyl)-1H-pyrazol-5-yl]amino}-6-methylnicotinic acid | 3.36 | 383.1 |
| 108 | 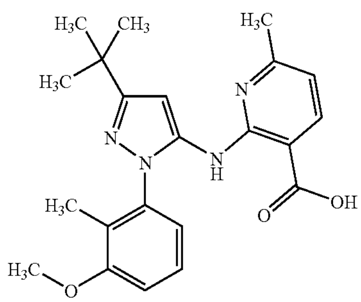 | 2-{[3-tert-butyl-1-(3-methoxy-2-methylphenyl)-1H-pyrazol-5-yl]amino}-6-methylnicotinic acid | 3.78 | 395.2 |
| 109 | 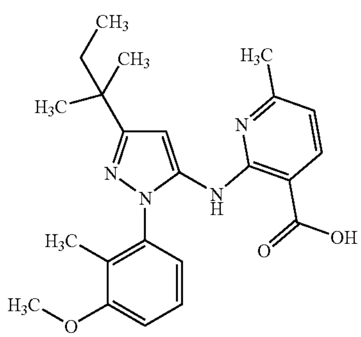 | 2-{[3-(1,1-dimethylpropyl)-1-(3-methoxy-2-methylphenyl)-1H-pyrazol-5-yl]amino}-6-methylnicotinic acid | 3.92 | 409.3 |
| 110 | 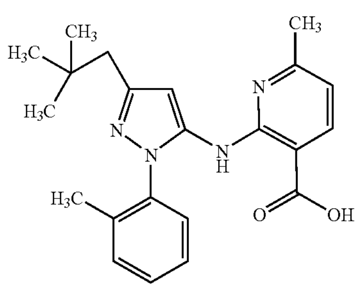 | 2-{[3-(2,2-dimethylpropyl)-1-(2-methylphenyl)-1H-pyrazol-5-yl]amino}-6-methylnicotinic acid; | 3.84 | 379.3 |

TABLE 1-continued

| Example No | Structure | IUPAC name | LC-MS RT [min] | [M + H]+ |
|---|---|---|---|---|
| 111 | 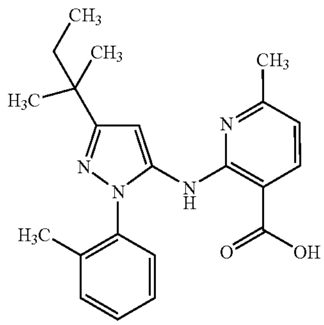 | 2-{[3-(1,1-dimethylpropyl)-1-(2-methylphenyl)-1H-pyrazol-5-yl]amino}-6-methylnicotinic acid | 3.87 | 379.3 |
| 112 | 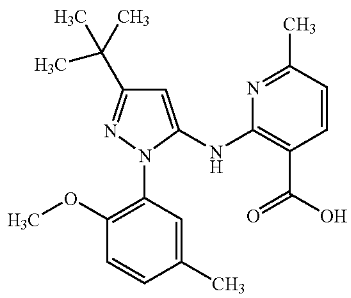 | 2-{[3-tert-butyl-1-(2-methoxy-5-methylphenyl)-1H-pyrazol-5-yl]amino}-6-methylnicotinic acid | 3.68 | 395.3 |
| 113 | 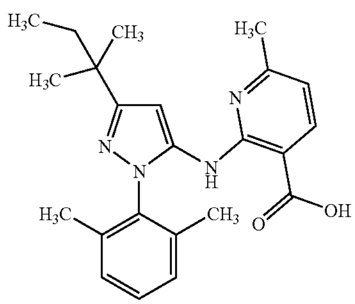 | 2-{[1-(2,6-dimethylphenyl)-3-(1,1-dimethylpropyl)-1H-pyrazol-5-yl]amino}-6-methylnicotinic acid | 3.62 | 393.3 |
| 114 | 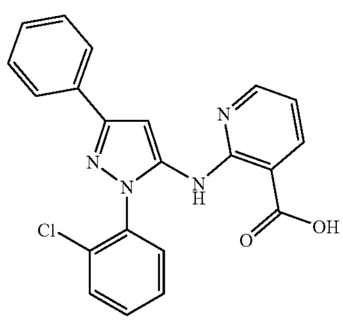 | 2-{[1-(2-chlorophenyl)-3-phenyl-1H-pyrazol-5-yl]amino}nicotinic acid | 3.69 | 391.2 |
| 115 | 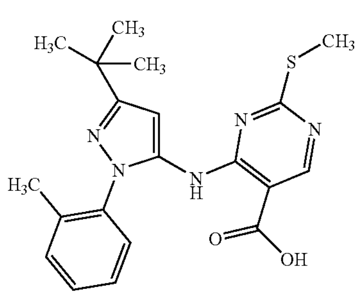 | 4-{[3-tert-butyl-1-(2-methylphenyl)-1H-pyrazol-5-yl]amino}-2-(methylthio)pyrimidine-5-carboxylic acid | 3.77 | 398.1 |

TABLE 1-continued

| Example No | Structure | IUPAC name | LC-MS RT [min] | [M + H]+ |
|---|---|---|---|---|
| 116 | 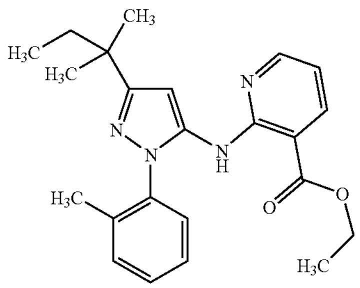 | ethyl 2-{[3-(1,1-dimethylpropyl)-1-(2-methylphenyl)-1H-pyrazol-5-yl]amino]nicotinate | 4.37 | 393.3 |
| 117 | 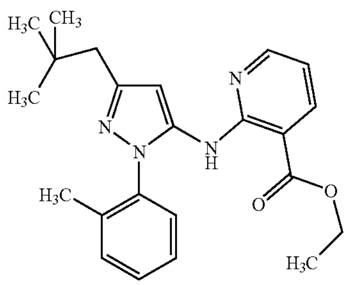 | ethyl 2-{[3-(2,2-dimethylpropyl)-1-(2-methylphenyl)-1H-pyrazol-5-yl]amino}nicotinate | 4.33 | 393.3 |
| 118 | 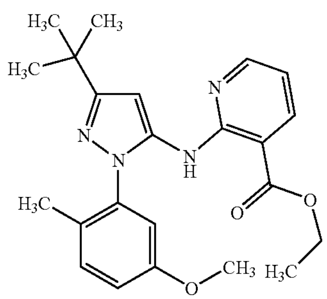 | ethyl 2-{[3-tert-butyl-1-(5-methoxy-2-methylphenyl)-1H-pyrazol-5-yl]amino}nicotinate | 4.23 | 409.2 |
| 119 | 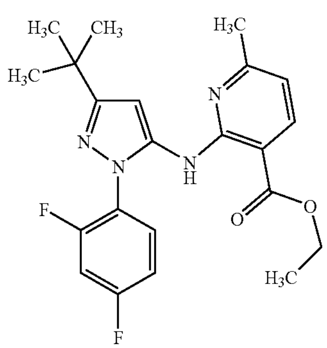 | ethyl 2-{[3-tert-butyl-1-(2,4-difluorophenyl)-1H-pyrazol-5-yl]amino}-6-methylnicotinate | 4.01 | 415.2 |
| 120 | 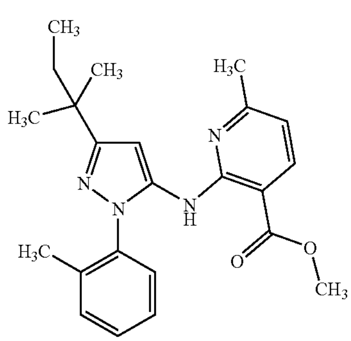 | methyl 2-{[3-(1,1-dimethylpropyl)-1-(2-methylphenyl)-1H-pyrazol-5-yl]amino}-6-methylnicotinate | 4.37 | 393.3 |

TABLE 1-continued

| Example No | Structure | IUPAC name | LC-MS RT [min] | [M + H]+ |
|---|---|---|---|---|
| 121 | 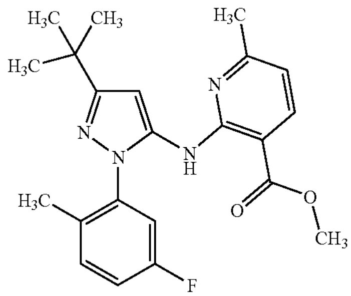 | methyl 2-{[3-tert-butyl-1-(5-fluoro-2-methylphenyl)-1H-pyrazol-5-yl]amino}-6-methylnicotinate | 4.39 | 397.2 |
| 122 | 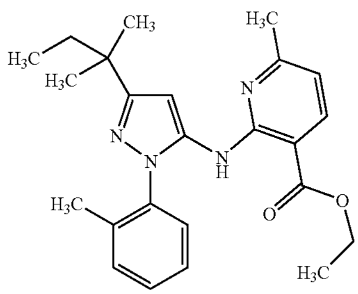 | ethyl 2-{[3-(1,1-dimethylpropyl)-1-(2-methylphenyl)-1H-pyrazol-5-yl]amino}-6-methylnicotinate | 4.55 | 407.3 |
| 123 | 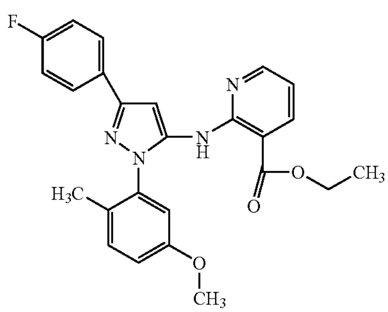 | ethyl 2-{[3-(4-fluorophenyl)-1-(5-methoxy-2-methylphenyl)-1H-pyrazol-5-yl]amino}nicotinate; | 4.46 | 447.2 |
| 124 | 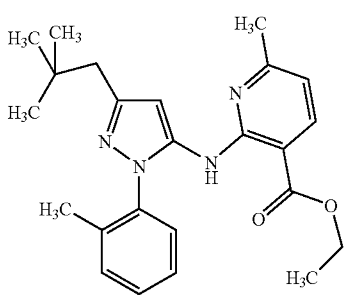 | ethyl 2-{[3-(2,2-dimethylpropyl)-1-(2-methylphenyl)-1H-pyrazol-5-yl]amino}-6-methylnicotinate | 4.50 | 407.3 |
| 125 | 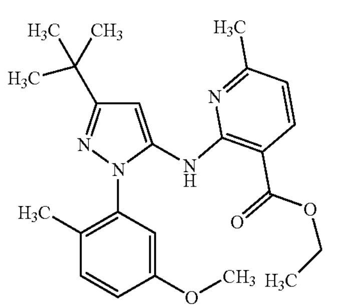 | ethyl 2-{[3-tert-butyl-1-(5-methoxy-2-methylphenyl)-1H-pyrazol-5-yl]amino}-6-methylnicotinate | 4.43 | 423.3 |

TABLE 1-continued

| Example No | Structure | IUPAC name | LC-MS RT [min] | [M + H]+ |
|---|---|---|---|---|
| 126 | 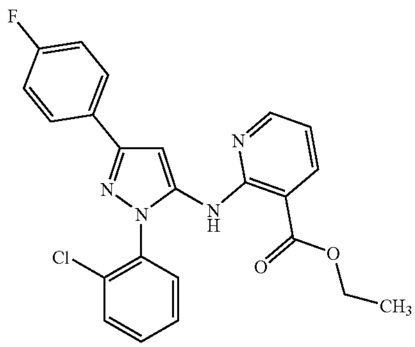 | ethyl 2-{[1-(2-chlorophenyl)-3-(4-fluorophenyl)-1H-pyrazol-5-yl]amino}nicotinate | 4.38 | 437.2 |
| 127 | 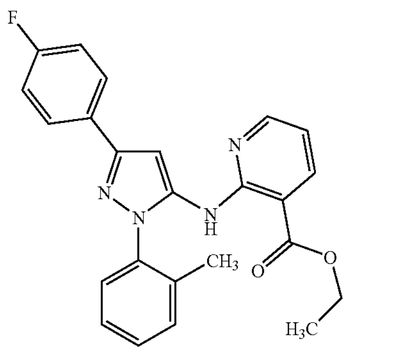 | ethyl 2-{[3-(4-fluorophenyl)-1-(2-methylphenyl)-1H-pyrazol-5-yl]amino}nicotinate | 4.30 | 417.2 |
| 128 | 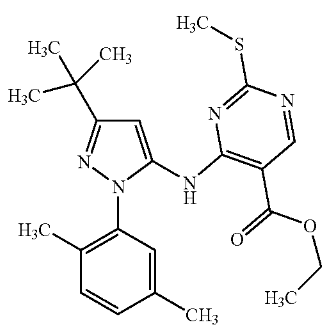 | ethyl 4-{[3-tert-butyl-1-(2,5-dimethylphenyl)-1H-pyrazol-5-yl]amino}-2-(methylthio)pyrimidine-5-carboxylate | 4.66 | 440.2 |
| 129 | 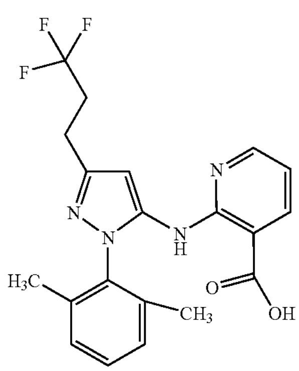 | 2-{[1-(2,6-dimethylphenyl)-3-(3,3,3-trifluoropropyl)-1H-pyrazol-5-yl]amino}nicotinic acid; | 3.28 | 405.1 |

TABLE 1-continued

| Example No | IUPAC name | LC-MS RT [min] | [M + H]+ |
|---|---|---|---|
| 130 | 2-{[3-(1,1-dimethylpropyl)-1-(2-methoxy-6-methylphenyl)-1H-pyrazol-5-yl]amino}nicotinic acid; | 3.16 | 395.2 |
| 131 | 2-{[3-(1,1-dimethylpropyl)-1-(2-methoxy-5-methylphenyl)-1H-pyrazol-5-yl]amino}nicotinic acid; | 3.23 | 395.2 |
| 132 | 2-{[3-(1,1-dimethylpropyl)-1-(2-methoxy-5-methylphenyl)-1H-pyrazol-5-yl]amino}-6-methylnicotinic acid; | 3.42 | 409.2 |
| 133 | 2-{[3-(1,1-dimethylpropyl)-1-(2-methoxyphenyl)-1H-pyrazol-5-yl]amino}nicotinic acid; | 3.07 | 381.2 |
| 134 | 2-{[3-(1,1-dimethylpropyl)-1-(2-ethylphenyl)-1H-pyrazol-5-yl]amino}nicotinic acid; | 3.35 | 379.2 |

TABLE 1-continued

| Example No | Structure | IUPAC name | LC-MS RT [min] | [M + H]+ |
|---|---|---|---|---|
| 135 | 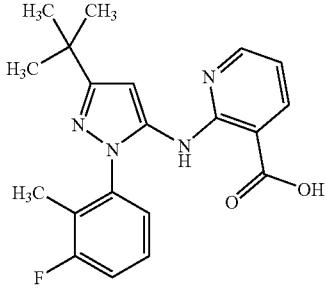 | 2-{[3-tert-butyl-1-(3-fluoro-2-methylphenyl)-1H-pyrazol-5-yl]amino}nicotinic acid; | 3.15 | 369.2 |
| 136 | 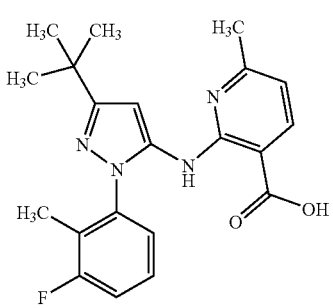 | 2-{[3-tert-butyl-1-(3-fluoro-2-methylphenyl)-1H-pyrazol-5-yl]amino}-6-methylnicotinic acid; | 3.42 | 383.1 |
| 137 | 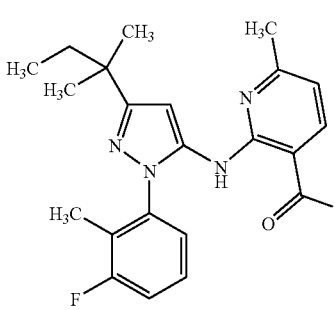 | 2-{[3-(1,1-dimethylpropyl)-1-(3-fluoro-2-methylphenyl)-1H-pyrazol-5-yl]amino}-6-methylnicotinic acid; | 3.37 | 397.1 |
| 138 | 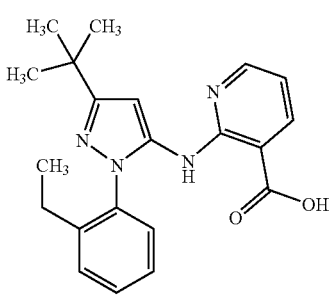 | 2-{[3-tert-butyl-1-(2-ethylphenyl)-1H-pyrazol-5-yl]amino}nicotinic acid; | 3.29 | 365.2 |
| 139 | 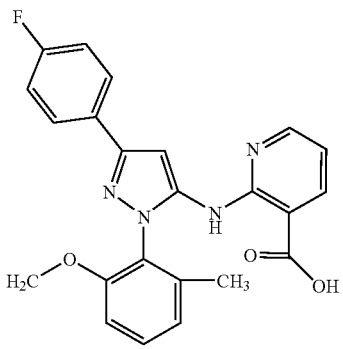 | 2-{[3-(4-fluorophenyl)-1-(2-methoxy-6-methylphenyl)-1H-pyrazol-5-yl]amino}nicotinic acid; | 3.44 | 419.2 |

TABLE 1-continued

| Example No | Structure | IUPAC name | LC-MS RT [min] | [M + H]+ |
|---|---|---|---|---|
| 140 | 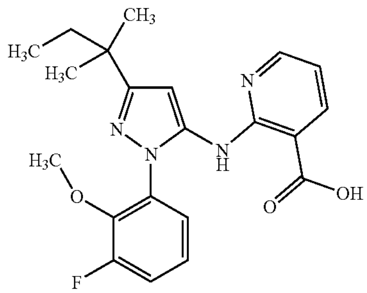 | 2-{[3-(1,1-dimethylpropyl)-1-(3-fluoro-2-methoxyphenyl)-1H-pyrazol-5-yl]amino}nicotinic acid; | 3.73 | 399.2 |
| 141 | 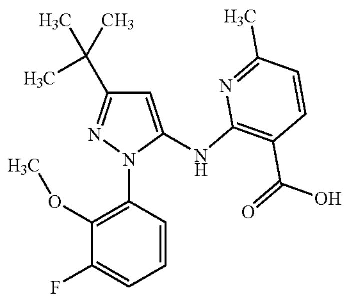 | 2-{[3-tert-butyl-1-(3-fluoro-2-methoxyphenyl)-1H-pyrazol-5-yl]amino}-6-methylnicotinic acid; | 3.78 | 399.2 |
| 142 | 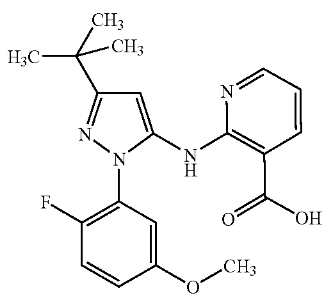 | 2-{[3-(1,1-dimethylpropyl)-1-(2-fluoro-5-methoxyphenyl)-1H-pyrazol-5-yl]amino}nicotinic acid | 3.79 | 399.2 |
| 143 | 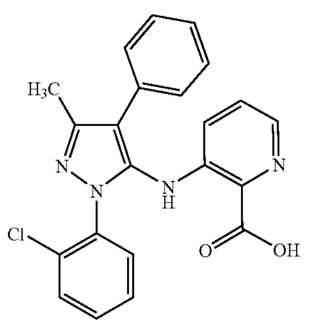 | 3-{[1-(2-chlorophenyl)-3-methyl-4-phenyl-1H-pyrazol-5-yl]amino}pyridine-2-carboxylic acid; | 2.85 | 405 |
| 144 | 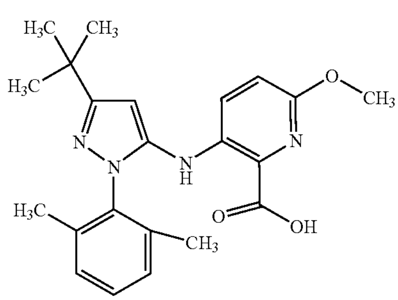 | 3-{[3-tert-butyl-1-(2,6-dimethylphenyl)-1H-pyrazol-5-yl]amino}-6-methoxypyridine-2-carboxylic acid; | 3.6 | 395 |

TABLE 1-continued

| Example No | Structure | IUPAC name | LC-MS RT [min] | [M + H]+ |
| --- | --- | --- | --- | --- |
| 145 | 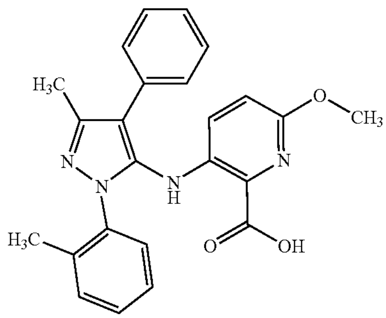 | 6-methoxy-3-{[3-methyl-1-(2-methylphenyl)-4-phenyl-1H-pyrazol-5-yl]amino}pyridine-2-carboxylic acid; | 3.36 | 415 |
| 146 | 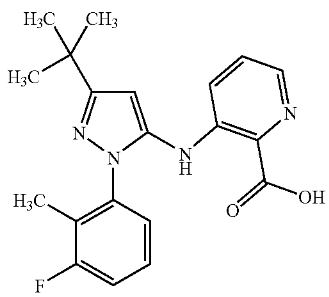 | 3-{[3-tert-butyl-1-(3-fluoro-2-methylphenyl)-1H-pyrazol-5-yl]amino}pyridine-2-carboxylic acid; | 2.62 | 369 |
| 147 | 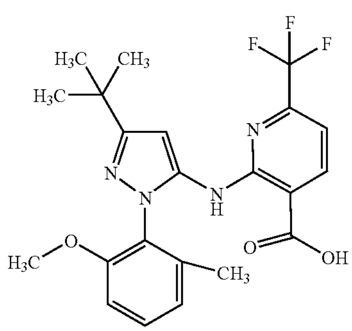 | 2-{[3-tert-butyl-1-(2-methoxy-6-methylphenyl)-1H-pyrazol-5-yl]amino}-6-(trifluoromethyl)nicotinic acid; | 3.58 | 449.2 |
| 148 | 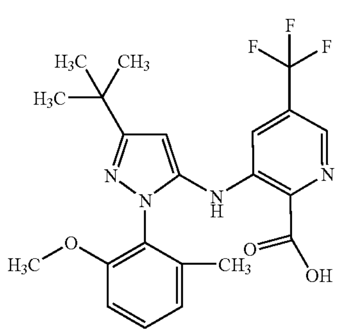 | 3-{[3-tert-butyl-1-(2-methoxy-6-methylphenyl)-1H-pyrazol-5-yl]amino}-5-(trifluoromethyl)pyridine-2-carboxylic acid; | 3.64 | 449 |

TABLE 1-continued

| Example No | Structure | IUPAC name | LC-MS RT [min] | [M + H]⁺ |
|---|---|---|---|---|
| 149 | 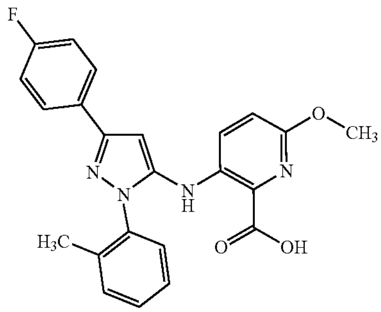 | 3-{[3-(4-fluorophenyl)-1-(2-methylphenyl)-1H-pyrazol-5-yl]amino}-6-methoxypyridine-2-carboxylic acid; | 3.65 | 419 |
| 150 | 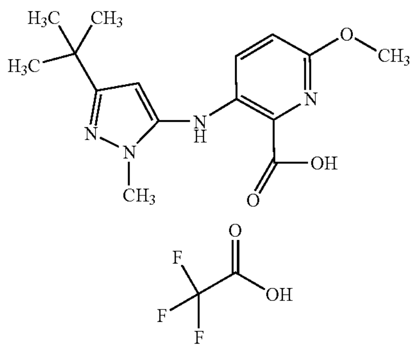 | 3-[(3-tert-butyl-1-methyl-1H-pyrazol-5-yl)amino]-6-methoxypyridine-2-carboxylic acid trifluoroacetate; | 2.63 | 305 |
| 151 | 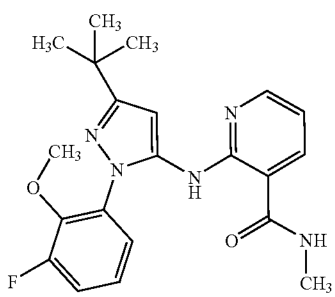 | 2-{[3-tert-butyl-1-(3-fluoro-2-methoxyphenyl)-1H-pyrazol-5-yl]amino}-N-methylnicotinamide; | 3.46 | 398.3 |
| 152 | 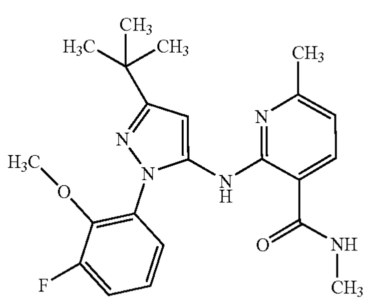 | 2-{[3-tert-butyl-1-(3-fluoro-2-methoxyphenyl)-1H-pyrazol-5-yl]amino}-N,6-dimethylnicotinamide; | 3.64 | 412.3 |

TABLE 1-continued

| Example No | Structure | IUPAC name | LC-MS RT [min] | [M + H]+ |
|---|---|---|---|---|
| 153 | 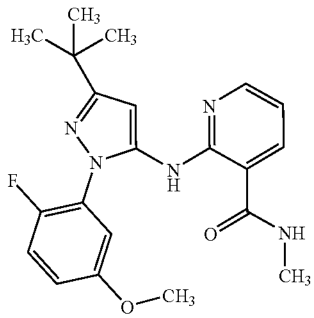 | 2-{[3-tert-butyl-1-(2-fluoro-5-methoxyphenyl)-1H-pyrazol-5-yl]amino}-N-methylnicotinamide | 3.51 | 398.3 |
| 154 | 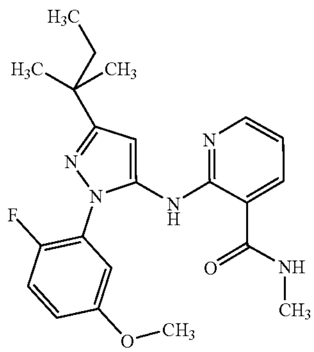 | 2-{[3-(1,1-dimethylpropyl)-1-(2-fluoro-5-methoxyphenyl)-1H-pyrazol-5-yl]amino}-N-methylnicotinamide; | 3.71 | 412.3 |
| 155 | 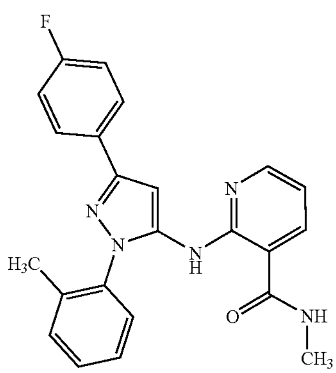 | 2-{[3-(4-fluorophenyl)-1-(2-methylphenyl)-1H-pyrazol-5-yl]amino}-N-methylnicotinamide; | 3.76 | 402.2 |
| 156 | 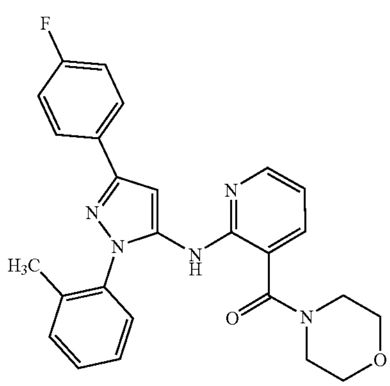 | N-[3-(4-fluorophenyl)-1-(2-methylphenyl)-1H-pyrazol-5-yl]-3-(morpholin-4-ylcarbonyl)pyridin-2-amine; | 3.61 | 458.2 |

TABLE 1-continued

| Example No | Structure | IUPAC name | LC-MS RT [min] | [M + H]+ |
|---|---|---|---|---|
| 157 | 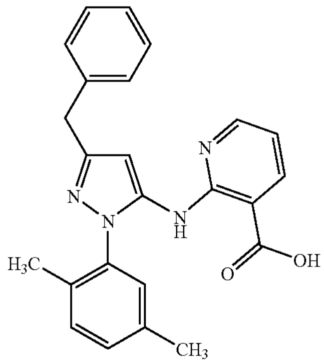 | 2-{[3-benzyl-1-(2,5-dimethylphenyl)-1H-pyrazol-5-yl]amino}nicotinic acid | | |
| 158 | 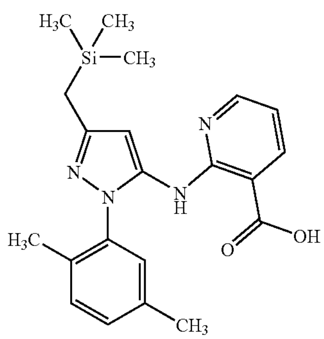 | 2-({1-(2,5-dimethylphenyl)-3-[(trimethylsilyl)methyl]-1H-pyrazol-5-yl}amino)nicotinic acid | | |
| 159 | 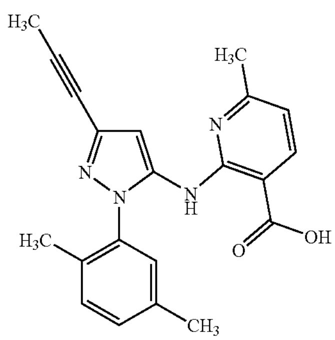 | 2-{[1-(2,5-dimethylphenyl)-3-prop-1-yn-1-yl-1H-pyrazol-5-yl]amino}-6-methylnicotinic acid | | |
| 160 | 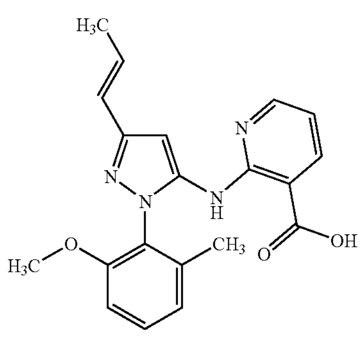 | 2-({1-(2-methoxy-6-methylphenyl)-3-[(1E)-prop-1-en-1-yl]-1H-pyrazol-5-yl}amino)nicotinic acid | | |

TABLE 1-continued

| Example No | Structure | IUPAC name | LC-MS RT [min] | [M + H]+ |
|---|---|---|---|---|
| 161 | 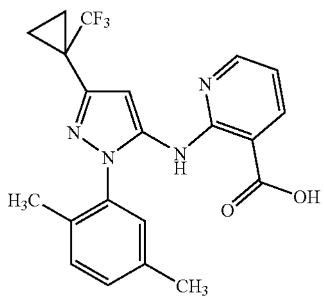 | 2-({1-(2,5-dimethylphenyl)-3-[1-(trifluoromethyl)cyclopropyl]-1H-pyrazol-5-yl}amino)nicotinic acid | | |
| 162 | 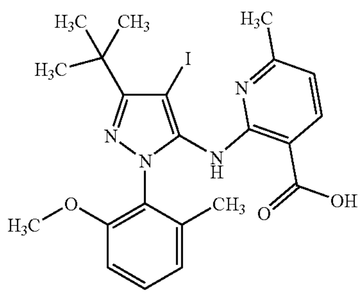 | 2-{[3-tert-butyl-4-iodo-1-(2-methoxy-6-methylphenyl)-1H-pyrazol-5-yl]amino}-6-methylnicotinic acid | | |
| 163 | 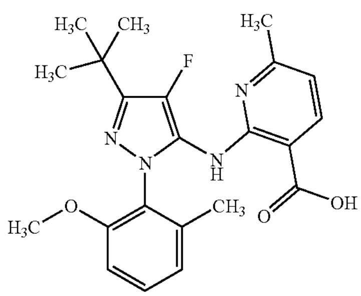 | 2-{[3-tert-butyl-4-fluoro-1-(2-methoxy-6-methylphenyl)-1H-pyrazol-5-yl]amino}-6-methylnicotinic acid | | |
| 164 | 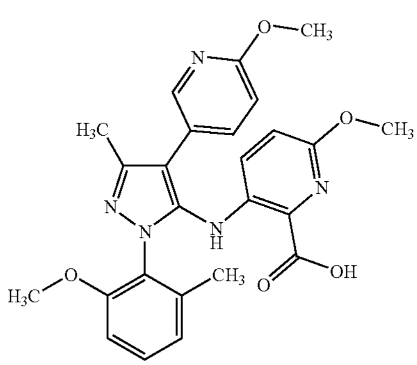 | 6-methoxy-3-{[1-(2-methoxy-6-methylphenyl)-4-(6-methoxypyridin-3-yl)-3-methyl-1H-pyrazol-5-yl]amino}pyridine-2-carboxylic acid | | |

TABLE 1-continued

| Example No | Structure | IUPAC name | LC-MS RT [min] | [M + H]+ |
|---|---|---|---|---|
| 165 | 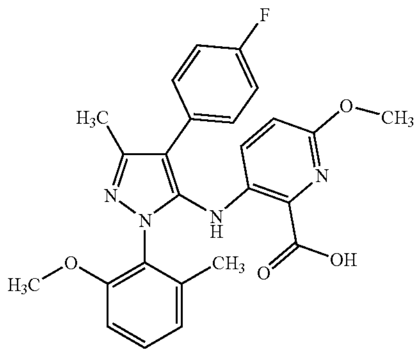 | 3-{[4-(4-fluorophenyl)-1-(2-methoxy-6-methylphenyl)-3-methyl-1H-pyrazol-5-yl]amino}-6-methoxypyridine-2-carboxylic acid | | |
| 166 | 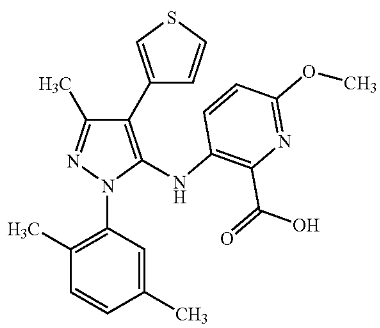 | 3-{[1-(2,5-dimethylphenyl)-3-methyl-4-(3-thienyl)-1H-pyrazol-5-yl]amino}-6-methoxypyridine-2-carboxylic acid | | |
| 167 | 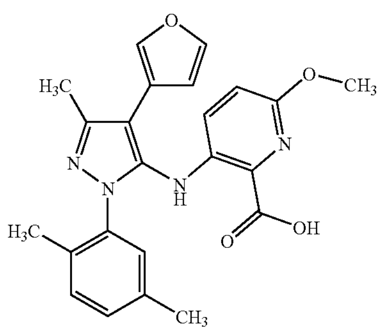 | 3-{[1-(2,5-dimethylphenyl)-4-(3-furyl)-3-methyl-1H-pyrazol-5-yl]amino}-6-methoxypyridine-2-carboxylic acid | | |
| 168 | 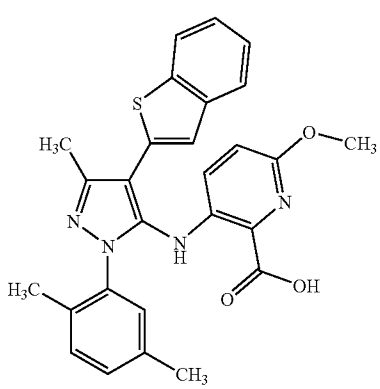 | 3-{[4-(1-benzothien-2-yl)-1-(2,5-dimethylphenyl)-3-methyl-1H-pyrazol-5-yl]amino}-6-methoxypyridine-2-carboxylic acid | | |

TABLE 1-continued

| Example No | Structure | IUPAC name | LC-MS RT [min] | [M + H]+ |
|---|---|---|---|---|
| 169 | 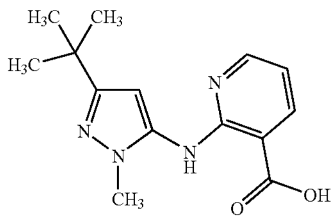 | 2-[(3-tert-butyl-1-methyl-1H-pyrazol-5-yl)amino]nicotinic acid | | |
| 170 | 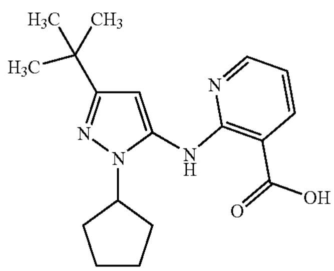 | 2-[(3-tert-butyl-1-cyclopentyl-1H-pyrazol-5-yl)amino]nicotinic acid | | |
| 171 | 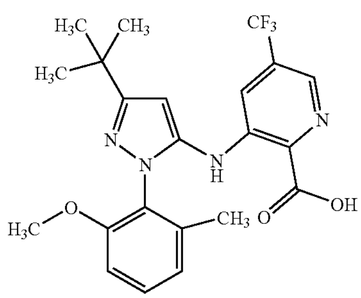 | 3-{[3-tert-butyl-1-(2-methoxy-6-methylphenyl)-1H-pyrazol-5-yl]amino}-5-(trifluoromethyl)pyridine-2-carboxylic acid | | |
| 172 | 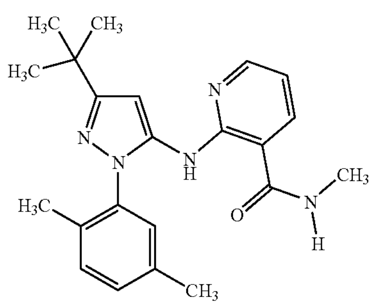 | 2-{[3-tert-butyl-1-(2,5-dimethylphenyl)-1H-pyrazol-5-yl]amino}-N-methylnicotinamide | | |
| 173 | 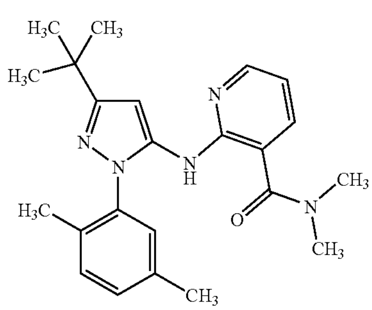 | 2-{[3-tert-butyl-1-(2,5-dimethylphenyl)-1H-pyrazol-5-yl]amino}-N,N-dimethylnicotinamide | | |

TABLE 1-continued

| Example No | Structure | IUPAC name | LC-MS RT [min] | [M + H]+ |
|---|---|---|---|---|
| 174 | 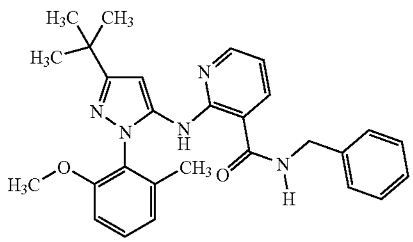 | N-benzyl-2-{[3-tert-butyl-1-(2-methoxy-6-methylphenyl)-1H-pyrazol-5-yl]amino}nicotinamide | | |
| 175 | 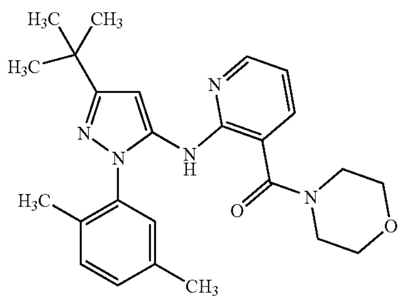 | N-[3-tert-butyl-1-(2,5-dimethylphenyl)-1H-pyrazol-5-yl]-3-(morpholin-4-ylcarbonyl)pyridin-2-amine | | |
| 176 | 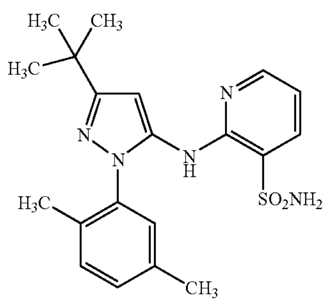 | 2-{[3-tert-butyl-1-(2,5-dimethylphenyl)-1H-yrazol-5-yl]amino}pyridine-3-sulfonamide | | |
| 177 | 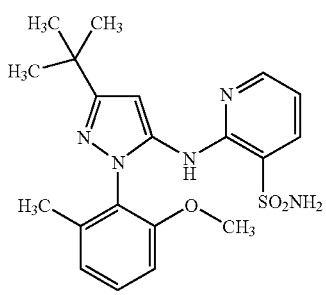 | 2-{[3-tert-butyl-1-(2-methoxy-6-methylphenyl)-1H-pyrazol-5-yl]amino}pyridine-3-sulfonamide | | |
| 178 | 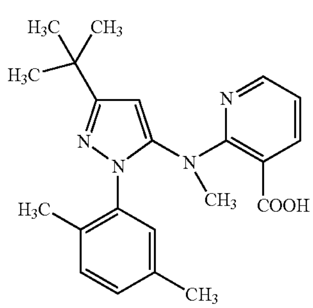 | 2-[[3-tert-butyl-1-(2,5-dimethylphenyl)-1H-pyrazol-5-yl](methyl)amino]nicotinic acid | | |

TABLE 1-continued

| Example No | Structure | IUPAC name | LC-MS RT [min] | [M + H]+ |
|---|---|---|---|---|
| 179 | 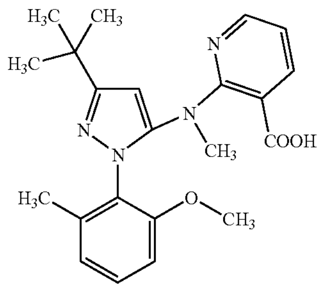 | 2-[[3-tert-butyl-1-(2-methoxy-6-methylphenyl)-1H-pyrazol-5-yl](methyl)amino]nicotinic acid | | |

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

The compounds of the present invention may be employed in the treatment of diabetes, including both type 1 and type 2 diabetes (non-insulin dependent diabetes mellitus). Such treatment may also delay the onset of diabetes and diabetic complications. The compounds may be used to prevent subjects with impaired glucose tolerance from proceeding to develop type 2 diabetes. Other diseases and conditions that may be treated or prevented using compounds of the invention in methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The compounds of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease.

The compounds of the present invention may also be useful for treating physiological disorders related to, for example, cell differentiation to produce lipid accumulating cells, regulation of insulin sensitivity and blood glucose levels, which are involved in, for example, abnormal pancreatic beta-cell function, insulin secreting tumors and/or autoimmune hypoglycemia due to autoantibodies to insulin, autoantibodies to the insulin receptor, or autoantibodies that are stimulatory to pancreatic beta-cells, macrophage differentiation which leads to the formation of atherosclerotic plaques, inflammatory response, carcinogenesis, hyperplasia, adipocyte gene expression, adipocyte differentiation, reduction in the pancreatic beta-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Compounds of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, β-adrenergic agents, α-interferon and drugs used to treat HIV infection.

The compounds of the present invention may be used alone or in combination with additional therapies and/or compounds known to those skilled in the art in the treatment of diabetes and related disorders. Alternatively, the methods and compounds described herein may be used, partially or completely, in combination therapy.

The compounds of the invention may also be administered in combination with other known therapies for the treatment of diabetes, including PPAR agonists, sulfonylurea drugs, non-sulfonylurea secretagogues, α-glucosidase inhibitors, insulin sensitizers, insulin secretagogues, hepatic glucose output lowering compounds, insulin and anti-obesity drugs. Such therapies may be administered prior to, concurrently with or following administration of the compounds of the invention. Insulin includes both long and short acting forms and formulations of insulin. PPAR agonist may include agonists of any of the PPAR subunits or combinations thereof. For example, PPAR agonist may include agonists of PPAR-α, PPAR-γ, PPAR-δ or any combination of two or three of the subunits of PPAR. PPAR agonists include, for example, rosiglitazone, troglitazone, and pioglitazone. Sulfonylurea drugs include, for example, glyburide, glimepiride, chlorpropamide, tolbutamide, and glipizide. α-glucosidase inhibitors that may be useful in treating diabetes when administered with a compound of the invention include acarbose, miglitol, and voglibose. Insulin sensitizers that may be useful in treating diabetes include PPAR-γ agonists such as the glitazones (e.g., troglitazone, pioglitazone, englitazone, MCC-555, rosiglitazone, and the like); biguanides such as metformin and phenformin; protein tyrosine phosphatase-1B (PTP-1B) inhibitors; dipeptidyl peptidase IV (DPP-IV) inhibitors; and thiazolidinediones and non-thiazolidinediones. Hepatic glucose output lowering compounds that may be useful in treating diabetes when administered with a compound of the invention include metformin, such as Glucophage and Glucophage XR. Insulin secretagogues that may be useful in treating diabetes when administered with a compound of the invention include sulfonylurea and non-sulfonylurea drugs: GLP-1, GIP, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, compounds of the invention are used in combination with insulin secretagogues to increase the sensitivity of pancreatic β-cells to the insulin secretagogue.

Compounds of the invention may also be used in methods of the invention in combination with anti-obesity drugs. Anti-obesity drugs include β-3 agonists; CB-1 antagonists; neuropeptide Y5 inhibitors; appetite suppressants, such as, for example, sibutramine (Meridia); and lipase inhibitors, such as, for example, orlistat (Xenical).

Compounds of the invention may also be used in methods of the invention in combination with drugs commonly used to treat lipid disorders in diabetic patients. Such drugs include, but are not limited to, HMG-CoA reductase inhibitors, nicotinic acid, lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triglyceride transport inhibitors, and fibric acid derivatives. HMG-CoA reductase inhibitors include, for example, lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention may also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

Such co-therapies may be administered in any combination of two or more drugs (e.g., a compound of the invention in combination with an insulin sensitizer and an anti-obesity drug). Such co-therapies may be administered in the form of pharmaceutical compositions, as described above.

Based on well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient (e.g., compounds) to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.0001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a therapeutically effective amount of a compound. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A therapeutically effective amount of a compound is that amount which produces a result or exerts an influence on the particular condition being treated. The compounds described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol; glycols; glycerol ketals; ethers; an oil; a fatty acid; a fatty acid ester or glyceride; or an acetylated fatty acid glyceride with or without the addition of a pharmaceutically acceptable surfactant; suspending agent; or emulsifying agent and other pharmaceutical adjuvants.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

The pharmaceutical compositions may be in the form of sterile injectable aqueous suspensions. Such suspensions may be formulated according to known methods using suitable dispersing or wetting agents and suspending agents, dispersing or wetting agents which may be a naturally occurring phosphatide, a condensation product of an alkylene oxide with a fatty acid, a condensation product of ethylene oxide with a long chain aliphatic alcohol, a condensation product of ethylene oxide with a partial ester derived form a fatty acid and a hexitol, or a condensation product of an ethylene oxide with a partial ester derived from a fatty acid and a hexitol anhydride.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug (e.g., compound) with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The compounds described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

It should be apparent to one of ordinary skill in the art that changes and modifications can be made to this invention without departing from the spirit or scope of the invention as it is set forth herein.

Biological Evaluation

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia, the following assays may be used.

In Vitro Assay

Insulin Secretion from INS-1 Cells

INS-1 cells were isolated from X-ray induced rat insulinoma (Asfari, et al., Endocrinology 130:167, 1992). INS-1 cells were seeded at 30,000 cells per well in Biocoat Collagen1 Cellware 96-well plates and incubated for 4-5 days. The cells were then treated for 2 days with complete media (RPMI 1640, 10% Fetal Bovine Serum, 100 µg/mL Penicillin/Streptomycin, 0.5 mM sodium pyruvate, 10 mM HEPES, and 50 µM beta-mercaptoethanol) adjusted to 3 mM glucose. After the two-day treatment, the cells were washed with Krebs-Ringer-Bicarbonate-HEPES (KRBH) containing 3 mM glucose. The cells were then incubated for 30 min in the same buffer. The cells were incubated for an additional 2 h in the presence of the desired concentration of glucose and compounds. The supernatants were harvested.

To determine the amount of insulin secreted, the supernatants were mixed with anti-insulin antibody and a tracer amount of $^{125}$I-insulin in phosphate buffered saline containing 0.5% bovine serum albumin. Protein A coated SPA (scintillation proximity assay) beads were added. The plates were incubated for 5-20 h and counted on a scintillation counter to measure insulin levels. Activity for compounds at a given concentration was expressed as a fold-stimulation of insulin secretion relative to controls.

Insulin Secretion from Dispersed Rat Islet Cells

Insulin secretion of dispersed rat islets mediated by a number of compounds of the present invention was measured as follows. Islets of Langerhans, isolated from male Sprague-Dawley rats (200-250 g), were digested using collagenase. The dispersed islet cells were treated with trypsin, seeded into 96 V-bottom plates, and pelleted. The cells were then cultured overnight in media with or without compounds of this invention. The media was aspirated, and the cells were pre-incubated with Krebs-Ringer-HEPES buffer containing 3 mM glucose for 30 minutes at 37° C. The pre-incubation buffer was removed, and the cells were incubated at 37° C. with Krebs-Ringer-HEPES buffer containing the appropriate glucose concentration (e.g., 8 mM) with or without compounds for an appropriate time. In some studies, an appropriate concentration of GLP-1 or forskolin was also included. A portion of the supernatant was removed and its insulin content was measured by SPA. The results were expressed as "fold over control" (FOC).

In this assay, an increase of insulin secretion from dispersed rat islet cells was defined as an increase of at least 1.4-fold.

In Vivo Assay

Effect of Compounds on Intraperitoneal Glucose Tolerance in Rats

The in vivo activities of the compounds of this invention when administered via oral gavage were examined in rats. Rats fasted overnight were given an oral dose of vehicle control or compound. Three hours later, basal blood glucose was measured, and the rats were given 2 g/kg of glucose intraperitoneally. Blood glucose was measured again after 15, 30, and 60 min. The representative compounds of this invention significantly reduced blood glucose levels relative to the vehicle following the IPGTT (Intraperitoneal Glucose Tolerance Test).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell, et al., (Am. J. Hypertens. 13:370-375, 2000). In monkeys, blood pressure and heart rate are monitored as described by Shen, et al., (J. Pharmacol. Exp. Therap. 278:1435-1443, 1996).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver, et al., (Proc. Natl. Acad. Sci. USA 98:5306-5311, 2001).

All publications and patents mentioned in the above specification are incorporated herein by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims. Those skilled in the art will recognize, or be able to ascertain using no more than routine experimentation, many equivalents to the specific embodiments of the invention described herein. Such equivalents are intended to be encompassed by the following claims.

We claim:

1. A heteroarylaminopyrazole compound of Formula (I)

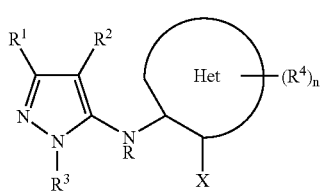

(I)

wherein

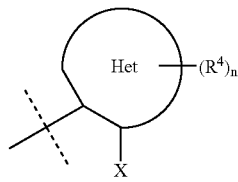

is a substituted heterocyclic aromatic ring radical selected from

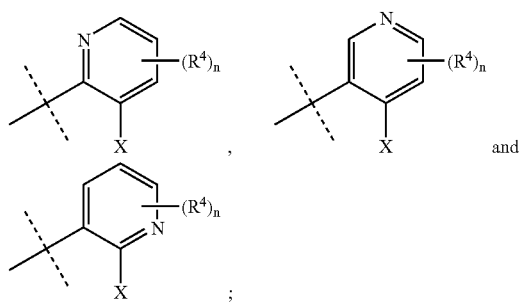

R is H, or $(C_1-C_6)$alkyl;

$R^1$ is H,
  $(C_1-C_6)$alkyl optionally substituted with phenyl, said phenyl being optionally substituted with halo, or [tri $(C_1-C_4)$alkyl]silyl,
  $(C_3-C_6)$alkenyl,
  $(C_3-C_6)$alkynyl,
  $(C_3-C_6)$cycloalkyl optionally substituted with up to two substituents selected from the group consisting of $(C_1-C_3)$alkyl, $CF_3$, and halo,
  $(C_1-C_3)$haloalkyl, or
  phenyl optionally substituted with up to two substituents selected from the group consisting of halo, $(C_1-C_6)$alkyl, $(C_1-C_6)$alkoxy, $(C_1-C_6)$alkylthio, $(C_1-C_3)$haloalkyl, $(C_1-C_3)$haloalkoxy, and cyano;

$R^2$ is H,
  halo,
  $(C_1-C_6)$alkyl,
  pyridyl optionally substituted with up to two substituents selected from the group consisting of $(C_1-C_6)$alkoxy, $(C_1-C_6)$alkylthio, halo, and $(C_1-C_6)$alkyl,
  phenyl optionally substituted with up to two substituents selected from the group consisting of $(C_1-C_6)$alkyl, $(C_1-C_6)$alkoxy, $(C_1-C_6)$alkylthio, cyano and halo,
  pyrimidyl,
  thienyl optionally substituted with up to two substituents selected from the group consisting of $(C_1-C_6)$alkyl, $(C_1-C_6)$alkoxy, $(C_1-C_6)$alkylthio, cyano and halo,
  benzothienyl, optionally substituted with up to two substituents selected from the group consisting of $(C_1-C_6)$alkyl, $(C_1-C_6)$alkoxy, $(C_1-C_6)$alkylthio, cyano and halo,
  or furyl optionally substituted with up to two substituents selected from the group consisting of $(C_1-C_6)$alkyl, $(C_1-C_6)$alkoxy, $(C_1-C_6)$alkylthio, cyano and halo;

$R^3$ is $(C_1-C_6)$alkyl,
  $(C_3-C_6)$cycloalkyl,
  $(C_2-C_3)$haloalkyl or phenyl optionally substituted with up to four substituents selected from the group consisting of
(C$_1$-C$_6$)alkyl optionally substituted with one (C$_1$-C$_4$)alkoxy,
halo,
(C$_1$-C$_3$)haloalkyl,
(C$_1$-C$_6$)alkoxy,
(C$_1$-C$_3$)haloalkoxy,
(C$_1$-C$_6$)alkylthio, and
cyano;
R$^4$ is (C$_1$-C$_6$)alkyl optionally substituted with one (C$_1$-C$_4$)alkoxy,
(C$_1$-C$_6$)alkoxy,
(C$_1$-C$_6$)alkylthio,
(C$_1$-C$_3$)haloalkyl,
(C$_1$-C$_3$)haloalkoxy, or
halo;
n =0, 1, 2, or 3;
X is CO$_2$R$^7$, CONR$^5$R$^6$, or SO$_2$NH$_2$;
R$^5$ is H, (C$_1$-C$_6$)alkyl, phenyl optionally substituted with halo or benzyl optionally substituted on the phenyl ring with halo;
R$^6$ is H or (C$_1$-C$_6$)alkyl;
or
R$^5$ and R$^6$, taken together with N atom to which they are attached, may form a piperidine, morpholine, thiomorpholine, or piperazine ring said piperazine optionally substituted on N with (C$_1$-C$_3$)alkyl;
R$^7$ is H,
(C$_1$-C$_6$)alkyl,
benzyl optionally substituted on the aryl ring with up to two substituents selected from the group consisting of
halo,
(C$_1$-C$_6$)alkyl,
(C$_1$-C$_3$)alkoxy,
(C$_1$-C$_3$)haloalkyl,
(C$_1$-C$_3$)haloalkoxy, and
(C$_1$-C$_6$)alkylthio;
phenyl optionally substituted with up to two substituents selected from the group consisting of
(C$_1$-C$_6$)alkyl,
halo,
(C$_1$-C$_6$)alkoxy,
(C$_1$-C$_3$)haloalkyl,
(C$_1$-C$_3$)haloalkoxy, and
(C$_1$-C$_6$)alkylthio;
or a pharmaceutically acceptable salt thereof;
provided that the compound of Formula (I) is not

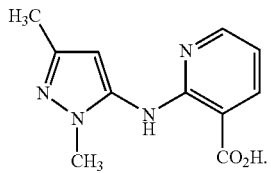

2. The compound of claim 1, wherein

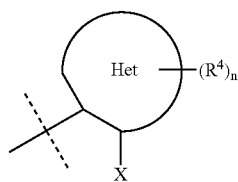

is a substituted heterocyclic aromatic ring radical selected from

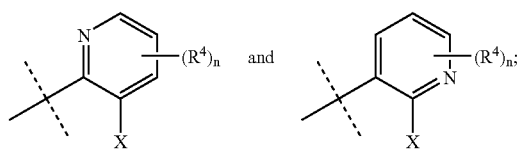

R is H, or (C$_1$-C$_6$)alkyl;
R$^1$ is H,
(C$_1$-C$_6$)alkyl optionally substituted with phenyl, said phenyl being optionally substituted with halo, or [tri (C$_1$-C$_4$)alkyl]silyl,
(C$_3$-C$_6$)alkenyl,
(C$_3$-C$_6$)alkynyl,
(C$_3$-C$_6$)cycloalkyl optionally substituted with up to two substituents selected from the group consisting of (C$_1$-C$_3$)alkyl, CF$_3$, and halo,
(C$_1$-C$_3$)haloalkyl, or
phenyl optionally substituted with up to two substituents selected from the group consisting of halo, (C$_1$-C$_6$)alkyl, (C$_1$-C$_6$)alkoxy, (C$_1$-C$_6$)alkylthio, (C$_1$-C$_3$)haloalkoxy, and cyano;
R$^2$ is H,
halo
(C$_1$-C$_6$)alkyl,
pyridyl optionally substituted with up to two substituents selected from the group consisting of (C$_1$-C$_6$)alkoxy, (C$_1$-C$_6$)alkylthio, halo, and (C$_1$-C$_6$)alkyl,
phenyl optionally substituted with up to two substituents selected from the group consisting of (C$_1$-C$_6$)alkyl, (C$_1$-C$_6$)alkoxy, (C$_1$-C$_6$)alkylthio, cyano and halo,
pyrimidyl,
thienyl optionally substituted with up to two substituents selected from the group consisting of (C$_1$-C$_6$)alkyl, (C$_1$-C$_6$)alkoxy, (C$_1$-C$_6$)alkylthio, cyano and halo,
benzothienyl, optionally substituted with up to two substituents selected from the group consisting of (C$_1$-C$_6$)alkyl, (C$_1$-C$_6$)alkoxy, (C$_1$-C$_6$)alkylthio, cyano and halo,
or furyl optionally substituted with up to two substituents selected from the group consisting of (C$_1$-C$_6$)alkyl, (C$_1$-C$_6$)alkoxy, (C$_1$-C$_6$)alkylthio, cyano and halo;
R$^3$ is (C$_1$-C$_6$)alkyl,
(C$_3$-C$_6$)cycloalkyl,
(C$_2$-C$_3$)haloalkyl or
phenyl optionally substituted with up to four substituents selected from the group consisting of
(C$_1$-C$_6$)alkyl optionally substituted with one (C$_1$-C$_4$)alkoxy,
halo, ($C_1$-$C_3$)haloalkyl,
($C_1$-$C_6$)alkoxy,
($C_1$-$C_3$)haloalkoxy,
($C_1$-$C_6$)alkylthio, and cyano;
$R^4$ is ($C_1$-$C_6$)alkyl optionally substituted with one ($C_1$-$C_4$) alkoxy,
($C_1$-$C_6$)alkoxy,
($C_1$-$C_6$)alkylthio,
($C_1$-$C_3$)haloalkyl,
($C_1$-$C_3$)haloalkoxy, or
halo;
n =0, 1, 2, or 3;
X is $CO_2R^7$, $CONR^5R^6$, or $SO_2NH_2$;
$R^5$ is H, ($C_1$-$C_6$)alkyl, phenyl optionally substituted with halo or benzyl optionally substituted on the phenyl ring with halo;
$R^6$ is H or ($C_1$-$C_6$)alkyl;
or
$R^5$ and $R^6$, taken together with N atom to which they are attached, may form a piperidine, morpholine, thiomorpholine, or piperazine ring said piperazine optionally substituted on N with ($C_1$-$C_3$)alkyl;
$R^7$ is H,
($C_1$-$C_6$)alkyl,
benzyl optionally substituted on the aryl ring with up to two substituents selected from the group consisting of halo,
($C_1$-$C_6$)alkyl,
($C_1$-$C_3$)alkoxy,
($C_1$-$C_3$)haloalkyl,
($C_1$-$C_3$)haloalkoxy, and
($C_1$-$C_6$)alkylthio;
phenyl optionally substituted with up to two substituents selected from the group consisting of
($C_1$-$C_6$)alkyl,
halo,
($C_1$-$C_6$)alkoxy,
($C_1$-$C_3$)haloalkyl,
($C_1$-$C_3$)haloalkoxy, and
($C_1$-$C_6$)alkylthio;
or a pharmaceutically acceptable salt thereof.

3. The compound of claim 1, wherein

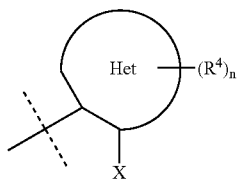

is a substituted heterocyclic aromatic ring radical selected from

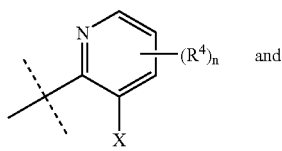 and 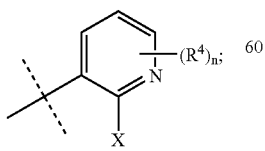;

R is H, or ($C_1$-$C_6$)alkyl;
$R^1$ is H, ($C_1$-$C_6$)alkyl optionally substituted with phenyl, said phenyl being optionally substituted with halo, or [tri($C_1$-$C_4$alkyl]silyl,
($C_3$-$C_6$)cycloalkyl optionally substituted with up to two substituents selected from the group consisting of ($C_1$-$C_3$)alkyl, $CF_3$, and halo,
($C_1$-$C_3$)haloalkyl, or
phenyl optionally substituted with up to two substituents selected from the group consisting of halo, ($C_1$-$C_6$)alkyl, ($C_1$-$C_6$)alkoxy, ($C_1$-$C_6$)alkylthio, ($C_1$-$C_3$)haloalkyl, ($C_1$-$C_3$)haloalkoxy, and cyano;
$R^2$ is H,
halo,
($C_1$-$C_6$)alkyl,
pyridyl optionally substituted with up to two substituents selected from the group consisting of ($C_1$-$C_6$)alkoxy, ($C_1$-$C_6$)alkylthio, halo, and ($C_1$-$C_6$)alkyl,
phenyl optionally substituted with up to two substituents selected from the group consisting of ($C_1$-$C_6$)alkyl, ($C_1$-$C_6$)alkoxy, ($C_1$-$C_6$)alkylthio, cyano and halo,
pyrimidyl;
$R^3$ is ($C_1$-$C_6$)alkyl,
($C_3$-$C_6$)cycloalkyl,
($C_2$-$C_3$)haloalkyl or
phenyl optionally substituted with up to four substituents selected from the group consisting of
($C_1$-$C_6$)alkyl optionally substituted with one ($C_1$-$C_4$) alkoxy,
halo,
($C_1$-$C_3$)haloalkyl,
($C_1$-$C_6$)alkoxy,
($C_1$-$C_3$)haloalkoxy,
($C_1$-$C_6$)alkylthio, and
cyano;
$R^4$ is ($C_1$-$C_6$)alkyl optionally substituted with one ($C_1$-$C_4$) alkoxy,
($C_1$-$C_6$)alkoxy,
($C_1$-$C_6$)alkylthio,
($C_1$-$C_3$)haloalkyl,
($C_1$-$C_3$)haloalkoxy, or
halo;
n =0, 1, or 2;
X is $CO_2R^7$ or $CONR^5R^6$;
$R^5$ is H or ($C_1$-$C_6$)alkyl;
$R^6$ is H or ($C_1$-$C_6$)alkyl;
or
$R^5$ and $R^6$, taken together with N atom to which they are attached, may form a piperidine, morpholine, thiomorpholine, or piperazine ring said piperazine optionally substituted on N with ($C_1$-$C_3$)alkyl;
$R^7$ is H,
($C_1$-$C_6$)alkyl;
or a pharmaceutically acceptable salt thereof.

4. The compound of claim 1, wherein

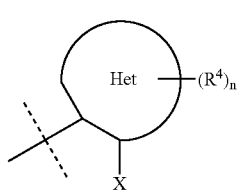

is a substituted heterocyclic aromatic ring radical selected from

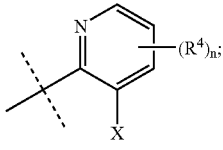

R is H, or $(C_1-C_6)$alkyl;
$R^1$ is H,
  $(C_1-C_6)$alkyl optionally substituted with phenyl, said phenyl being optionally substituted with halo, or [tri$(C_1-C_4)$alkyl]silyl,
  $(C_3-C_6)$cycloalkyl optionally substituted with up to two substituents selected from the group consisting of $(C_1-C_3)$alkyl, $CF_3$, and halo,
  $(C_1-C_3)$haloalkyl, or
  phenyl optionally substituted with up to two substituents selected from the group consisting of halo, $(C_1-C_6)$alkyl, $(C_1-C_6)$alkoxy, $(C_1-C_6)$alkylthio, $(C_1-C_3)$haloalkyl, $(C_1-C_3)$haloalkoxy, and cyano;
$R^2$ is H,
  halo,
  $(C_1-C_6)$alkyl,
  phenyl optionally substituted with up to two substituents selected from the group consisting of $(C_1-C_6)$alkyl, $(C_1-C_6)$alkoxy, $(C_1-C_6)$alkylthio, cyano and halo;
$R^3$ is $(C_1-C_6)$alkyl,
  $(C_3-C_6)$cycloalkyl,
  $(C_2-C_3)$haloalkyl or
    phenyl optionally substituted with up to four substituents selected from the group
    consisting of
      $(C_1-C_6)$alkyl optionally substituted with one $(C_1-C_4)$alkoxy,
      halo,
      $(C_1-C_3)$haloalkyl,
      $(C_1-C_6)$alkoxy,
      $(C_1-C_3)$haloalkoxy,
      $(C_1-C_6)$alkylthio, and cyano;
$R^4$ is $(C_1-C_6)$alkyl optionally substituted with one $(C_1-C_4)$alkoxy,
  $(C_1-C_6)$alkoxy,
  $(C_1-C_6)$alkylthio,
  $(C_1-C_3)$haloalkyl,
  $(C_1-C_3)$haloalkoxy, or
  halo;
n =0, 1, or 2;
X is $CO_2R^7$ or $CONR^5R^6$;
$R^5$ is H or $(C_1-C_6)$alkyl;
$R^6$ is H or $(C_1-C_6)$alkyl;
$R^7$ is H,
  $(C_1-C_6)$alkyl,
or a pharmaceutically acceptable salt thereof.

5. The compound of claim 1, wherein

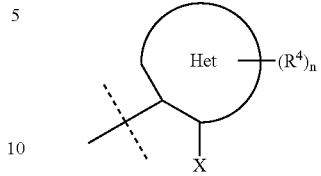

is a substituted heterocyclic aromatic ring radical selected from

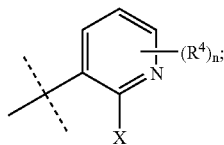

R is H, or $(C_1-C_6)$alkyl;
$R^1$ is H,
  $(C_1-C_6)$alkyl optionally substituted with phenyl, said phenyl being optionally substituted with halo, or [tri$(C_1-C_4)$alkyl]silyl,
  $(C_3-C_6)$cycloalkyl optionally substituted with up to two substituents selected from the group consisting of $(C_1-C_3)$alkyl, $CF_3$, and halo,
  $(C_1-C_3)$haloalkyl, or
  phenyl optionally substituted with up to two substituents selected from the group consisting of halo, $(C_1-C_6)$alkyl, $(C_1-C_6)$alkoxy, $(C_1-C_6)$alkythio, $(C_1-C_3)$haloalkyl, $(C_1-C_3)$haloalkoxy, and cyano;
$R^2$ is H,
  halo,
  $(C_1-C_6)$alkyl,
  phenyl optionally substituted with up to two substituents selected from the group consisting of $(C_1-C_6)$alkyl, $(C_1-C_6)$alkoxy, $(C_1-C_6)$alkylthio, cyano and halo;
$R^3$ is $(C_1-C_6)$alkyl,
  $(C_3-C_6)$cycloalkyl,
  $(C_2-C_3)$haloalkyl or
    phenyl optionally substituted with up to four substituents selected from the group
    consisting of
      $(C_1-C_6)$alkyl optionally substituted with one $(C_1-C_4)$alkoxy,
      halo,
      $(C_1-C_3)$haloalkyl,
      $(C_1-C_6)$alkoxy,
      $(C_1-C_3)$haloalkoxy,
      $(C_1-C_6)$alkylthio, and
      cyano;
$R^4$ is $(C_1-C_6)$alkyl optionally substituted with one $(C_1-C_4)$alkoxy,
  $(C_1-C_6)$alkoxy,
  $(C_1-C_6)$alkylthio,
  $(C_1-C_3)$haloalkyl,
  $(C_1-C_3)$haloalkoxy, or
  halo;
n =0, 1, or 2;
X is $C_2R^7$ or $CONR^5R^6$;
$R^5$ is H or $(C_1-C_6)$alkyl;
$R^6$ is H or $(C_1-C_6)$alkyl;

R⁷ is H, (C₁-C₆)alkyl, or a pharmaceutically acceptable salt thereof.

6. A compound according to claim 1 selected from the group consisting of 2-{[3-tert-butyl-1-(2-methylphenyl)-1H-pyrazol-5-yl]amino}-6-methylnicotinic acid; 2-{[3-cyclopentyl-1-(2-methylphenyl)-1H-pyrazol-5-yl]amino}nicotinic acid; 3-{[3-tert-butyl-1-(2-methyiphenyl)-1H-pyrazol-5-yl]amino}pyridine-2-carboxylic acid; 2-{[3-(2,2-dimethylpropyl)-1-(2-methylphenyl)-1H-pyrazol-5-yl]amino}nicotinic acid; 2-{[1-(2-chlorophenyl)-3-(4-fluorophenyl)-1H-pyrazol-5-yl]amino}nicotinic acid; 3-{[3-tert-butyl-1-(2,6-dimethylphenyl)-1H-pyrazol-5-yl]amino}pyridine-2-carboxylic acid; 2-{[3-tert-butyl-1-(5-fluoro-2-methylphenyl)-1H-pyrazol-5-yl]amino}nicotinic acid; 2-{[3-tert-butyl-1-(2,5-dimethyiphenyl)-1H-pyrazol-5-yl]amino}nicotinic acid; 2-{[3-tert-butyl-1-(5-fluoro-2-methylphenyl)-1H-pyrazol-5-yl]amino}-6-methylnicotinic acid; 2-{[3-tert-butyl-1-(2-methoxy-6-methylphenyl)-1H-pyrazol-5-yl]amino}-6-methylnicotinic acid; 2-{[3-tert-butyl-1-(2,5-dimethyiphenyl)-1H-pyrazol-5-yl]amino}-6-methylnicotinic acid; 2-{[3-tert-butyl-1-(2-methoxy-6-methylphenyl)-1H-pyrazol-5-yl]amino}-5-fluoronicotinic acid; 2-{[3-tert-butyl-1-(2,6-dimethyiphenyl)-1H-pyrazol-5-yl]amino}-5-fluoronicotinic acid; 2-{[3-tert-butyl-1-(5-fluoro-2-methylphenyl)-1H-pyrazol-5-yl]amino}-5-fluoronicotinic acid; 2-{[3-tert-butyl-1-(2,5-dimethylphenyl)-1H-pyrazol-5-yl]amino}-5-fluoronicotinic acid; 2-{[3-tert-butyl-1-(2,5-dimethylphenyl)-1H-pyrazol-5-yl]amino}-5-fluoronicotinic acid; 2-{[3-cyclohexyl-1-(2-methyiphenyl)-1H-pyrazol-5-yl]amino}nicotinic acid; 2-{[1-(5-fluoro-2-methylphenyl)-3-(4-fluorophenyl)-1H-pyrazol-5-yl]amino}nicotinic acid; 2-{[1-(2-methylphenyl)-3-phenyl-1H-pyrazol-5-yl]amino}nicotinic acid; 2-{[3-(4-fluorophenyl)-1-(2-methyiphenyl)-1H-pyrazol-5-yl]amino}nicotinic acid; 2-{[1-(2,5-dimethylphenyl)-3-(4-fluorophenyl)-1H-pyrazol-5-yl]amino}nicotinic acid; 2-{[1-(2,5-dimethylphenyl)-3-phenyl-1H-pyrazol-5-yl]amino}nicotinic acid; 2-{[3-(4-fluorophenyl)-1-(2-methoxy-5-methyiphenyl)-1H-pyrazol-5-yl]amino}nicotinic acid; 2-{[3-(4-fluorophenyl)-1-(5-methoxy-2-methylphenyl)-1H-pyrazol-5-yl]amino}nicotinic acid; 2-{[1-(2,5-dimethylphenyl)-3-phenyl-1H-pyrazol-5-yl]amino}-6-methylnicotinic acid; 2-{[1-(2,5-dimethylphenyl)-3-(4-fluorophenyl)-1H-pyrazol-5-yl]amino}-6-methylnicotinic acid; 2-{[3-(4-fluorophenyl)-1-(2-methoxy-6-methylphenyl)-1H-pyrazol-5-yl]amino}-6-methylnicotinic acid; 2-{[3-(1,1-dimethylpropyl)-1-(3-methoxy-2-methylphenyl)-1H-pyrazol-5-Yl]amino}nicotinic acid; 2-{[3-(1,1-dimethylpropyl)-1-(5-fluoro-2-methylphenyl)-1H-pyrazol-5-Yl]amino}nicotinic acid; 2-{[3-tert-butyl-1-(2-chlorophenyl)-1H-pyrazol-5-yl]amino}nicotinic acid; 2-{[3-tert-butyl-1-(2,6-dimethyiphenyl)-1H-pyrazol-5-yl]amino}nicotinic acid; 2-{[3-tert-butyl-1-(2-methoxy-6-methylphenyl)-1H-pyrazol-5-yl]amino}nicotinic acid; and 3-{[3-tert-butyl-1-(2-methoxy-6-methylphenyl)-1H-pyrazol-5-yl]amino}-5-(trifluoromethyl)pyridine-2-carboxylic acid.

7. A pharmaceutical composition comprising an effective amount of a compound of claim 1, or a pharmaceutically acceptable salt thereof, in combination with a pharmaceutically acceptable carrier.

8. A method of treating diabetes comprising administering to a subject in need thereof a therapeutically effective amount of i) a compound of claim 1, or ii) a pharmaceutical composition of claim 7.

9. The method of claim 8, wherein said diabetes is selected from the group consisting of type 1 diabetes, type 2 diabetes, maturity-onset diabetes of the young, latent autoimmune diabetes adult, and gestational diabetes.

* * * * *